(12) United States Patent     (10) Patent No.:   US 12,698,322 B2

Martinez-Martin     (45) Date of Patent:     Aug. 4, 2026

(54) METHODS FOR MODULATING HOST CELL SURFACE INTERACTIONS WITH SARS-COV-2

(71) Applicant: Genentech, Inc., South San Francisco, CA (US)

(72) Inventor: Nadia Martinez-Martin, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 575 days.

(21) Appl. No.: 18/321,396

(22) Filed: May 22, 2023

(65) Prior Publication Data

US 2024/0025972 A1     Jan. 25, 2024

Related U.S. Application Data

(63) Continuation of application No. PCT/US2021/060464, filed on Nov. 23, 2021.

(60) Provisional application No. 63/117,440, filed on Nov. 23, 2020.

(51) Int. Cl.

| | |
|---|---|
| *C07K 14/165* | (2006.01) |
| *A61K 39/00* | (2006.01) |
| *A61K 45/06* | (2006.01) |
| *C07K 16/10* | (2026.01) |
| *C07K 16/104* | (2026.01) |
| *C07K 16/24* | (2006.01) |
| *C07K 16/28* | (2006.01) |
| *G01N 33/68* | (2006.01) |

(52) U.S. Cl.

CPC ............ *C07K 16/104* (2026.01); *A61K 45/06* (2013.01); *C07K 14/165* (2013.01); *C07K 16/244* (2013.01); *C07K 16/2803* (2013.01); *G01N 33/6869* (2013.01); *G01N 2800/52* (2013.01)

(58) Field of Classification Search

CPC .............. A61K 45/06; A61K 2039/505; A61K 31/713; C07K 14/165; C07K 16/244

See application file for complete search history.

(56) References Cited

U.S. PATENT DOCUMENTS

| | | | |
|---|---|---|---|
| 8,574,573 B2 | 11/2013 | Carballido Herrera et al. |
| 10,787,501 B1 | 9/2020 | Babb et al. |
| 2020/0157237 A1 | 5/2020 | Regev et al. |

FOREIGN PATENT DOCUMENTS

| | | |
|---|---|---|
| WO | WO-99/32629 A1 | 7/1999 |
| WO | WO-2014/126277 A1 | 8/2014 |
| WO | WO-2016/008051 A1 | 1/2016 |
| WO | WO-2020/201168 A1 | 10/2020 |
| WO | WO-2021/207858 A1 | 10/2021 |

OTHER PUBLICATIONS

Morsy, "NCAM protein and SARS-COV-2 surface proteins: In-silico hypothetical evidence for the immunopathogenesis of Guillain-Barre syndrome", Medical Hypothesis, 2020 available online Oct. 8, 2020, 145:1-5.*

Brockbank et al., "SARS-CoV-2 comprehensive receptor profiling: mechanistic insight to drive new therapeutic strategies," bioRxiv. (Mar. 2021) (24 pages).

Cao et al., "A membrane protein display platform for receptor interactome discovery" PNAS. 118(39): e2025451118 (Sep. 2021) (12 pages).

Cao et al., "Unbiased Identification of Extracellular Protein-Protein Interactions for Drug Target and Biologic Drug Discovery" IntechOpen. DOI: http://dx.doi.org/10.5772/intechopen.97310 (Jun. 2021) (21 pages).

Dutta, "Study identifies three novel binding receptors for SARS-CoV-2," retrieved from the internet: URL: https://www.news-medical.net/news/20210312/Study-identifies-three-novel-binding-receptors-for-SARS-CoV-2.aspx.(Mar. 2021) (4 pages).

Gordon et al., "A SARS-CoV-2 protein interaction map reveals targets for drug repurposing," Nature. 583:459-468 (Apr. 2020) (30 pages).

Liu et al., "Research and Development on Therapeutic Agents and Vaccines for COVID-19 and Related Human Coronavirus Diseases," American Chemical Society Central Science. 6:315-331 (Mar. 2020).

Martinez-Martin, "Technologies for Proteome-Wide Discovery of Extracellular Host-Pathogen Interactions," Journal of Immunology Research. 2017:2197615 (Jan. 2017) (18 pages).

Verschueren et al., "The Immunoglobulin Superfamily Receptome Defines Cancer-Relevant Networks Associated with Clinical Outcome," Cell. 182:329-344 (Jul. 2020) (36 pages).

International Preliminary Report on Patentability for International Patent Application No. PCT/US2021/060464, dated May 16, 2023 (23 pages).

International Search Report and Written Opinion for International Application No. PCT/US2021/060464, dated Apr. 8, 2022 (34 pages).

Invitation to Pay Additional Fees for International Patent Application No. PCT/US2021/060464, dated Feb. 18, 2022 (29 pages).

Boraschi et al., "The family of the interleukin-1 receptors," Immunological Reviews. 281 (1):197-232 (Dec. 2017).

Conti et al., "Induction of pro-inflammatory cytokines (IL-1 and IL-6) and lung inflammation by coronavirus-19 (COVI-19 or SARS-CoV-2): Anti-inflammatory strategies," Journal of Biological Regulators & Homeostatic Agents. 34(2): 327-331 (Apr. 2020).

(Continued)

*Primary Examiner* — Barry A Chestnut

(74) *Attorney, Agent, or Firm* — Genentech, Inc.

(57)       ABSTRACT

Provided herein are methods of treating or preventing SARS-CoV-2 infection comprising modulating interactions between the SARS-CoV-2 spike protein and plasma membrane-expressed host cell proteins, as well as methods of identifying modulators of such interactions.

20 Claims, 37 Drawing Sheets
(37 of 37 Drawing Sheet(s) Filed in Color)

Specification includes a Sequence Listing.

(56)         References Cited

OTHER PUBLICATIONS

Dhama et al., "An update on SARS-CoV-2/COVID-19 with particular reference to its clinical pathology, pathogenesis, immunopathology and mitigation strategies," Travel Medicine and Infectious Disease. 37: 1-10 (May 2020).

Fraser et al., "Novel outcome biomarkers identified with targeted proteomic analyses of plasma from critically ill coronavirus disease 2019 patients," Critical Care Explorations. 2(9):1-10 (Aug. 2020).

Han et al., "IL-36 family cytokines in protective versus destructive inflammation", Cellular Signaling. 75: 1-13 (Sep. 2020).

Kumar, "COVID-19: A drug repurposing and biomarker identification by using comprehensive gene-disease associations through protein-protein interaction network analysis," <https://www.preprints. org/manuscript/202003.0440/v1>, dated Mar. 30, 2020, retrieved on Aug. 16, 2024 (54 pages).

Malabendu et al., "IL-12 p40 homodimer, the so-called biologically inactive molecule, induces nitric oxide synthase in microglia via IL-12Rβ1," GLIA. 57(14):1553-1565 (Mar. 2009).

Tang et al., "IL-12 RB1 genetic variants contribute to human susceptibility to severe acute respiratory syndrome infection among Chinese," PLoS One, 3(5):1-7 (May 2008).

"Approaches to Drug Therapy for COVID-19", National Center for Global Health and Medicine / Fujita Health University, The Japanese Association for Infectious Diseases, https://www.kansensho. or.jp/uploads/files/topics/2019ncov/covid19_drug_200817. pdf),(6th Edition):19 (Aug. 13, 2020).

Manso et al., Contactin-1 lgG4 antibodies cause paranode dismantling and conduction defects, Brain 139:1700-1712, ( 2016).

* cited by examiner

FIG. 9B
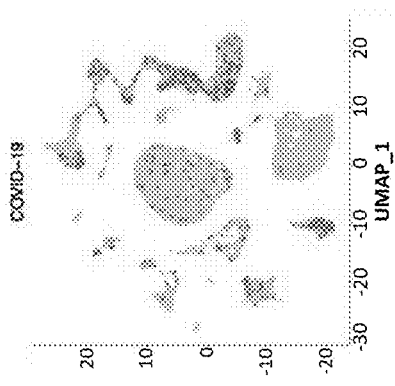
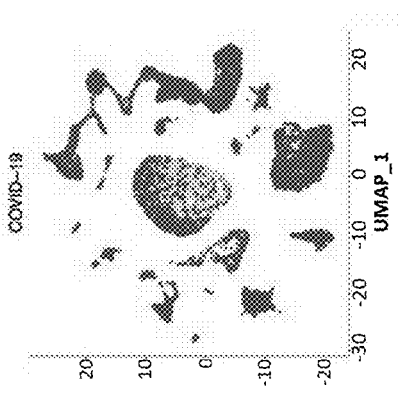
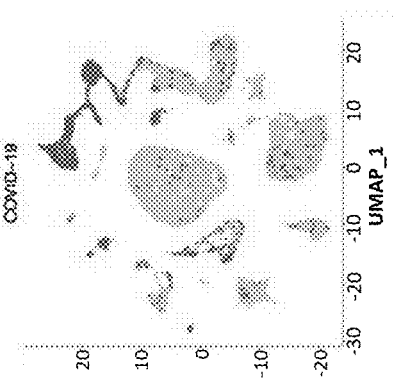
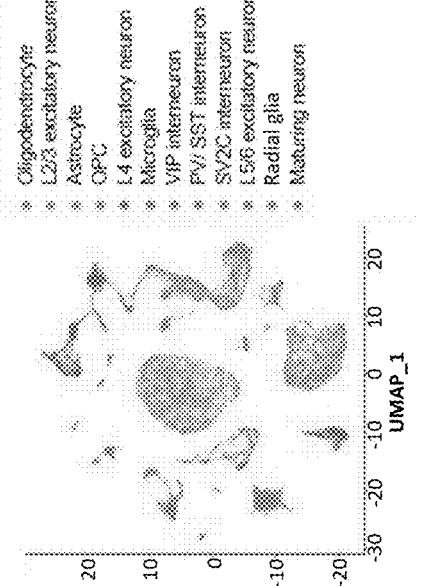
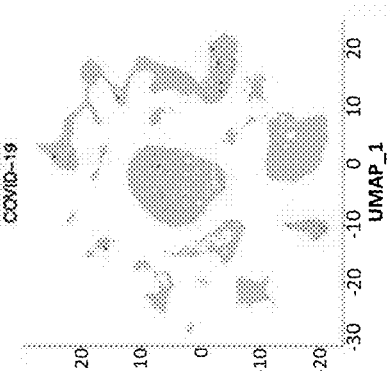

METHODS FOR MODULATING HOST CELL SURFACE INTERACTIONS WITH SARS-COV-2

CROSS-REFERENCE TO RELATED APPLICATIONS

This application is a continuation of International Patent Application No. PCT/US2021/060464, filed on Nov. 23, 2021, which claims benefit to U.S. Provisional Application No. 63/117,440, filed on Nov. 23, 2020, the entire contents of which are incorporated herein by reference in their entirety.

SEQUENCE LISTING

The instant application contains a Sequence Listing which has been submitted electronically in XML format and is hereby incorporated by reference in its entirety. Said XML copy, created on May 11, 2023, is named 50474-246003_SL.xml and is 18,653 bytes in size.

FIELD OF THE INVENTION

Provided herein are methods of treating or preventing SARS-CoV-2 infection comprising modulating interactions between the SARS-CoV-2 spike protein and plasma membrane-expressed host cell proteins, as well as methods of identifying modulators of such interactions.

BACKGROUND

Coronaviruses (CoV) are positive-stranded RNA viruses with a crown-like appearance under an electron microscope due to the presence of spike glycoproteins on the envelope. They are a large family of viruses that cause illness ranging from the common cold to more severe diseases such as Middle East respiratory syndrome (MERS CoV) and severe acute respiratory syndrome (SARS-CoV).

COVID-19, which is the acronym of "coronavirus disease 2019," is caused by a new coronavirus strain (severe acute respiratory syndrome coronavirus 2 (SARS-CoV-2)) that had not been previously identified in humans and was newly named on 11 Feb. 2020 by the World Health Organization (WHO). An epidemic of cases with unexplained lower respiratory tract infections was first detected in Wuhan, the largest metropolitan area in China's Hubei province, and was reported to the WHO Country Office in China on 31 Dec. 2019. A pandemic was subsequently declared by the WHO on 11 Mar. 2020. According to the WHO, as of 16 Nov. 2020, more than 54 million cases of COVID-19 had been reported worldwide, with over 1.32 million deaths. As of 16 Nov. 2021, more than 253 million cases of COVID-19 had been reported worldwide, with over 5 million deaths.

Despite intensive research efforts, much remains to be understood about the host cell receptors and cellular factors that mediate SARS-CoV-2 entry and initiation of infection, in part due to the lack of sensitive technologies for the study of membrane protein interactomes. This limited understanding has resulted in a dearth of therapeutically effective options for the treatment and prevention of SARS-CoV-2 infection.

Most research and drug development efforts have focused on the mammalian cell surface-expressed protein angiotensin-converting enzyme 2 (ACE2), which is known to be involved in coronavirus entry; however, mounting evidence shows a multi-organ tropism for SARS-CoV-2 that cannot be explained by ACE2 expression patterns. For example, studies have shown that SARS-CoV-2 can infect nervous tissue, and an elevated fraction of patients relative to SARS-CoV-1 show a range of neurological symptoms, from migraine, olfactory and gustatory dysfunctions to impaired consciousness. The extended tropism and transmissibility of SARS-CoV-2 may be due to interactions with additional, currently unknown host factors, e.g., factors that facilitate infection of cells having low ACE2 expression levels or factors involved in ACE2-independent routes of infection.

Thus, there is an unmet need for methods of identifying new interacting partners of the SARS CoV-2 spike protein; methods for identifying modulators of novel interactions; and methods for treating or preventing SARS-CoV-2 infection using modulators of such interactions.

SUMMARY OF THE INVENTION

In one aspect, the disclosure features a method of treating an individual having a SARS-CoV-2 infection comprising administering to the individual an effective amount of a contactin-1 (CNTN1) antagonist, an interleukin 12 receptor subunit beta 1 (IL12RB1) antagonist, or an interleukin 1 receptor accessory protein like 2 (IL1RAPL2) antagonist.

In another aspect, the disclosure features a method of reducing SARS-CoV-2 attachment to a cell of an individual comprising administering to the individual an effective amount of a CNTN1 antagonist, an IL12RB1 antagonist, or an IL1RAPL2 antagonist.

In some aspects, the administering comprises contacting the cell of the individual with an effective amount of a CNTN1 antagonist, an IL12RB1 antagonist, or an IL1RAPL2 antagonist.

In another aspect, the disclosure features a method of decreasing SARS-CoV-2 infection in an individual comprising administering to the individual an effective amount of a CNTN1 antagonist, an IL12RB1 antagonist, or an IL1RAPL2 antagonist.

In some aspects, (a) the CNTN1 antagonist results in a decrease in the binding of CNTN1 and the SARS-CoV-2 spike (S) protein relative to binding of the two proteins in the absence of the antagonist; (b) the IL12RB1 antagonist results in a decrease in the binding of IL12RB1 and the SARS-CoV-2 S protein relative to binding of the two proteins in the absence of the antagonist; or (c) the IL1RAPL2 antagonist results in a decrease in the binding of IL1RAPL2 and the SARS-CoV-2 S protein relative to binding of the two proteins in the absence of the antagonist.

In some aspects, the CNTN1 antagonist, IL12RB1 antagonist, or IL1RAPL2 antagonist reduces the extent and/or severity of SARS-CoV-2 infection of the individual relative to infection in the absence of the CNTN1 antagonist, IL12RB1 antagonist, or IL1RAPL2 antagonist, respectively.

In some aspects, the CNTN1 antagonist, IL12RB1 antagonist, or IL1RAPL2 antagonist is a small molecule, an antibody or antigen-binding fragment thereof, a peptide, a mimic, or an inhibitory nucleic acid. In some aspects, the inhibitory nucleic acid is an antisense oligonucleotide (ASO) or a small interfering RNA (siRNA).

In some aspects, the CNTN1 antagonist, IL12RB1 antagonist, or IL1RAPL2 antagonist is a peptide.

In some aspects, the CNTN1 antagonist, IL12RB1 antagonist, or IL1RAPL2 antagonist is an antibody or antigen-binding fragment thereof. In some aspects, the antibody or antigen-binding fragment thereof binds the SARS-CoV-2 S protein and inhibits its binding to CNTN1, IL12RB1, and/or IL1RAPL2. In some aspects, the antibody or antigen-binding fragment thereof binds CNTN1, IL12RB1, or IL1RAPL2. In some aspects, the antibody or antigen-binding fragment thereof inhibits the binding of CNTN1, IL12RB1, or IL1RAPL2 to the SARS-CoV-2 S protein. In some aspects, the antibody or antigen-binding fragment thereof inhibits the binding of CNTN1, Il12RB1, or IL1RAPL2 to the SARS-CoV-2 S protein receptor binding domain (RBD). In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody is a bispecific antibody. In some aspects, the bispecific antibody binds (a) angiotensin-converting enzyme 2 (ACE2) and CNTN1; (b) ACE2 and IL12RB1; or (c) ACE2 and IL1RAPL2.

In another aspect, the disclosure features a method of prophylaxis against secondary infection of nervous tissue in an individual having a SARS-CoV-2 infection comprising administering to the individual an effective amount of a CNTN1 antagonist or an IL1RAPL2 antagonist.

In some aspects, (a) the CNTN1 antagonist results in a decrease in the binding of CNTN1 and the SARS-CoV-2 S protein relative to binding of the two proteins in the absence of the antagonist; or (b) the IL1RAPL2 antagonist results in a decrease in the binding of IL1RAPL2 and the SARS-CoV-2 S protein relative to binding of the two proteins in the absence of the antagonist.

In some aspects, the CNTN1 antagonist or IL1RAPL2 antagonist reduces the extent and/or severity of SARS-CoV-2 infection of nervous tissue in the individual relative to infection in the absence of the CNTN1 antagonist or IL1RAPL2 antagonist, respectively.

In some aspects, the CNTN1 antagonist or IL1RAPL2 antagonist is a small molecule, an antibody or antigen-binding fragment thereof, a peptide, a mimic, or an inhibitory nucleic acid. In some aspects, the inhibitory nucleic acid is an ASO or a siRNA.

In some aspects, the CNTN1 antagonist or IL1RAPL2 antagonist is a peptide.

In some aspects, the CNTN1 antagonist or IL1RAPL2 antagonist is an antibody or antigen-binding fragment thereof. In some aspects, the antibody or antigen-binding fragment thereof binds the SARS-CoV-2 S protein and inhibits its binding to CNTN1 and/or IL1RAPL2. In some aspects, the antibody or antigen-binding fragment thereof binds CNTN1 or IL1RAPL2. In some aspects, the antibody or antigen-binding fragment thereof inhibits the binding of CNTN1 or IL1RAPL2 to the SARS-CoV-2 S protein. In some aspects, the antibody or antigen-binding fragment thereof inhibits the binding of CNTN1 or IL1RAPL2 to the SARS-CoV-2 S protein RBD. In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody is a bispecific antibody. In some aspects, the bispecific antibody binds (a) ACE2 and CNTN1, (b) ACE2 and IL1RAPL2, or (c) CNTN1 and IL1RAPL2.

In another aspect, the disclosure features a method of prophylaxis against secondary infection of immune cells and/or lymphoid tissue in an individual having a SARS-CoV-2 infection comprising administering to the individual an effective amount of an IL12RB1 antagonist.

In some aspects, the IL12RB1 antagonist results in a decrease in the binding of IL12RB1 and the SARS-CoV-2 S protein relative to binding of the two proteins in the absence of the antagonist.

In some aspects, the IL12RB1 antagonist reduces the extent and/or severity of SARS-CoV-2 infection of immune cells and/or lymphoid tissue in the individual relative to infection in the absence of the IL12RB1 antagonist.

In some aspects, the IL12RB1 antagonist is a small molecule, an antibody or antigen-binding fragment thereof, a peptide, a mimic, or an inhibitory nucleic acid. In some aspects, the inhibitory nucleic acid is an ASO or a siRNA.

In some aspects, the IL12RB1 antagonist is a peptide.

In some aspects, the IL12RB1 antagonist is an antibody or antigen-binding fragment thereof. In some aspects, the antibody or antigen-binding fragment thereof binds the SARS-CoV-2 S protein and inhibits its binding to IL12RB1. In some aspects, the antibody or antigen-binding fragment thereof binds IL12RB1. In some aspects, the antibody or antigen-binding fragment thereof inhibits the binding of IL12RB1 to the SARS-CoV-2 S protein. In some aspects, the antibody or antigen-binding fragment thereof inhibits the binding of IL12RB1 to the SARS-CoV-2 S protein RBD. In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody is a bispecific antibody. In some aspects, the bispecific antibody binds ACE2 and IL12RB1.

In another aspect, the disclosure features a method of prophylaxis against secondary infection of the lungs in an individual having a SARS-CoV-2 infection comprising administering to the individual an effective amount of a CNTN1 antagonist or an IL12RB1 antagonist.

In some aspects, (a) the CNTN1 antagonist results in a decrease in the binding of CNTN1 and the SARS-CoV-2 S protein relative to binding of the two proteins in the absence of the antagonist; or (b) the IL12RB1 antagonist results in a decrease in the binding of IL12RB1 and the SARS-CoV-2 S protein relative to binding of the two proteins in the absence of the antagonist.

In some aspects, the CNTN1 antagonist or IL12RB1 antagonist reduces the extent and/or severity of SARS-CoV-2 infection of the lungs in the individual relative to infection in the absence of the CNTN1 antagonist or IL12RB1 antagonist, respectively.

In some aspects, the CNTN1 antagonist or IL12RB1 antagonist is a small molecule, an antibody or antigen-binding fragment thereof, a peptide, a mimic, or an inhibitory nucleic acid. In some aspects, the inhibitory nucleic acid is an ASO or a siRNA.

In some aspects, the CNTN1 antagonist or IL12RB1 antagonist is a peptide.

In some aspects, the CNTN1 antagonist or IL12RB1 antagonist is an antibody or antigen-binding fragment thereof. In some aspects, the antibody or antigen-binding fragment thereof binds the SARS-CoV-2 S protein and inhibits its binding to CNTN1 and/or IL12RB1. In some aspects, the antibody or antigen-binding fragment thereof binds CNTN1 or IL12RB1. In some aspects, the antibody or antigen-binding fragment thereof inhibits the binding of CNTN1 or IL12RB1 to the SARS-CoV-2 S protein. In some aspects, the antibody or antigen-binding fragment thereof inhibits the binding of CNTN1 or IL12RB1 to the SARS-CoV-2 S protein RBD. In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody is a bispecific antibody. In some aspects, the bispecific antibody binds (a) ACE2 and CNTN1, (b) ACE2 and IL12RB1, or (c) CNTN1 and IL12RB1.

In some aspects, the individual has COVID-19. In some aspects, the individual has COVID-19 pneumonia or acute respiratory distress syndrome (ARDS).

In some aspects, the method further comprises administering to the individual at least one additional therapy. In some aspects, the CNTN1 antagonist, IL12RB1 antagonist, or IL1RAPL2 antagonist is administered to the individual prior to, concurrently with, or after the at least one additional therapy.

In some aspects, the at least one additional therapy is an ACE2 antagonist.

In some aspects, the at least one additional therapy is a neuropilin-2 (NRP2) antagonist.

In some aspects, the at least one additional therapy is a supportive care therapy, an anti-viral therapy, or a corticosteroid therapy.

In some aspects, the supportive care therapy comprises oxygen therapy.

In some aspects, the anti-viral therapy comprises alpha-interferon, lopinavir, ritonavir, lopinavir/ritonavir, remdesivir, ribavirin, hydroxychloroquine, chloroquine, umifenovir, favipiravir, or a combination thereof.

In some aspects, the corticosteroid therapy comprises prednisone, prednisolone, methylprednisolone, methylprednisolone sodium succinate, dexamethasone, dexamethasone triamcinolone, hydrocortisone, betamethasone, or a combination thereof. In some aspects, the corticosteroid therapy is a low-dose corticosteroid therapy.

In some aspects, the method achieves a greater improvement in clinical outcome compared to standard of care (SOC).

In some aspects, the clinical outcome is time to clinical improvement (TTCI) defined as a National Early Warning Score 2 (NEWS2) of ≤2 maintained for 24 hours.

In some aspects, the clinical outcome is incidence of mechanical ventilation.

In some aspects, the clinical outcome is incidence of intensive care unit (ICU) stay.

In some aspects, the clinical outcome is duration of ICU stay.

In some aspects, the clinical outcome is time to clinical failure defined as the time to death, mechanical ventilation, ICU admission, or withdrawal, whichever occurs first.

In some aspects, the clinical outcome is time to hospital discharge; or ready for discharge as evidenced by normal body temperature and respiratory rate, and stable oxygen saturation on ambient air or ≤2 L supplemental oxygen.

In some aspects, the clinical outcome is duration of supplemental oxygen.

In some aspects, the clinical outcome is selected from the group consisting of incidence of vasopressor use, duration of vasopressor use, incidence of extracorporeal membrane oxygenation (ECMO), incidence of starting dialysis, SARS-CoV-2 viral load on Day 15 or day of hospital discharge (whichever occurs first), and proportion of individuals with secondary bacterial infections.

In some aspects, the method is associated with an acceptable safety outcome compared with SOC.

In some aspects, the safety outcome is selected from the group consisting of: incidence and severity of adverse events; incidence and severity of adverse events with severity determined according to National Cancer Institute Common Terminology Criteria for Adverse Events (NCI CTCAE) v5.0; change from baseline in targeted vital signs; and change from baseline in targeted clinical laboratory test results.

In some aspects, the SOC comprises supportive care, administration of one or more anti-viral agents, and/or administration of one or more low-dose corticosteroids.

In some aspects, the individual is a human.

In another aspect, the disclosure features a method of identifying a modulator of the interaction between the SARS-CoV-2 S protein and CNTN1, IL12RB1, or IL1RAPL2, the method comprising (a) providing a candidate modulator; (b) contacting the SARS-CoV-2 S protein RBD with CNTN1, IL12RB1, or IL1RAPL2 in the presence or absence of the candidate modulator under conditions permitting the binding of the SARS-CoV-2 S protein RBD to CNTN1, IL12RB1, or IL1RAPL2; and (c) measuring the binding of the protein of the SARS-CoV-2 S protein RBD to CNTN1, IL12RB1, or IL1RAPL2, wherein an increase or decrease in binding in the presence of the candidate modulator relative to binding in the absence of the candidate modulator identifies the candidate modulator as a modulator of the interaction between the SARS-CoV-2 S protein and CNTN1, IL12RB1, or IL1RAPL2.

In another aspect, the disclosure features a method of identifying a modulator of a downstream activity of the SARS-CoV-2 S protein, the method comprising (a) providing a candidate modulator; (b) contacting the SARS-CoV-2 S protein RBD with CNTN1, IL12RB1, or IL1RAPL2 in the presence or absence of the candidate modulator under conditions permitting the binding of the SARS-CoV-2 S protein RBD to CNTN1, IL12RB1, or IL1RAPL2; and (c) measuring a downstream activity of the SARS-CoV-2 S protein RBD, wherein a change in the downstream activity in the presence of the candidate modulator relative to the downstream activity in the absence of the candidate modulator identifies the candidate modulator as a modulator of the downstream activity of the SARS-CoV-2 S protein.

In another aspect, the disclosure features a method of identifying a modulator of a downstream activity of CNTN1, IL12RB1, or IL1RAPL2, the method comprising: (a) providing a candidate modulator; (b) contacting CNTN1, IL12RB1, or IL1RAPL2 with the SARS-CoV-2 S protein RBD in the presence or absence of the candidate modulator under conditions permitting the binding of CNTN1, IL12RB1, or IL1RAPL2 to the SARS-CoV-2 S protein RBD; and (c) measuring a downstream activity of CNTN1, IL12RB1, or IL1RAPL2, wherein a change in the downstream activity in the presence of the candidate modulator relative to the downstream activity in the absence of the candidate modulator identifies the candidate modulator as a modulator of the downstream activity of CNTN1, IL12RB1, or IL1RAPL2.

In some aspects, the increase or decrease in binding is at least 50%, as measured by surface plasmon resonance, biolayer interferometry, or an enzyme-linked immunosorbent assay (ELISA).

In some aspects, the modulator is an inhibitor of the downstream activity of the SARS-CoV-2 S protein or CNTN1, IL12RB1, or IL1RAPL2. In some aspects, the change in the downstream activity is a decrease in the amount, strength, or duration of the downstream activity.

In some aspects, the modulator is a small molecule, an antibody or antigen-binding fragment thereof, a peptide, a mimic, or an inhibitory nucleic acid. In some aspects, the inhibitory nucleic acid is an ASO or an siRNA.

In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody or antigen-binding fragment thereof binds the SARS-CoV-2 S protein RBD. In some aspects, the antibody or antigen-binding fragment thereof binds CNTN1, IL12RB1, or IL1RAPL2.

In some aspects, the downstream activity is infection of a cell by SARS-CoV-2. In some aspects, infection is decreased in the presence of the modulator. In some aspects, infection is decreased by at least 40%, as measured in a viral infection assay or a viral entry assay using SARS-CoV-2 S protein pseudotyped particles.

In some aspects, the modulator is an antibody or antigen-binding fragment thereof that binds the SARS-CoV-2 S protein RBD.

In some aspects, the modulator is an antibody or antigen-binding fragment thereof that binds CNTN1, IL12RB1, or IL1RAPL2.

In another aspect, the disclosure features an isolated modulator of the interaction between the SARS-CoV-2 S protein and CNTN1, IL12RB1, or IL1RAPL2, wherein the modulator causes a decrease in the binding of the SARS-CoV-2 S protein to CNTN1, IL12RB1, or IL1RAPL2 relative to binding in the absence of the modulator.

In another aspect, the disclosure features an isolated modulator of the downstream activity of the SARS-CoV-2 S protein or CNTN1, IL12RB1, or IL1RAPL2, wherein the modulator causes a change in the downstream activity of the SARS-CoV-2 S protein or CNTN1, IL12RB1, or IL1RAPL2 relative to downstream activity in the absence of the modulator.

In some aspects, the decrease in binding is at least 50%, as measured by surface plasmon resonance, biolayer interferometry, or an enzyme-linked immunosorbent assay (ELISA).

In some aspects, the modulator is an inhibitor of the downstream activity of the SARS-CoV-2 S protein or CNTN1, IL12RB1, or IL1RAPL2.

In some aspects, the change in the downstream activity is a decrease in the amount, strength, or duration of the downstream activity.

In some aspects, the modulator is a small molecule, an antibody or antigen-binding fragment thereof, a peptide, a mimic, or an inhibitory nucleic acid.

In some aspects, the inhibitory nucleic acid is an ASO or a siRNA.

In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody or antigen-binding fragment thereof binds the SARS-CoV-2 S protein RBD. In some aspects, the antibody or antigen-binding fragment thereof binds CNTN1, IL12RB1, or IL1RAPL2.

In some aspects, the antibody is a bispecific antibody. In some aspects, the bispecific antibody binds (a) ACE2 and CNTN1; (b) ACE2 and IL12RB1; or (c) ACE2 and IL1RAPL2.

In another aspect, the disclosure features use of a CNTN1 antagonist, an IL12RB1 antagonist, or an IL1RAPL2 antagonist in the manufacture of a medicament for treating an individual having a SARS-CoV-2 infection.

In another aspect, the disclosure features use of a CNTN1 antagonist, an IL12RB1 antagonist, or an IL1RAPL2 antagonist in the manufacture of a medicament for reducing SARS-CoV-2 attachment to a cell of an individual.

In some aspects, the medicament is adapted to be administered by contacting a cell of the individual with an effective amount of the CNTN1 antagonist, the IL12RB1 antagonist, or the IL1RAPL2 antagonist.

In another aspect, the disclosure features use of a CNTN1 antagonist, an IL12RB1 antagonist, or an IL1RAPL2 antagonist in the manufacture of a medicament for decreasing SARS-CoV-2 infection in an individual.

In some aspects, (a) the CNTN1 antagonist results in a decrease in the binding of CNTN1 and the SARS-CoV-2 spike (S) protein relative to binding of the two proteins in the absence of the antagonist; (b) the IL12RB1 antagonist results in a decrease in the binding of IL12RB1 and the SARS-CoV-2 S protein relative to binding of the two proteins in the absence of the antagonist; or (c) the IL1RAPL2 antagonist results in a decrease in the binding of IL1RAPL2 and the SARS-CoV-2 S protein relative to binding of the two proteins in the absence of the antagonist.

In some aspects, the CNTN1 antagonist, IL12RB1 antagonist, or IL1RAPL2 antagonist reduces the extent and/or severity of SARS-CoV-2 infection of the individual relative to infection in the absence of the CNTN1 antagonist, IL12RB1 antagonist, or IL1RAPL2 antagonist, respectively.

In some aspects, the CNTN1 antagonist, IL12RB1 antagonist, or IL1RAPL2 antagonist is a small molecule, an antibody or antigen-binding fragment thereof, a peptide, a mimic, or an inhibitory nucleic acid. In some aspects, the inhibitory nucleic acid is an antisense oligonucleotide (ASO) or a small interfering RNA (siRNA).

In some aspects, the CNTN1 antagonist, IL12RB1 antagonist, or IL1RAPL2 antagonist is a peptide.

In some aspects, the CNTN1 antagonist, IL12RB1 antagonist, or IL1RAPL2 antagonist is an antibody or antigen-binding fragment thereof.

In some aspects, the antibody or antigen-binding fragment thereof binds the SARS-CoV-2 S protein and inhibits its binding to CNTN1, IL12RB1, and/or IL1RAPL2.

In some aspects, the antibody or antigen-binding fragment thereof binds CNTN1, IL12RB1, or IL1RAPL2. In some aspects, the antibody or antigen-binding fragment thereof inhibits the binding of CNTN1, IL12RB1, or IL1RAPL2 to the SARS-CoV-2 S protein.

In some aspects, the antibody or antigen-binding fragment thereof inhibits the binding of CNTN1, Il12RB1, or IL1RAPL2 to the SARS-CoV-2 S protein RBD.

In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody is a bispecific antibody. In some aspects, the bispecific antibody binds (a) angiotensin-converting enzyme 2 (ACE2) and CNTN1; (b) ACE2 and IL12RB1; or (c) ACE2 and IL1RAPL2.

In another aspect, the disclosure features use of a CNTN1 antagonist or an IL1RAPL2 antagonist in the manufacture of a medicament for prophylaxis against secondary infection of nervous tissue in an individual having a SARS-CoV-2 infection.

In some aspects, (a) the CNTN1 antagonist results in a decrease in the binding of CNTN1 and the SARS-CoV-2 S protein relative to binding of the two proteins in the absence of the antagonist; or (b) the IL1RAPL2 antagonist results in a decrease in the binding of IL1RAPL2 and the SARS-CoV-2 S protein relative to binding of the two proteins in the absence of the antagonist.

In some aspects, the CNTN1 antagonist or IL1RAPL2 antagonist reduces the extent and/or severity of SARS-CoV-2 infection of nervous tissue in the individual relative to infection in the absence of the CNTN1 antagonist or IL1RAPL2 antagonist, respectively.

In some aspects, the CNTN1 antagonist or IL1RAPL2 antagonist is a small molecule, an antibody or antigen-binding fragment thereof, a peptide, a mimic, or an inhibitory nucleic acid.

In some aspects, the inhibitory nucleic acid is an ASO or a siRNA.

In some aspects, the CNTN1 antagonist or IL1RAPL2 antagonist is a peptide.

In some aspects, the CNTN1 antagonist or IL1RAPL2 antagonist is an antibody or antigen-binding fragment thereof.

In some aspects, the antibody or antigen-binding fragment thereof binds the SARS-CoV-2 S protein and inhibits its binding to CNTN1 and/or IL1RAPL2.

In some aspects, the antibody or antigen-binding fragment thereof binds CNTN1 or IL1RAPL2. In some aspects, the antibody or antigen-binding fragment thereof inhibits the binding of CNTN1 or IL1RAPL2 to the SARS-CoV-2 S protein. In some aspects, the antibody or antigen-binding fragment thereof inhibits the binding of CNTN1 or IL1RAPL2 to the SARS-CoV-2 S protein RBD.

In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody is a bispecific antibody. In some aspects, the bispecific antibody binds (a) ACE2 and CNTN1, (b) ACE2 and IL1RAPL2, or (c) CNTN1 and IL1RAPL2.

In another aspect, the disclosure features use of an IL12RB1 antagonist in the manufacture of a medicament for prophylaxis against secondary infection of immune cells and/or lymphoid tissue in an individual having a SARS-CoV-2 infection.

In some aspects, the IL12RB1 antagonist results in a decrease in the binding of IL12RB1 and the SARS-CoV-2 S protein relative to binding of the two proteins in the absence of the antagonist.

In some aspects, the IL12RB1 antagonist reduces the extent and/or severity of SARS-CoV-2 infection of immune cells and/or lymphoid tissue in the individual relative to infection in the absence of the IL12RB1 antagonist.

In some aspects, the IL12RB1 antagonist is a small molecule, an antibody or antigen-binding fragment thereof, a peptide, a mimic, or an inhibitory nucleic acid. In some aspects, the inhibitory nucleic acid is an ASO or a siRNA.

In some aspects, the IL12RB1 antagonist is a peptide.

In some aspects, the IL12RB1 antagonist is an antibody or antigen-binding fragment thereof.

In some aspects, the antibody or antigen-binding fragment thereof binds the SARS-CoV-2 S protein and inhibits its binding to IL12RB1.

In some aspects, the antibody or antigen-binding fragment thereof binds IL12RB1. In some aspects, the antibody or antigen-binding fragment thereof inhibits the binding of IL12RB1 to the SARS-CoV-2 S protein. In some aspects, the antibody or antigen-binding fragment thereof inhibits the binding of IL12RB1 to the SARS-CoV-2 S protein RBD.

In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody is a bispecific antibody. In some aspects, the bispecific antibody binds ACE2 and IL12RB1.

In another aspect, the disclosure features use of a CNTN1 antagonist or an IL12RB1 antagonist in the manufacture of a medicament for prophylaxis against secondary infection of the lungs in an individual having a SARS-CoV-2 infection.

In some aspects, (a) the CNTN1 antagonist results in a decrease in the binding of CNTN1 and the SARS-CoV-2 S protein relative to binding of the two proteins in the absence of the antagonist; or (b) the IL12RB1 antagonist results in a decrease in the binding of IL12RB1 and the SARS-CoV-2 S protein relative to binding of the two proteins in the absence of the antagonist.

In some aspects, the CNTN1 antagonist or IL12RB1 antagonist reduces the extent and/or severity of SARS-CoV-2 infection of the lungs in the individual relative to infection in the absence of the CNTN1 antagonist or IL12RB1 antagonist, respectively.

In some aspects, the CNTN1 antagonist or IL12RB1 antagonist is a small molecule, an antibody or antigen-binding fragment thereof, a peptide, a mimic, or an inhibitory nucleic acid. In some aspects, the inhibitory nucleic acid is an ASO or a siRNA.

In some aspects, the CNTN1 antagonist or IL12RB1 antagonist is a peptide.

In some aspects, the CNTN1 antagonist or IL12RB1 antagonist is an antibody or antigen-binding fragment thereof.

In some aspects, the antibody or antigen-binding fragment thereof binds the SARS-CoV-2 S protein and inhibits its binding to CNTN1 and/or IL12RB1.

In some aspects, the antibody or antigen-binding fragment thereof binds CNTN1 or IL12RB1. In some aspects, the antibody or antigen-binding fragment thereof inhibits the binding of CNTN1 or IL12RB1 to the SARS-CoV-2 S protein. In some aspects, the antibody or antigen-binding fragment thereof inhibits the binding of CNTN1 or IL12RB1 to the SARS-CoV-2 S protein RBD.

In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody is a bispecific antibody. In some aspects, the bispecific antibody binds (a) ACE2 and CNTN1, (b) ACE2 and IL12RB1, or (c) CNTN1 and IL12RB1.

In some aspects, the individual has COVID-19. In some aspects, the individual has COVID-19 pneumonia or acute respiratory distress syndrome (ARDS).

In some aspects, the medicament is adapted to be administered to the individual with at least one additional therapy. In some aspects, the medicament is adapted to be administered to the individual prior to, concurrently with, or after the at least one additional therapy.

In some aspects, the at least one additional therapy is an ACE2 antagonist.

In some aspects, the at least one additional therapy is a NRP2 antagonist.

In some aspects, the at least one additional therapy is a supportive care therapy, an anti-viral therapy, or a corticosteroid therapy.

In some aspects, the supportive care therapy comprises oxygen therapy.

In some aspects, the anti-viral therapy comprises alpha-interferon, lopinavir, ritonavir, lopinavir/ritonavir, remdesivir, ribavirin, hydroxychloroquine, chloroquine, umifenovir, favipiravir, or a combination thereof.

In some aspects, the corticosteroid therapy comprises prednisone, prednisolone, methylprednisolone, methylprednisolone sodium succinate, dexamethasone, dexamethasone triamcinolone, hydrocortisone, betamethasone, or a combination thereof.

In some aspects, the corticosteroid therapy is a low-dose corticosteroid therapy.

In some aspects, treatment achieves a greater improvement in clinical outcome compared to SOC.

In some aspects, the clinical outcome is TTCI defined as a NEWS2 of ≤2 maintained for 24 hours.

In some aspects, the clinical outcome is incidence of mechanical ventilation.

In some aspects, the clinical outcome is incidence of ICU stay.

In some aspects, the clinical outcome is duration of ICU stay.

In some aspects, the clinical outcome is time to clinical failure defined as the time to death, mechanical ventilation, ICU admission, or withdrawal, whichever occurs first.

In some aspects, the clinical outcome is time to hospital discharge; or ready for discharge as evidenced by normal body temperature and respiratory rate, and stable oxygen saturation on ambient air or ≤2 L supplemental oxygen.

In some aspects, the clinical outcome is duration of supplemental oxygen.

In some aspects, the clinical outcome is selected from the group consisting of incidence of vasopressor use, duration of vasopressor use, incidence of ECMO, incidence of starting dialysis, SARS-CoV-2 viral load on Day 15 or day of hospital discharge (whichever occurs first), and proportion of individuals with secondary bacterial infections.

In some aspects, treatment is associated with an acceptable safety outcome compared with SOC.

In some aspects, the safety outcome is selected from the group consisting of: incidence and severity of adverse events; incidence and severity of adverse events with severity determined according to NCI CTCAE v5.0; change from baseline in targeted vital signs; and change from baseline in targeted clinical laboratory test results.

In some aspects, the SOC comprises supportive care, administration of one or more anti-viral agents, and/or administration of one or more low-dose corticosteroids.

In some aspects, the individual is a human.

In another aspect, the disclosure features a CNTN1 antagonist, an IL12RB1 antagonist, or an IL1RAPL2 antagonist for use in treating an individual having a SARS-CoV-2 infection.

In another aspect, the disclosure features a CNTN1 antagonist, an IL12RB1 antagonist, or an IL1RAPL2 antagonist for use in reducing SARS-CoV-2 attachment to a cell of an individual.

In some aspects, the CNTN1 antagonist, IL12RB1 antagonist, or IL1RAPL2 antagonist is to be administered by contacting the cell of the individual with an effective amount of the CNTN1 antagonist, an IL12RB1 antagonist, or IL1RAPL2 antagonist.

In another aspect, the disclosure features a CNTN1 antagonist, an IL12RB1 antagonist, or an IL1RAPL2 antagonist for use in decreasing SARS-CoV-2 infection in an individual.

In some aspects, (a) the CNTN1 antagonist results in a decrease in the binding of CNTN1 and the SARS-CoV-2 spike (S) protein relative to binding of the two proteins in the absence of the antagonist; (b) the IL12RB1 antagonist results in a decrease in the binding of IL12RB1 and the SARS-CoV-2 S protein relative to binding of the two proteins in the absence of the antagonist; or (c) the IL1RAPL2 antagonist results in a decrease in the binding of IL1RAPL2 and the SARS-CoV-2 S protein relative to binding of the two proteins in the absence of the antagonist.

In some aspects, the CNTN1 antagonist, IL12RB1 antagonist, or IL1RAPL2 antagonist reduces the extent and/or severity of SARS-CoV-2 infection of the individual relative to infection in the absence of the CNTN1 antagonist, IL12RB1 antagonist, or IL1RAPL2 antagonist, respectively.

In some aspects, the CNTN1 antagonist, IL12RB1 antagonist, or IL1RAPL2 antagonist is a small molecule, an antibody or antigen-binding fragment thereof, a peptide, a mimic, or an inhibitory nucleic acid. In some aspects, the inhibitory nucleic acid is an antisense oligonucleotide (ASO) or a small interfering RNA (siRNA).

In some aspects, the CNTN1 antagonist, IL12RB1 antagonist, or IL1RAPL2 antagonist is a peptide.

In some aspects, the CNTN1 antagonist, IL12RB1 antagonist, or IL1RAPL2 antagonist is an antibody or antigen-binding fragment thereof.

In some aspects, the antibody or antigen-binding fragment thereof binds the SARS-CoV-2 S protein and inhibits its binding to CNTN1, IL12RB1, and/or IL1RAPL2.

In some aspects, the antibody or antigen-binding fragment thereof binds CNTN1, IL12RB1, or IL1RAPL2. In some aspects, the antibody or antigen-binding fragment thereof inhibits the binding of CNTN1, IL12RB1, or IL1RAPL2 to the SARS-CoV-2 S protein. In some aspects, the antibody or antigen-binding fragment thereof inhibits the binding of CNTN1, Il12RB1, or IL1RAPL2 to the SARS-CoV-2 S protein receptor binding domain (RBD).

In some aspects, the antigen-binding fragment is a bis-Fab, an Fv, a Fab, a Fab'-SH, a F(ab')2, a diabody, a linear antibody, an scFv, an scFab, a VH domain, or a VHH domain.

In some aspects, the antibody is a bispecific antibody. In some aspects, the bispecific antibody binds (a) angiotensin-converting enzyme 2 (ACE2) and CNTN1; (b) ACE2 and IL12RB1; or (c) ACE2 and
IL1RAPL2.

In another aspect, the disclosure features a CNTN1 antagonist or an IL1RAPL2 antagonist for use in prophylaxis against secondary infection of nervous tissue in an individual having a SARS-CoV-2 infection.

In some aspects, (a) the CNTN1 antagonist results in a decrease in the binding of CNTN1 and the SARS-CoV-2 S protein relative to binding of the two proteins in the absence of the antagonist; or (b) the IL1RAPL2 antagonist results in a decrease in the binding of IL1RAPL2 and the SARS-CoV-2 S protein relative to binding of the two proteins in the absence of the antagonist.

In some aspects, the CNTN1 antagonist or IL1RAPL2 antagonist reduces the extent and/or severity of SARS-CoV-2 infection of nervous tissue in the individual relative to infection in the absence of the CNTN1 antagonist or IL1RAPL2 antagonist, respectively.

In some aspects, the CNTN1 antagonist or IL1RAPL2 antagonist is a small molecule, an antibody or antigen-binding fragment thereof, a peptide, a mimic, or an inhibitory nucleic acid. In some aspects, the inhibitory nucleic acid is an ASO or a siRNA.

In some aspects, the CNTN1 antagonist or IL1RAPL2 antagonist is a peptide.

In some aspects, the CNTN1 antagonist or IL1RAPL2 antagonist is an antibody or antigen-binding fragment thereof.

In some aspects, the antibody or antigen-binding fragment thereof binds the SARS-CoV-2 S protein and inhibits its binding to CNTN1 and/or IL1RAPL2.

In some aspects, the antibody or antigen-binding fragment thereof binds CNTN1 or IL1RAPL2. In some aspects, the antibody or antigen-binding fragment thereof inhibits the binding of CNTN1 or IL1RAPL2 to the SARS-CoV-2 S protein. In some aspects, the antibody or antigen-binding fragment thereof inhibits the binding of CNTN1 or IL1RAPL2 to the SARS-CoV-2 S protein RBD.

In some aspects, the antigen-binding fragment is a bis-Fab, an Fv, a Fab, a Fab'-SH, a F(ab')2, a diabody, a linear antibody, an scFv, an scFab, a VH domain, or a VHH domain.

In some aspects, the antibody is a bispecific antibody. In some aspects, the bispecific antibody binds (a) ACE2 and CNTN1, (b) ACE2 and IL1RAPL2, or (c) CNTN1 and IL1RAPL2.

In another aspect, the disclosure features an IL12RB1 antagonist for use in prophylaxis against secondary infection of immune cells and/or lymphoid tissue in an individual having a SARS-CoV-2 infection.

In some aspects, the IL12RB1 antagonist results in a decrease in the binding of IL12RB1 and the SARS-CoV-2 S protein relative to binding of the two proteins in the absence of the antagonist.

In some aspects, the IL12RB1 antagonist reduces the extent and/or severity of SARS-CoV-2 infection of immune cells and/or lymphoid tissue in the individual relative to infection in the absence of the IL12RB1 antagonist.

In some aspects, the IL12RB1 antagonist is a small molecule, an antibody or antigen-binding fragment thereof, a peptide, a mimic, or an inhibitory nucleic acid. In some aspects, the inhibitory nucleic acid is an ASO or a siRNA.

In some aspects, the IL12RB1 antagonist is a peptide.

In some aspects, the IL12RB1 antagonist is an antibody or antigen-binding fragment thereof.

In some aspects, the antibody or antigen-binding fragment thereof binds the SARS-CoV-2 S protein and inhibits its binding to IL12RB1.

In some aspects, the antibody or antigen-binding fragment thereof binds IL12RB1. In some aspects, the antibody or antigen-binding fragment thereof inhibits the binding of IL12RB1 to the SARS-CoV-2 S protein. In some aspects, the antibody or antigen-binding fragment thereof inhibits the binding of IL12RB1 to the SARS-CoV-2 S protein RBD.

In some aspects, the antigen-binding fragment is a bis-Fab, an Fv, a Fab, a Fab'-SH, a F(ab')2, a diabody, a linear antibody, an scFv, an scFab, a VH domain, or a VHH domain.

In some aspects, the antibody is a bispecific antibody. In some aspects, the bispecific antibody binds ACE2 and IL12RB1.

In another aspect, the disclosure features a CNTN1 antagonist or an IL12RB1 antagonist for use in prophylaxis against secondary infection of the lungs in an individual having a SARS-CoV-2 infection.

In some aspects, (a) the CNTN1 antagonist results in a decrease in the binding of CNTN1 and the SARS-CoV-2 S protein relative to binding of the two proteins in the absence of the antagonist; or (b) the IL12RB1 antagonist results in a decrease in the binding of IL12RB1 and the SARS-CoV-2 S protein relative to binding of the two proteins in the absence of the antagonist.

In some aspects, the CNTN1 antagonist or IL12RB1 antagonist reduces the extent and/or severity of SARS-CoV-2 infection of the lungs in the individual relative to infection in the absence of the CNTN1 antagonist or IL12RB1 antagonist, respectively.

In some aspects, the CNTN1 antagonist or IL12RB1 antagonist is a small molecule, an antibody or antigen-binding fragment thereof, a peptide, a mimic, or an inhibitory nucleic acid. In some aspects, the inhibitory nucleic acid is an ASO or a siRNA.

In some aspects, the CNTN1 antagonist or IL12RB1 antagonist is a peptide.

In some aspects, the CNTN1 antagonist or IL12RB1 antagonist is an antibody or antigen-binding fragment thereof.

In some aspects, the antibody or antigen-binding fragment thereof binds the SARS-CoV-2 S protein and inhibits its binding to CNTN1 and/or IL12RB1.

In some aspects, the antibody or antigen-binding fragment thereof binds CNTN1 or IL12RB1. In some aspects, the antibody or antigen-binding fragment thereof inhibits the binding of CNTN1 or IL12RB1 to the SARS-CoV-2 S protein. In some aspects, the antibody or antigen-binding fragment thereof inhibits the binding of CNTN1 or IL12RB1 to the SARS-CoV-2 S protein RBD.

In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody is a bispecific antibody.

In some aspects, the bispecific antibody binds (a) ACE2 and CNTN1, (b) ACE2 and IL12RB1, or (c) CNTN1 and IL12RB1.

In some aspects, the individual has COVID-19.

In some aspects, the individual has COVID-19 pneumonia or acute respiratory distress syndrome (ARDS).

In some aspects, at least one additional therapy is to be administered to the individual.

In some aspects, the CNTN1 antagonist, IL12RB1 antagonist, or IL1RAPL2 antagonist is to be administered to the individual prior to, concurrently with, or after the at least one additional therapy.

In some aspects, the at least one additional therapy is an ACE2 antagonist.

In some aspects, the at least one additional therapy is a NRP2 antagonist.

In some aspects, the at least one additional therapy is a supportive care therapy, an anti-viral therapy, or a corticosteroid therapy.

In some aspects, the supportive care therapy comprises oxygen therapy.

In some aspects, the anti-viral therapy comprises alpha-interferon, lopinavir, ritonavir, lopinavir/ritonavir, remdesivir, ribavirin, hydroxychloroquine, chloroquine, umifenovir, favipiravir, or a combination thereof.

In some aspects, the corticosteroid therapy comprises prednisone, prednisolone, methylprednisolone, methylprednisolone sodium succinate, dexamethasone, dexamethasone triamcinolone, hydrocortisone, betamethasone, or a combination thereof. In some aspects, the corticosteroid therapy is a low-dose corticosteroid therapy.

In some aspects, the use achieves a greater improvement in clinical outcome compared to SOC.

In some aspects, the clinical outcome is TTCI defined as a NEWS2 of ≤2 maintained for 24 hours.

In some aspects, the clinical outcome is incidence of mechanical ventilation.

In some aspects, the clinical outcome is incidence of ICU stay.

In some aspects, the clinical outcome is duration of ICU stay.

In some aspects, the clinical outcome is time to clinical failure defined as the time to death, mechanical ventilation, ICU admission, or withdrawal, whichever occurs first.

In some aspects, the clinical outcome is time to hospital discharge; or ready for discharge as evidenced by normal body temperature and respiratory rate, and stable oxygen saturation on ambient air or ≤2 L supplemental oxygen.

In some aspects, the clinical outcome is duration of supplemental oxygen.

In some aspects, the clinical outcome is selected from the group consisting of incidence of vasopressor use, duration of vasopressor use, incidence of ECMO, incidence of starting dialysis, SARS-CoV-2 viral load on Day 15 or day of hospital discharge (whichever occurs first), and proportion of individuals with secondary bacterial infections.

In some aspects, the use is associated with an acceptable safety outcome compared with SOC.

In some aspects, the safety outcome is selected from the group consisting of: incidence and severity of adverse events; incidence and severity of adverse events with severity determined according to NCI CTCAE v5.0; change from baseline in targeted vital signs; and change from baseline in targeted clinical laboratory test results.

In some aspects, the SOC comprises supportive care, administration of one or more anti-viral agents, and/or administration of one or more low-dose corticosteroids.

In some aspects, the individual is a human.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2F is a set of representative immunofluorescence photomicrographs showing the SARS-CoV-1 spike trimer (Cov-1 Trimer), expressed as a fluorescently labeled tetramer, bound to the surface of cells expressing full-length ACE2, full-length IL12RB1, CNTN1 expressed as an ectodomain fused to gD-GPI, full-length IL1RAPL2, and full-length NRP2. Untransfected cells are shown as a control. Cells were contacted with the RBD tetramer at a 25 nM concentration. Red: RBD tetramer. Blue: nuclei. Scale bar=50 μM.

FIG. 3E is a set of violin plots showing normalized expression levels of ACE2, CNTN1, NRP2 and IL12RB1 by viral load (negative (healthy individuals), low, medium, or high) in nasopharynx from healthy individuals and COVID-19 patients (n=430 positive, 54 negative). Each dot represents an individual sample. Statistical significance between low, medium and high viral load is calculated by Mann Whitney U test, *p<0.05, p<0.01, *p<0.001. NS, Not significant. RNAseq data were obtained from GSE152075.

FIG. 3I is a set of violin plots showing expression of CNTN1 in different cell clusters from brain parenchyma (top panel) and a set of split violin plots showing the differential gene expression of CNTN1 between non-viral and COVID-19 infected individuals in each cell type collected from brain parenchyma (bottom panel), *p<0.05, p<0.01, *p<0.001, NS, Not significant.

shown in green). Nuclei are represented in blue. Images show RBD tetramer binding at 50 nM concentration. Scale bar=50 μm.

Figure 7A:
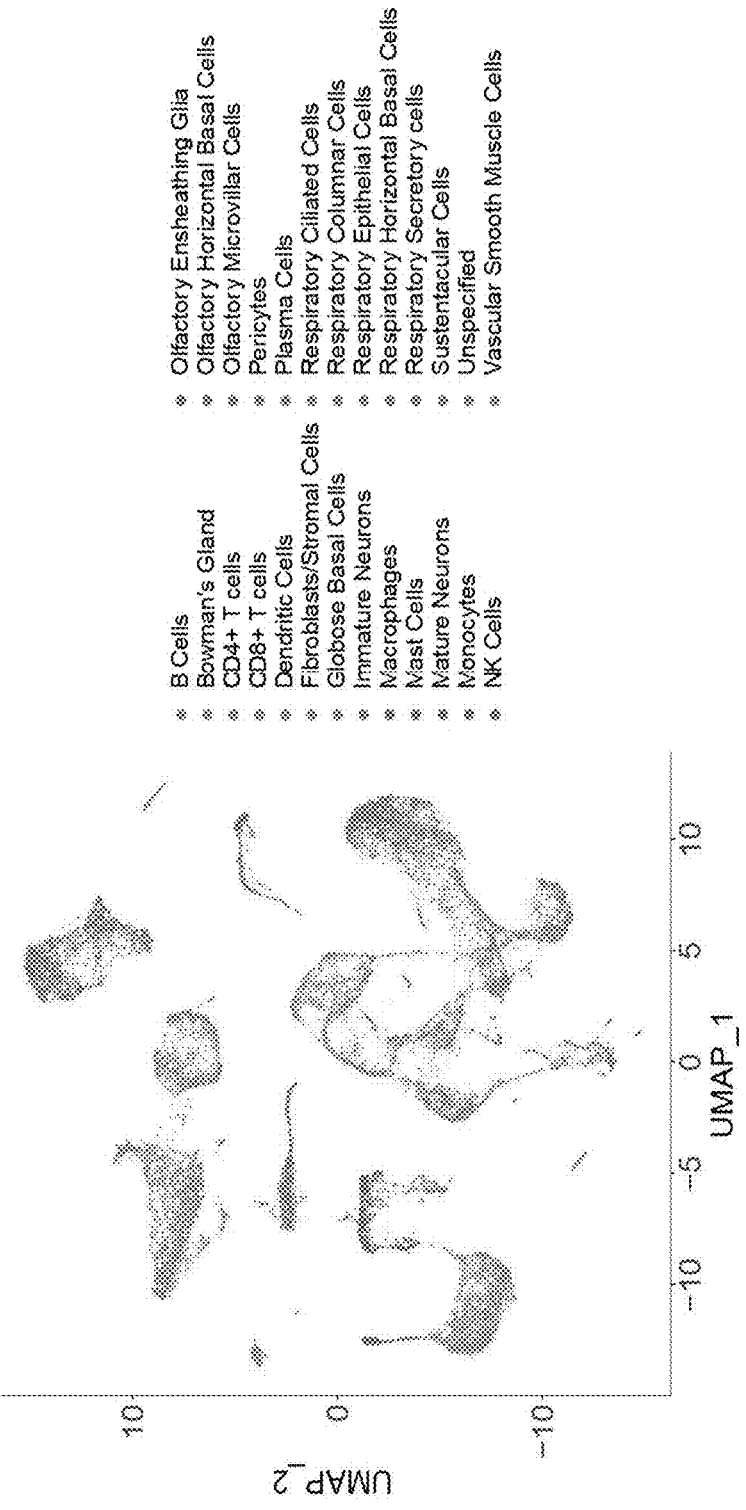

FIG. 7A is a Uniform Manifold Approximation and Projection (UMAP) dimensionality reduction plot showing gene expression data from 28,726 combined olfactory and respiratory mucosal cells from n=4 individuals. The cell cluster phenotypes are noted in the color key legend. scRNAseq data were obtained from GSE139522.

Figures 7B, 7C:
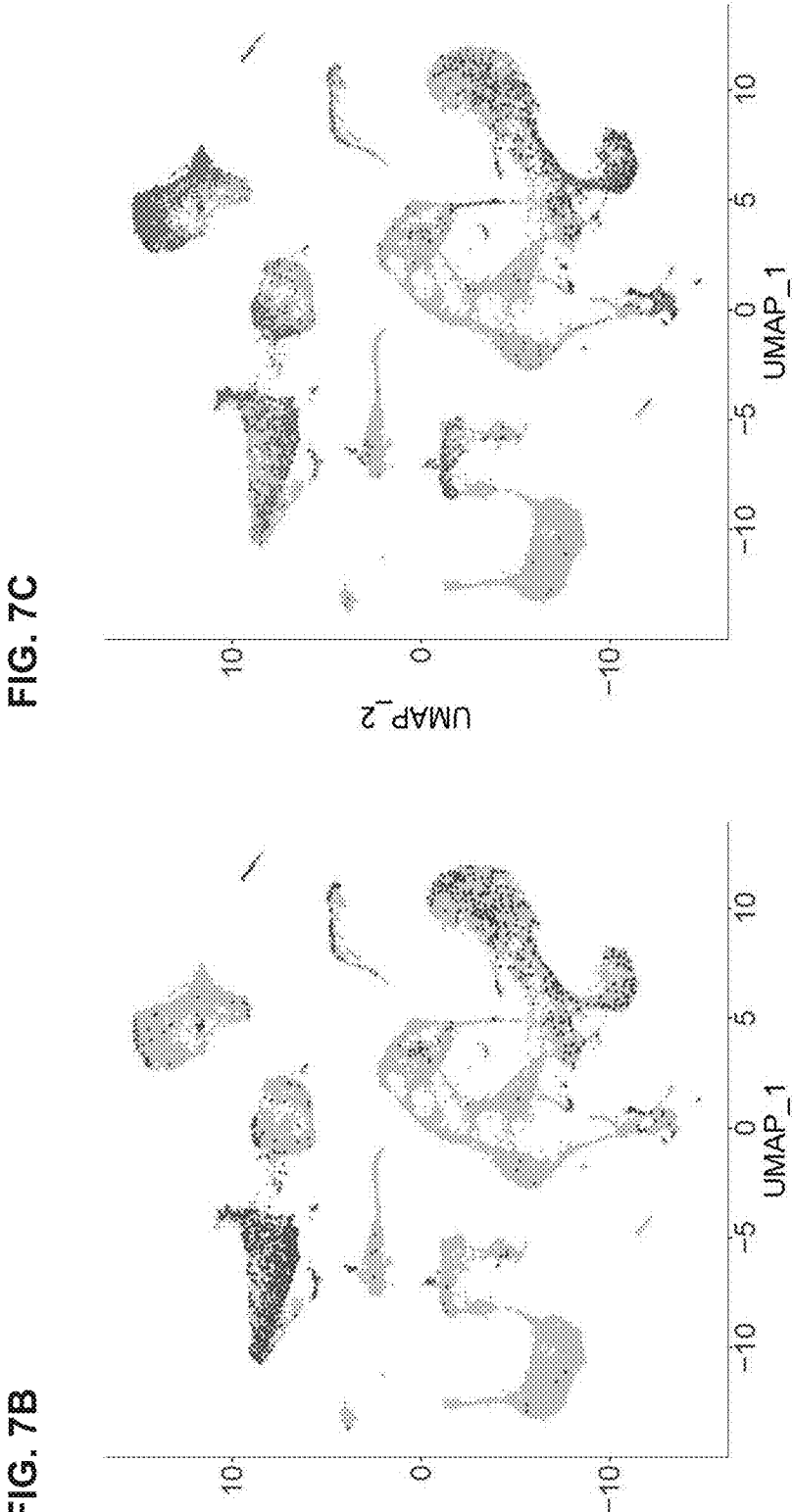

FIG. 7B is a UMAP dimensionality reduction plot showing gene expression of ACE2 (blue) and CNTN1 (red) in the scRNAseq data set of FIG. 7A.

FIG. 7C is a UMAP dimensionality reduction plot showing gene expression of ACE2 (blue) and NRP2 (green) in the scRNAseq data set of FIG. 7A.

Figure 7E:
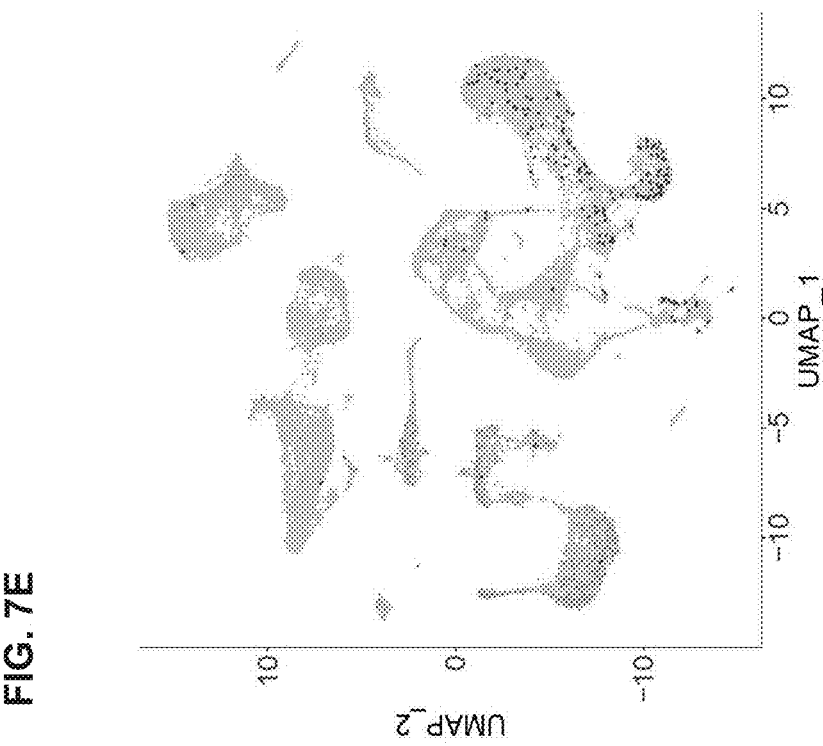
Figure 7D:
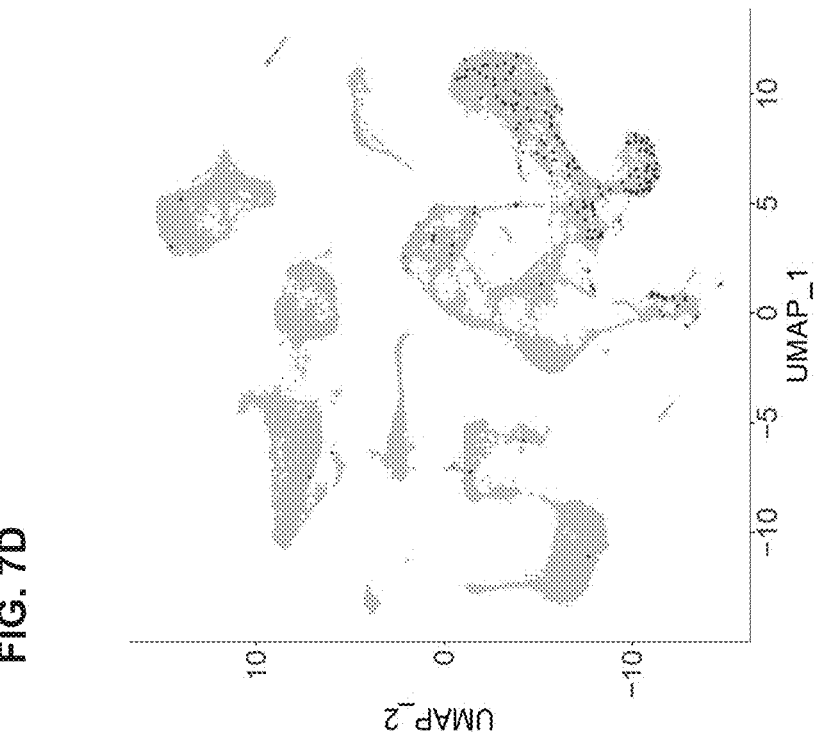

FIG. 7D is a UMAP dimensionality reduction plot showing gene expression of ACE2 (blue) and IL12RB1 (magenta) in the scRNAseq data set of FIG. 7A.

FIG. 7E is a UMAP dimensionality reduction plot showing gene expression of ACE2 (blue) and IL1RAPL2 (orange) in the scRNAseq data set of FIG. 7A.

Figure 7F:
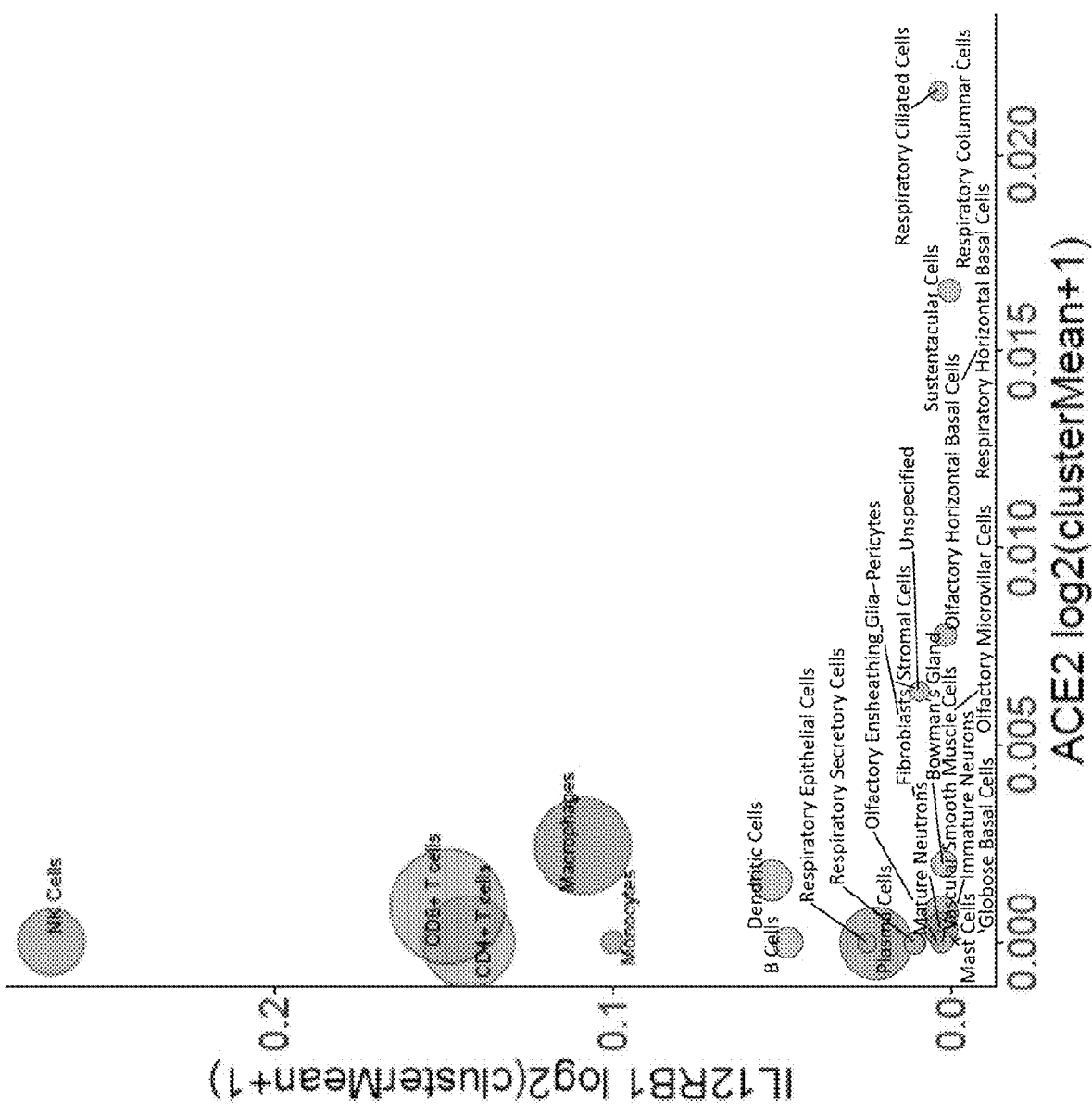

FIG. 7F is a bubble plot showing the expression levels of ACE2 and IL12RB1 in the indicated cell types. N=26. Size of bubbles represents the number of cells expressing the receptors. Size of bubbles represents the number of cells expressing the spike protein receptors scRNAsed data were obtained from GSE139522.

Figure 7G:
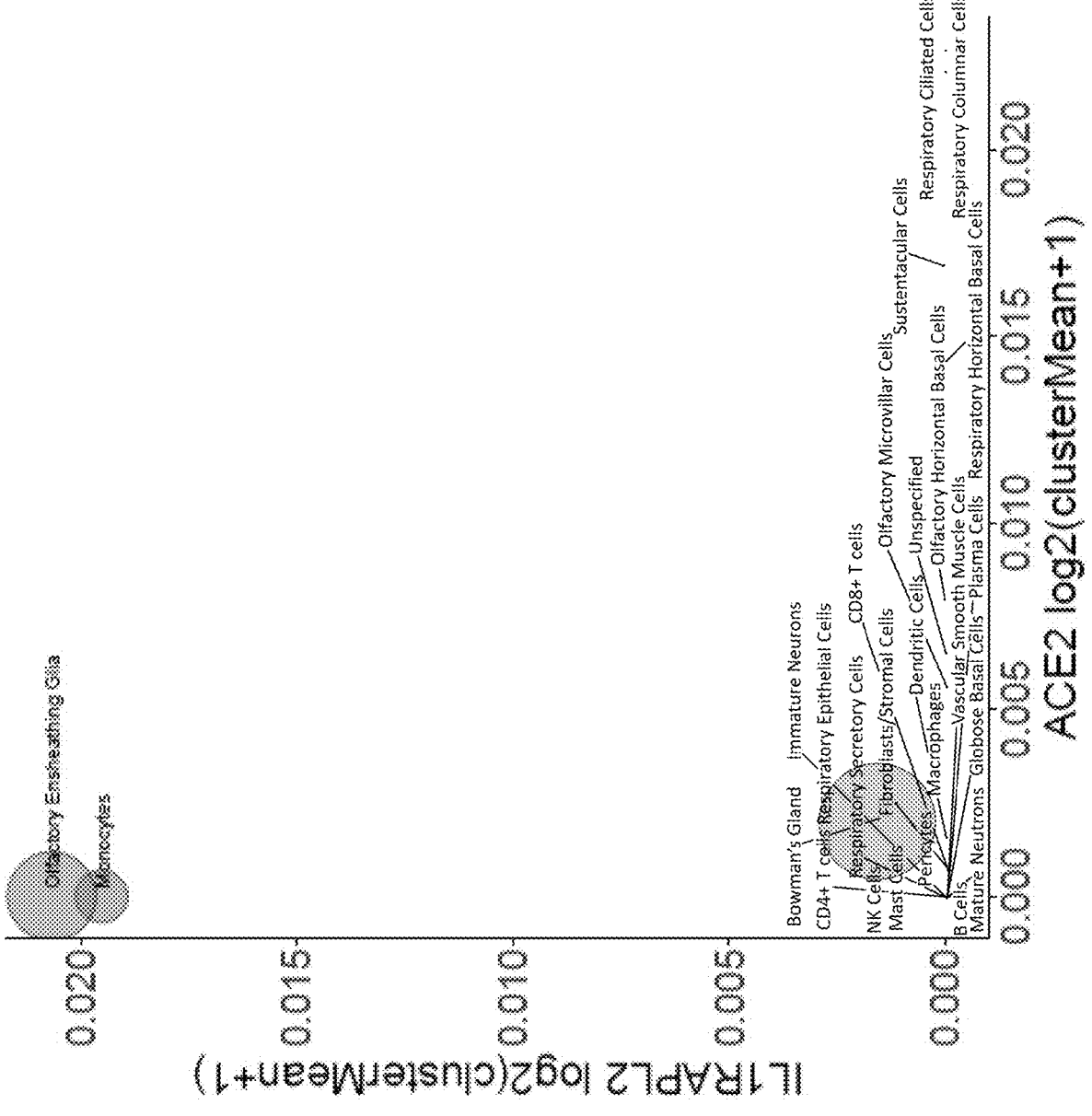

FIG. 7G is a bubble plot showing the expression levels of ACE2 and IL1RAPL2 in the indicated cell types. N=26. Size of bubbles represents the number of cells expressing the receptors. Size of bubbles represents the number of cells expressing the spike protein recepters scRNAseq data were obtained from GSE139522.

Figure 8E:
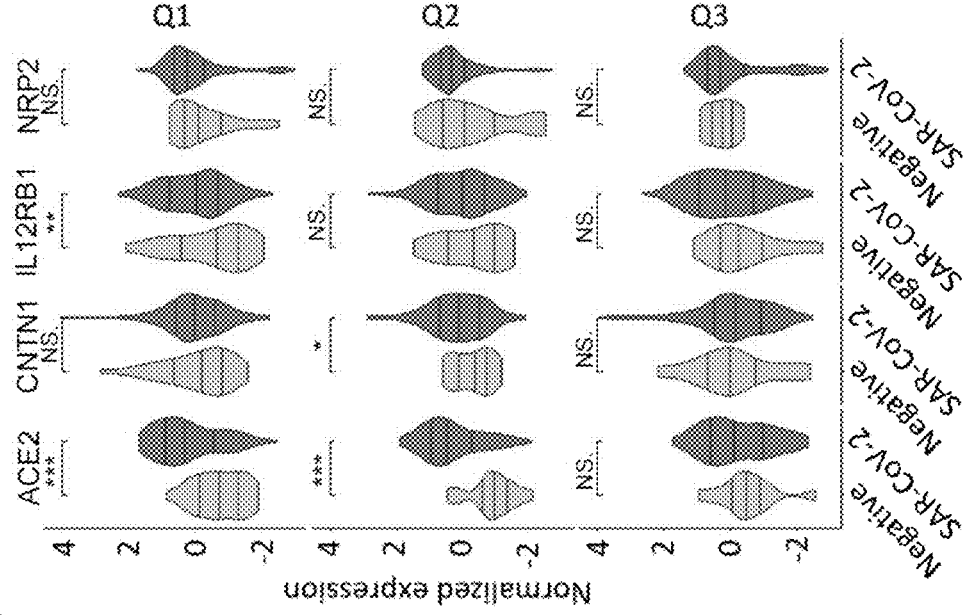
Figure 8A:
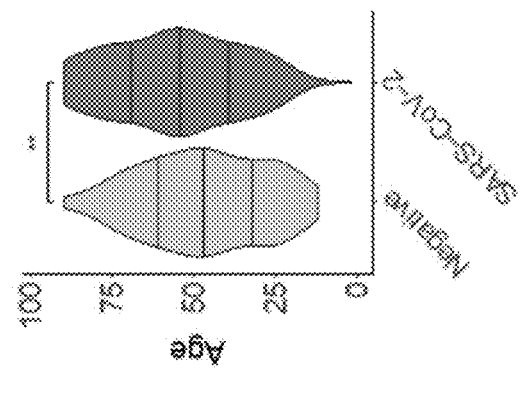

FIG. 8A is a set of violin plots showing the age of individuals having a SARS-CoV-2 infection (430 individuals) or who are negative for SARS-CoV-2 (54 individuals). Each dot represents an individual sample. Statistical significance is calculated by Mann Whitney U test, **p<0.01.

FIG. 8B is a set of violin plots showing the expression levels of ACE2, CNTN1, IL12RB1, IL1RAPL2, and NRP2 in SARS-CoV-2 positive and negative samples stratified by tertiles of ages. 01: ages 2-45; 02: ages 46-64; 03: ages 65-90+. Each dot represents an individual sample. Statistical significance is calculated by Mann Whitney U test, *p<0.05, ***p<0.001, NS, Not significant. RNAseq data were obtained from GSE152075.

Figure 9A:
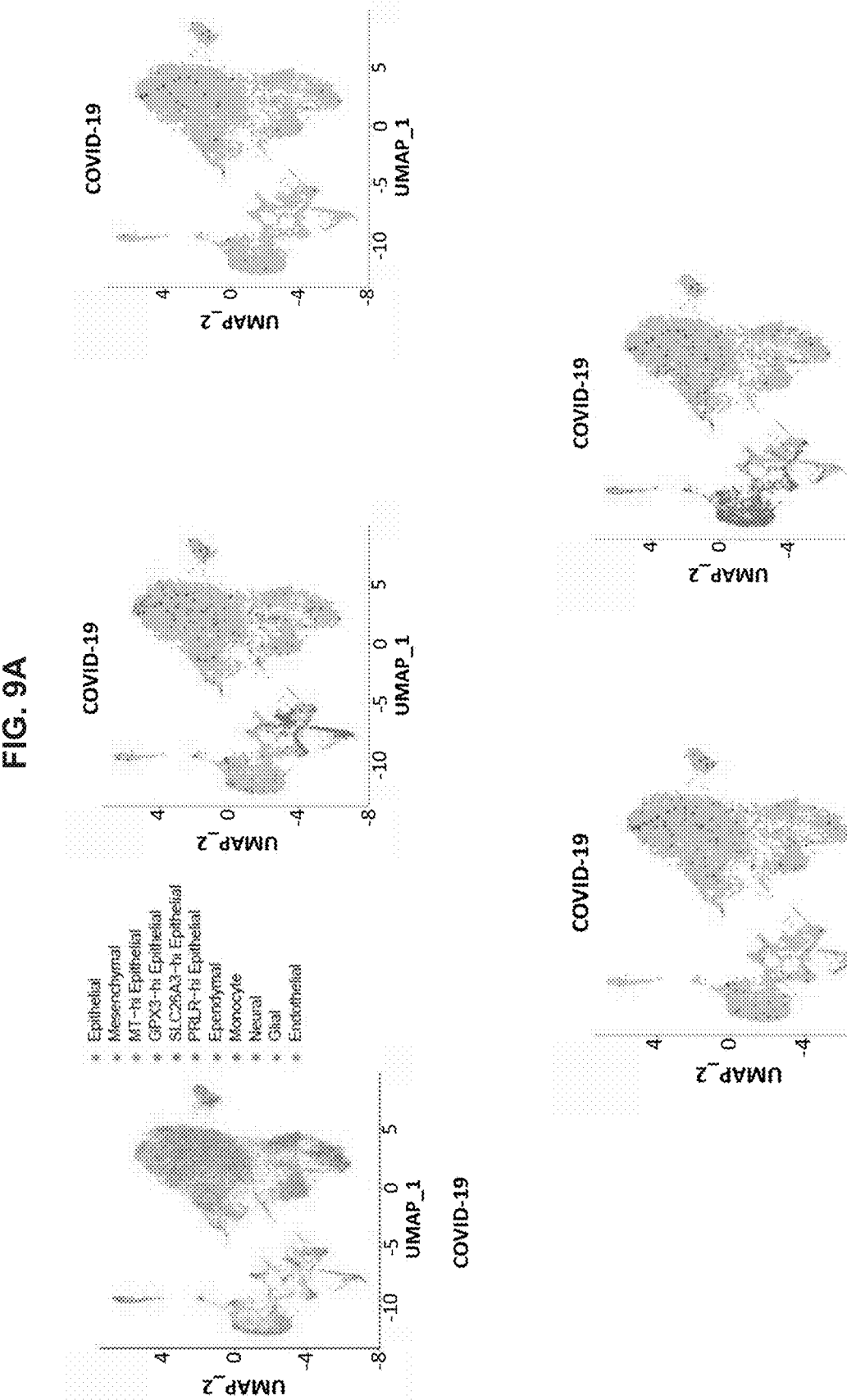

FIG. 9A is a set of UMAP dimensionality reduction plots showing gene expression data from 24,072 nuclei across 7 cell types in the choroid plexus. Single nucleus RNAseq data were obtained from Yang et al., *bioRxiv*, doi.org/10.1101/2020.10.22, 2020. The cell cluster phenotypes are noted in the color key legend. UMAPS of ACE2 (blue) and (top to bottom) CNTN1, NRP2, IL12RB1 and IL1RAPL2 from choroid plexus are shown.

FIG. 9B is a set of UMAP dimensionality reduction plots showing gene expression data from 23,626 nuclei across 8 cell types in the cortex parenchyma. Single nucleus RNAseq data were obtained from Yang et al., *bioRxiv*, doi.org/10.1101/2020.10.22, 2020. The cell cluster phenotypes are noted in the color key legend. UMAPS of ACE2 (blue) and (top to bottom) CNTN1, NRP2, IL12RB1 and IL1RAPL2 from cortex parenchyma are shown.

Figure 9C:
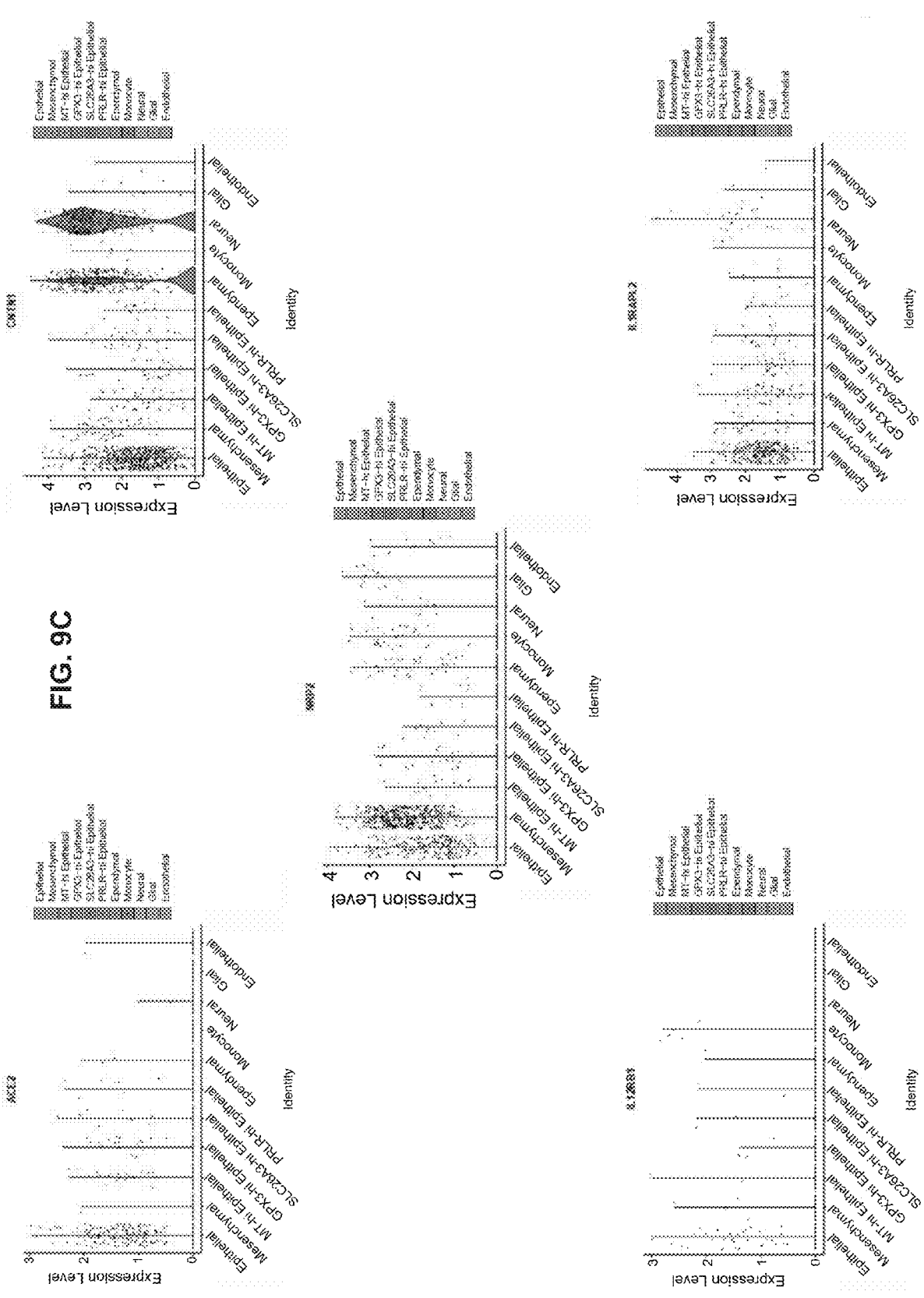

FIG. 9C is a set of violin plots showing expression levels of (top to bottom) ACE2, NRP2, CNTN1, IL12RB1 and IL1RAPL2 in different cell dusters from the indicated choroid plexus tissues.

Figure 9D:
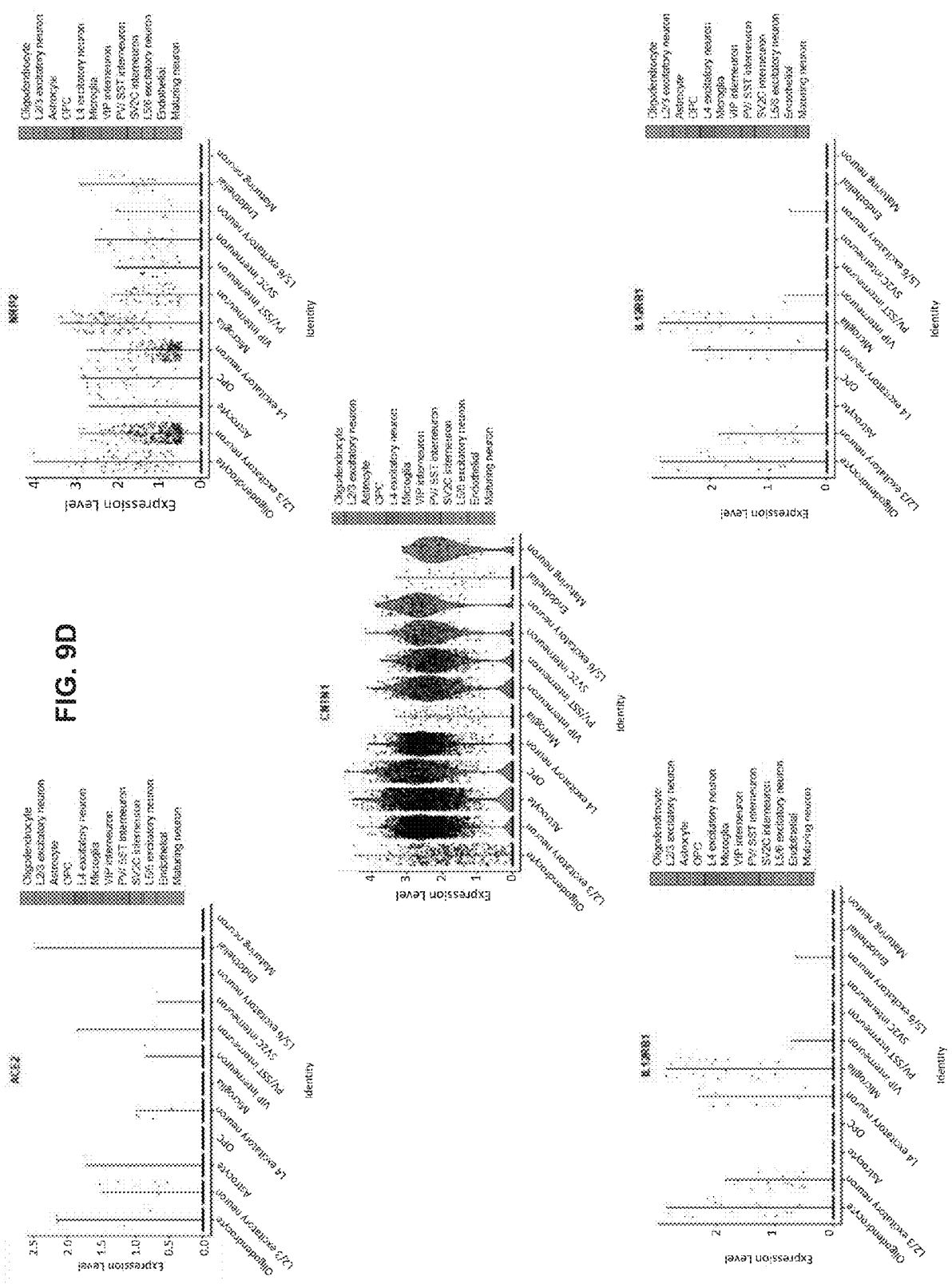

FIG. 9D is a set of violin plots showing expression levels of (top to bottom) ACE2, NRP2, CNTN1, IL12RB1 and IL1RAPL2 in different cell dusters from the indicated cortex parenchyma tissues.

Figure 10A:
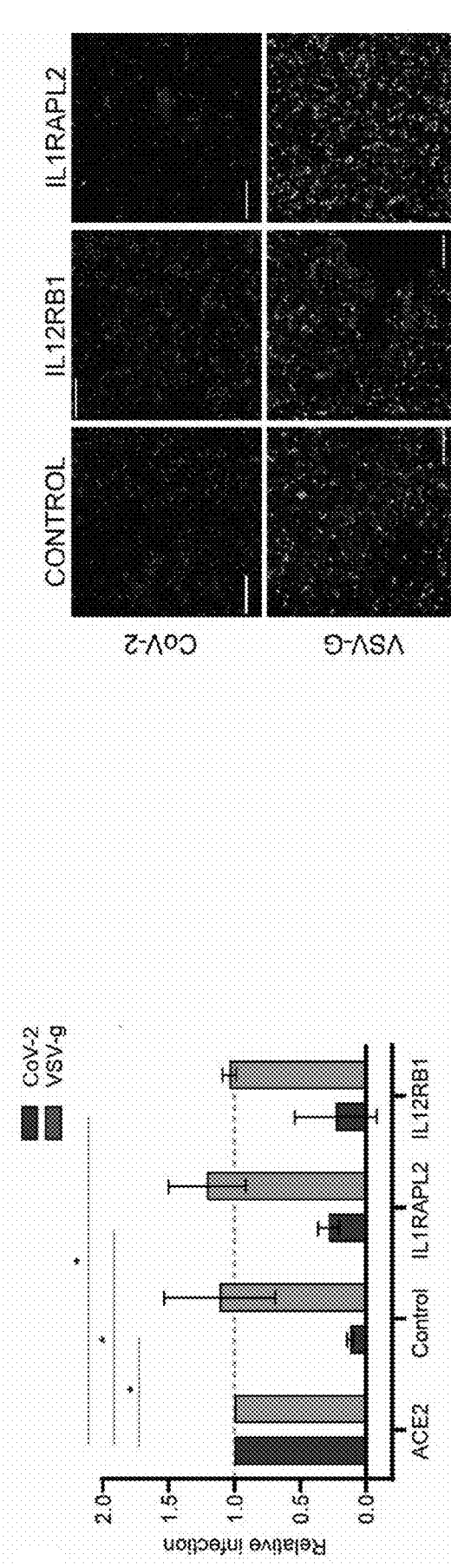

FIG. 10A is a set of representative micrographs and a bar graph showing SARS CoV-2 pseudotyped particle infection of HEK/293T cells transiently expressing a control vector or the SARS CoV-2 RBD receptor ACE2, IL12RB1, or IL1RAPL2. Blue bars show quantification for SARS CoV-2 pseudotyped particles. Grey bars show VSV-G pseudotyped activity, used as a control. Data were normalized to the respective infection levels of SARS CoV-2 and VSV-G particles in ACE2-expressing cells. Infected cells are represented in green; nuclei are depicted in blue. Scale bar=200 μm. Two way ANOVA with Sidak's correction for multiple comparisons; *p<0.05, p<0.01, *p<0.001. NS, not significant.

Figure 10B:
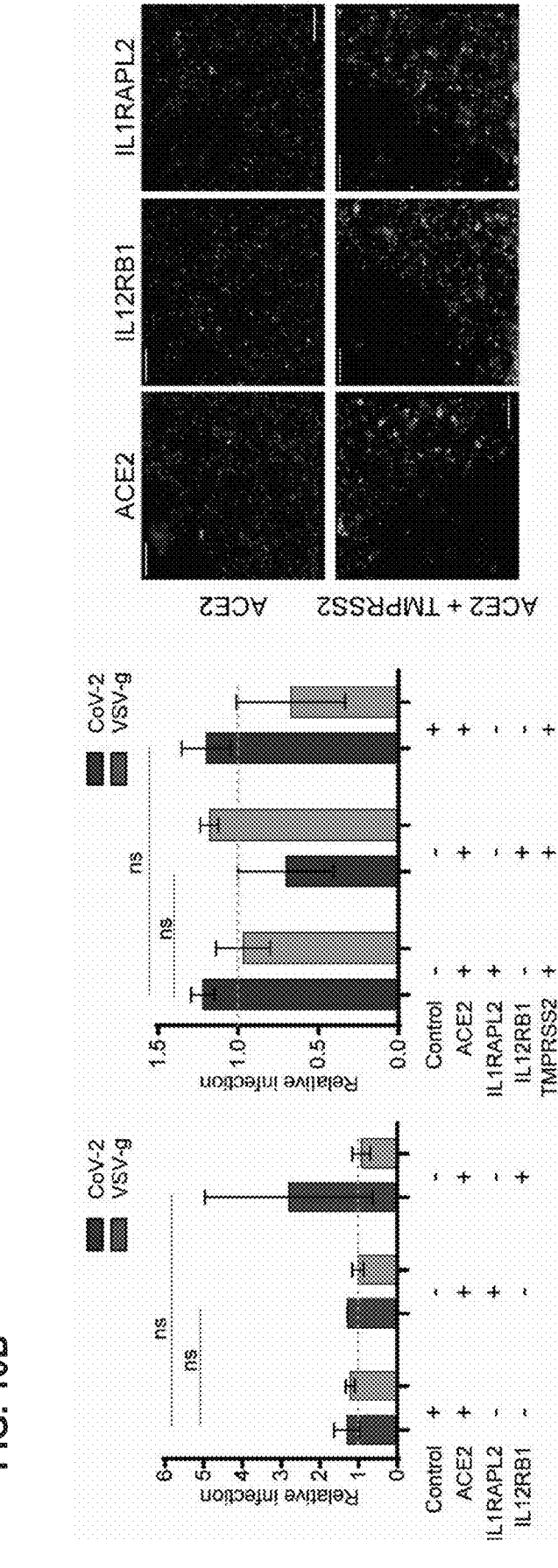

FIG. 10B is a set of representative micrographs and a bar graph showing SARS CoV-2 pseudotyped particle infection of HEK/293T cells transiently expressing ACE2 or ACE2 and TMPRSS2 and transfected with IL12RB1 or IL1RAPL2. Blue bars show quantification for SARS CoV-2 pseudotyped particles. Grey bars show VSV-G pseudotyped activity, used as a control. Data were normalized to the respective infection levels in ACE2-expressing or ACE2+ TMPRSS2-expressing cells, respectively. Infected cells are represented in green; nuclei are depicted in blue. Scale bar=200 μm. Two way ANOVA with Sidak's correction for multiple comparisons; *p<0.05, p<0.01, *p<0.001. NS, not significant.

DETAILED DESCRIPTION OF THE INVENTION

I. Definitions

Unless otherwise defined, all terms of art, notations, and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The term "about" as used herein refers to the usual error range for the respective value readily known to the skilled person in this technical field. Reference to "about" a value or parameter herein includes (and describes) aspects that are directed to that value or parameter per se.

As used herein, the singular forms "a," "an," and "the" include plural referents unless the context clearly dictates otherwise. For example, reference to "an isolated peptide" means one or more isolated peptides.

Throughout this specification and claims, the word "comprise," or variations such as "comprises" or "comprising" will be understood to imply the inclusion of a stated integer or group of integers but not the exclusion of any other integer or group of integers.

"Coronavirus" is a virus that infects mammals (e.g., humans) and causes respiratory infection. Coronaviruses that can infect the respiratory tract and cause respiratory illness (e.g., pneumonia) in humans include, without limitation, the beta coronavirus that causes Middle East Respiratory Syndrome (MERS), the beta coronavirus that causes severe acute respiratory syndrome (SARS), and the SARS-CoV-2 virus that causes COVID-19. The SARS-CoV-2 virus can additionally cause secondary infection (e.g., infection of nervous system tissue, immune cells, and/or lymphoid tissue).

"COVID-19" refers to the illness caused by SARS-CoV-2 infection that is typically characterized by fever, cough, and shortness of breath and may progress to pneumonia and respiratory failure. COVID-19 disease was first identified in Wuhan China in December 2019. In one embodiment, the patient with COVID-19 is confirmed by positive polymerase chain reaction (PCR) test (e.g. real time PCT, RT-PCT test) of a specimen (e.g., respiratory, blood, urine, stool, other bodily fluid specimen) from the patient for SARS-CoV-2. In one embodiment, the patient has SARS-CoV-2 specific antibodies (e.g. IgG and/or IgM antibodies), e.g. as determined by immunohistochemistry (IHC), enzyme-linked immunosorbent assay (ELISA), etc. Synonyms for COVID-19 include, without limitation, "novel coronavirus", "2019 Novel Coronavirus," and "2019-nCoV."

For the purposes herein "inflammation" refers to an immunological defense against infection, marked by increases in regional blood flow, immigration of white blood cells, and release of chemical toxins. Inflammation is one way the body uses to protect itself from infection. Clinical hallmarks of inflammation include redness, heat, swelling, pain, and loss of function of a body part. Systemically, inflammation may produce fevers, joint and muscle pains, organ dysfunction, and malaise.

"Pneumonia" refers to inflammation of one or both lungs, with dense areas of lung inflammation. In some aspects, pneumonia is due to viral infection. Symptoms of pneumonia may include fever, chills, cough with sputum production, chest pain, and shortness of breath. In one aspect, pneumonia has been confirmed by chest X-ray or computed tomography (CT scan).

"Severe pneumonia" refers to pneumonia in which the heart, kidneys or circulatory system are at risk of failing, or in which the lungs can no longer take in sufficient oxygen and develop acute respiratory distress syndrome (ARDS). A patient with severe pneumonia will typically be hospitalized and may be in an intensive care unit (ICU). Typically, the patient has severe dyspnea, respiratory distress, tachypnea (>breaths/min), and hypoxia, optionally with fever. Cyanosis can occur in children. In this definition, the diagnosis is clinical, and radiologic imaging is used for excluding complications. In one aspect, a patient with severe pneumonia has impaired lung function as determined by peripheral capillary oxygen saturation ($SpO_2$). In one aspect, the patient with severe pneumonia has impaired lung function as determined by ratio of arterial oxygen partial pressure to fractional inspired oxygen ($PaO2/FiO_2$). In one aspect, the patient with severe pneumonia has a $SpO_2 \leq 93\%$. In one aspect, the patient with severe pneumonia has a $PaO2/FiO_2$ of <300 mmHg (optionally adjusted for high altitude areas based on $PaO2/FiO_2 \times [\text{Atmospheric Pressure (mmHg)}/760]$). In one aspect, the patient has respiratory distress ($RR \geq 30$ breaths/minute). In one aspect, the patient has >50% lesions in pulmonary imaging.

"Critical pneumonia" refers to a severe pneumonia patient in whom respiratory failure, shock and/or organ has occurred. In one aspect, the patient with critical pneumonia requires mechanical ventilation.

"Mild pneumonia" presents with symptoms of an upper respiratory tract viral infection, including mild fever, cough (dry), sore throat, nasal congestion, malaise, headache, muscle pain, or malaise. Signs and symptoms of a more serious disease, such as dyspnea, are not present.

In "moderate pneumonia", respiratory symptoms such as cough and shortness of breath (or tachypnea in children) are present without signs of severe pneumonia. The patient with moderate pneumonia may be in a hospital, but not in an ICU or on a ventilator.

"Acute respiratory disease syndrome" or "ARDS" refers to a life-threatening lung condition that prevents enough oxygen from getting to the lungs and into the blood. In one embodiment, the diagnosis of ARDS is made based on the following criteria: acute onset, bilateral lung infiltrates on chest radiography of a non-cardiac origin, and a PaO/FiO ratio of <300 mmHg. In one embodiment, the ARDS is "mild ARDS" characterized by PaO2/FiO2 200 to 300 mmHg. In one embodiment, the ARDS is "moderate ARDS" characterized by PaO2/FiO2 100 to 200 mmHg. In one embodiment, the ARDS is "severe ARDS" characterized by PaO2/FiO2<100 mmHg.

"Viral pneumonia" refers to pneumonia caused by the entrance into a patient of one or more viruses. In one aspect, the virus is a DNA virus. In one aspect, the virus is an RNA virus. Examples of viruses causing viral pneumonia contemplated herein include, inter alia, those caused by: human immunodeficiency virus (HIV), hepatitis B virus, hepatitis C virus, influenza virus (including H1N1 or "swine flu" and H5N1 or "bird flu"), Zika virus, rotavirus, Rabies virus, West Nile virus, herpes virus, adenovirus, respiratory syncytial virus (RSV), norovirus, rotavirus, astrovirus, rhinovirus, human papillomavirus (HPV), polio virus, Dengue fever, Ebola virus, and coronavirus. In one aspect, the viral pneumonia is caused by a coronavirus. In one aspect, the viral pneumonia is caused by SARS CoV-2.

The term "patient" herein refers to a human patient. In one embodiment, the patient is hospitalized.

An "intravenous" or "iv" dose, administration, or formulation of a drug is one which is administered via a vein, e.g. by infusion.

A "subcutaneous" or "sc" dose, administration, or formulation of a drug is one which is administered under the skin, e.g. via a pre-filled syringe, auto-injector, or other device.

A "weight-based dose" of a drug refers to a dose that is based on the weight of the patient. In a preferred embodiment, where the drug is tocilizumab, the weight-based dose is 8 mg/kg (optionally 800 mg dose).

A "fixed dose" of a drug refers to a dose that is administered without regard to the patient's weight.

For the purposes herein, "clinical status" refers to a patients health condition. Examples include that the patient is improving or getting worse. In one embodiment, clinical status is based on an ordinal scale of clinical status. In one embodiment, clinical status is not based on whether or not the patient has a fever.

An "ordinal scale of clinical status" refers to a scale used to quantify outcomes which are non-dimensional. They include can include an outcome at a single point in time or can examine change which has occurred between two points in time. In one embodiment, the two points of time are "Day 1" (when first dose, e.g. 8 mg/kg, of the IL-6 antagonist such as tocilizumab is administered) compared with "Day 28" (when the patient is evaluated) and, optionally, at "Day 60" (when the patient is further evaluated). Ordinal scales include various "categories" which each evaluate patent status or outcome. In one embodiment, the ordinal scale is a "7-category ordinal scale".

In one embodiment, a "7-category ordinal scale" includes the following categories for evaluating the patient's status:
  1. Discharged from hospital (or "ready for discharge", e.g. as evidenced by normal body temperature and respiratory rate, and stable oxygen saturation on ambient air or ≤2 L supplemental oxygen)

2. Non-ICU hospital ward (or "ready for hospital ward") not requiring supplemental oxygen 3. Non-ICU hospital ward (or "ready for hospital ward") requiring supplemental oxygen 4. ICU or non-ICU hospital ward, requiring non-invasive ventilation or high-flow oxygen 5. ICU, requiring intubation and mechanical ventilation 6. ICU, requiring ECMO or mechanical ventilation and additional organ support (e.g. vasopressors, renal replacement therapy)

7. Death.

"Baseline" refers to a patient's status just prior to treatment and/or just prior to biomarker analysis. In one aspect, the patient is not ventilated at baseline. In one aspect, the patient is not receiving: a. continuous positive airway pressure (CPAP), b. bilevel positive airway pressure (BIPAP), or c. invasive ventilation at baseline. In one aspect, the patient has SpO2<94% while on ambient air. In one aspect, the patient does not have active bacterial, fungal, viral, or other infection (besides COVID-19) at baseline. In one aspect, the patient has alanine aminotransferase (ALT) or aspartate aminotransferase (AST)>5× the upper limit of normal (ULN) at baseline. In one aspect, the patient has an absolute neutrophil count (ANC)<1000/mL at baseline. In one embodiment, the patient has platelet count <50,000/mL at baseline.

An "elevated" level of a biomarker refers to an amount of that biomarker in the patient that is above the upper limit of normal (ULN). A "level above the upper limit of normal" refers to an amount of a biomarker that is abnormal or atypical in a subject (including a healthy subject) or patient (including one with pneumonia or experiencing inflammation).

For the purposes herein, "standard of care" or "SOC" refers to treatments or drugs commonly used to treat patients with pneumonia (e.g. viral pneumonia, such as COVID-19 pneumonia) including, inter alia, supportive care, administration of one or more anti-viral(s), and/or administration of one or more corticosteroid(s). In one embodiment, SOC comprises anti-viral (e.g. remdesivir or azithromycin) and/or corticosteroid (e.g. dexamethasone or prednisone) treatment.

"Supportive care" includes, without limitation: respiratory support (e.g. oxygen therapy via face mask or nasal cannula, high-flow nasal oxygen therapy or non-invasive mechanical ventilation, invasive mechanical ventilation, via extracorporeal membrane oxygenation (ECMO), etc.); circulation support (e.g. fluid resuscitation, boost microcirculation, vasoactive drugs); renal replacement therapy; plasma therapy; blood purification therapy; Xuebijing Injection (e.g., 100 mL/day twice a day); microecological preparation (e.g. probiotics, prebiotics, and synbiotics); anti-inflammatories (e.g. non-steroidal anti-inflammatory drugs, e.g. NSAIDs); herbal medicine; plasma (e.g. convalescent plasma) etc.

"Anti-viral" agents include, without limitation: alpha-interferon, lopinavir, ritonavir, lopinavir/ritonavir, remdesivir, azithromycin, ribavirin, hydroxychloroquine or chloroquine (with or without azithromycin), umifenovir, favipiravir etc. Optionally, the anti-viral is combined with alpha-interferon, ribavirin, and/or azithromycin. In one embodiment, the anti-viral is remdesivir or azithromycin. "Remdesivir" is an antiviral medication, a nucleotide analog, specifically an adenosine analogue, which inserts into viral RNA chains, causing their premature termination. Its molecular formula is $C_{27}H_{35}N_6O_8P$ and IUPAC Name is 2-ethylbutyl (2S)-2-[[[(2R,3S,4R,5R)-5-(4-aminopyrrolo[2, 1-f][1,2,4]triazin-7-yl)-5-cyano-3,4-dihydroxyoxolan-2-yl] methoxy-phenoxyphosphoryl]amino]propanoate. Remdesivir's laboratory name is GS-5734 and its CAS number is 1809249-37-3. It is described in U.S. Pat. No. 9,724,360 and is manufactured by Gilead Sciences.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone, such as methylprednisolone sodium succinate), dexamethasone or dexamethasone triamcinolone, hydrocortisone, and betamethasone. In one aspect, the corticosteroid is selected from prednisone, methylprednisolone, hydrocortisone, and dexamethasone. In one aspect, the corticosteroid is methylprednisolone. In one aspect, the corticosteroid is "low-dose" glucocorticoid (e.g. ≤1-2 mg/kg/day methylprednisolone, e.g. for 3-5 days). In one aspect, the corticosteroid is dexamethasone (e.g. dexamethasone administered orally or IV 6 mg once daily for up to 10 days) or prednisone.

An "anti-inflammatory" is a drug that reduces inflammation. Examples include, without limitation: steroids (e.g. dexamethasone), anti-ST2 (Astegolimab; MSTT1041A), IL-22Fc (UTTR1147A; see, e.g. US2014/0314711), statins, IL-6 antagonists, etc.

An "immunomodulator" is a drug that controls the immune system. Examples include, e.g., IL-6 antagonists, tocilizumab, sarilumab, anakinra, baricitinib, canakinumab, ruxolitinib, etc.

An "anti-coagulant" is a drug that helps prevent blood clots, e.g. heparin.

An "anti-fibrotic" is a drug that slows or halts fibrosis, e.g. tyrosine kinase inhibitor (e.g. imatinib) or pirfenidone.

An "anti-viral antibody" is one which binds to a virus and preferably neutralizes the ability of the virus to infect a patient and/or replicate in a patient. In one embodiment, it comprises a cocktail of two or more anti-viral antibodies, e.g. REGN-COV2.

Examples of "non-steroidal anti-inflammatory drugs" or "NSAIDs" include aspirin, acetylsalicylic acid, ibuprofen, flurbiprofen, naproxen, indomethacin, sulindac, tolmetin, phenylbutazone, diclofenac, ketoprofen, benorylate, mefenamic acid, methotrexate, fenbufen, azapropazone; COX-2 inhibitors such as celecoxib (CELEBREX®; 4-(5-(4-methylphenyl)-3-(trifluoromethyl)-1H-pyrazol-1-yl) benzenesulfonamide, valdecoxib (BEXTRA®), meloxicam (MOBIC®), GR 253035 (Glaxo Wellcome); and MK966 (Merck Sharp & Dohme), including salts and derivatives thereof, etc. Specific embodiments include: aspirin, naproxen, ibuprofen, indomethacin, and tolmetin.

Herein "human interleukin 6" (abbreviated as "IL-6") is a cytokine also known as B cell-stimulating factor 2 (BSF-2), or interferon beta-2 (IFNB2), hybridoma growth factor, and CTL differentiation factor. IL-6 was discovered as a differentiation factor contributing to activation of B cells (Hirano et al., Nature 324: 73-76 (1986)), and was later found to be a multifunction cytokine which influences the functioning of a variety of different cell types (Akira et al., Adv. in Immunology 54: 1-78 (1993)). Naturally occurring human IL-6 variants are known and included in this definition. Human IL-6 amino acid sequence information has been disclosed, see for example, UniProt P05231.

An "effective amount" refers to an amount of an agent (e.g., a therapeutic agent) that is effective to bring about a therapeutic/prophylactic benefit (e.g., as described herein) that is not outweighed by unwanted/undesirable side effects.

An "IL-6 antagonist" refers to agent that inhibits or blocks IL-6 biological activity via binding to human IL-6 or human IL-6 receptor. In one embodiment, the IL-6 antagonist is an antibody. In one embodiment, the IL-6 antagonist is an antibody that binds IL-6 receptor. Antibodies that bind IL-6 receptor include tocilizumab (including intravenous, iv, and subcutaneous, sc, formulations thereof) (Chugai, Roche, Genentech), satralizumab (Chugai, Roche, Genentech), sarilumab (Sanofi, Regeneron), NI-1201 (Novimmune and Tiziana), and vobarilizumab (Ablynx). In one embodiment, the IL-6 antagonist is a monoclonal antibody that binds IL-6. Antibodies that bind IL-6 include sirukumab (Centecor, Janssen), olokizumab (UCB), clazakizumab (BMS and Alder), siltuximab (Janssen), EBI-031 (Eleven Biotherapeutics and Roche). In one embodiment, the IL-6 antagonist is olamkicept.

For the purposes herein "human interleukin 6 receptor" (abbreviated as "IL-6R") refers to the receptor which binds IL-6, including both membrane-bound IL-6R (mIL-6R) and soluble IL-6R (sIL-6R). IL-6R can combine with interleukin 6 signal transducer glycoprotein 130 to form an active receptor complex. Alternatively spliced transcript variants encoding distinct isoforms of IL-6 have been reported and are included in this definition. The amino acid sequence structure of human IL-6R and its extracellular domain have been described; see, for example, Yamasaki et al., Science, 241: 825 (1988).

A "neutralizing" anti-IL-6R antibody herein is one which binds to IL-6R and is able to inhibit, to a measurable extent, the ability of IL-6 to bind to and/or active IL-6R. Tocilizumab is an example of a neutralizing anti-IL-6R antibody.

"Tocilizumab" or "TCZ" is a recombinant humanized monoclonal antibody that binds to human interleukin-6 receptor (IL-6R). It is an IgG1κ (gamma 1, kappa) antibody with two heavy chains and two light chains forming two antigen-binding sites. In a preferred embodiment, the light chain and heavy chain amino acid sequences of tocilizumab comprise SEQ ID NOs: 7 and 8, respectively.

Regarding an IL-6 antagonist, an "effective amount" refers to an amount of the IL-6 antagonist (e.g. IL-6 receptor antibody such as tocilizumab) that is effective for treating pneumonia (e.g. viral pneumonia, including COVID-19 pneumonia) and/or for treating acute respiratory distress syndrome (ARDS).

The term "pharmaceutical formulation" refers to a preparation which is in such form as to permit the biological activity of the active ingredient or ingredients to be effective, and which contains no additional components which are unacceptably toxic to a subject to which the formulation would be administered. Such formulations are sterile. In one embodiment, the formulation is for intravenous (iv) administration. In another embodiment, the formulation is for subcutaneous (sc) administration.

A "native sequence" protein herein refers to a protein comprising the amino acid sequence of a protein found in nature, including naturally occurring variants of the protein. The term as used herein includes the protein as isolated from a natural source thereof or as recombinantly produced.

The term "protein," as used herein, refers to any native protein from any vertebrate source, including mammals such as primates (e.g., humans) and rodents (e.g., mice and rats), unless otherwise indicated. The term encompasses "full-length," unprocessed protein any form of the protein that results from processing in the cell. The term also encompasses naturally occurring variants of the protein, e.g., splice variants or allelic variants, e.g., amino acid substitution mutations or amino acid deletion mutations. The term also includes isolated regions or domains of the protein, e.g., the extracellular domain (ECD).

An "isolated" protein or peptide is one which has been separated from a component of its natural environment. In some aspects, a protein or peptide is purified to greater than 95% or 99% purity as determined by, for example, electrophoresis (e.g., SDS-PAGE, isoelectric focusing (IEF), capillary electrophoresis) or chromatography (e.g., ion exchange or reverse phase HPLC).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "single transmembrane receptor," "single-pass transmembrane receptor," or "STM receptor," as used herein, refers to a protein having a single transmembrane domain. In some aspects, the STM receptor is expressed on the cell surface. Exemplary STM receptors are provided in Martinez-Martin et al., Cell, 174(5): 1158-1171, 2018 and Clark et al., Genome Res, 13: 2265-2270, 2003. In some aspects, the STM protein has the UniProt annotation "leucine-rich," "cysteine-rich," "ITIM/ITAM" (immunoreceptor tyrosine-based inhibition motif/immunoreceptor tyrosine-based activation motif), "TNFR" (tumor necrosis factor receptor), "TLR/ILR" (Toll-like receptor/interleukin receptor), "semaphorin," "Kinase-like," "Ig-like" (immunoglobulin-like), "fibronectin," "ephrin," "EGF," "cytokineR," or "cadherin". STM receptors may be identified based on, e.g., the presence of a signal peptide or a predicted transmembrane region in the amino acid sequence. In some aspects, the STM receptor is expressed as an extracellular domain.

As used herein, the term "extracellular domain" or "ECD" refers to a protein domain that is predicted to be localized outside of the outer plasma membrane of the cell. In some instances, the ECD is an ECD of a receptor, e.g., a STM receptor. In some aspects, the ECD is an ECD of angiotensin-converting enzyme 2 (ACE2); an ECD of neuropilin-2 (NRP2); an ECD of interleukin 12 receptor subunit beta 1 (IL12RB1); an ECD of contactin-1 (CNTN1), or an ECD of interleukin 1 receptor accessory protein like 2 (IL1RAPL2). In some aspects, the boundaries of the extracellular domain may be identified by prediction of domains that indicate that the protein crosses the plasma membrane, e.g., a transmembrane domain (e.g., a transmembrane helix). In some aspects, the presence of an extracellular domain may be predicted by the presence of a domain, sequence, or motif that indicates that the protein is trafficked to the plasma membrane, e.g., a signal sequence or a glycosylphosphatidylinositol (GPI) linkage site. In some aspects, the boundaries of the ECD are determined according to UniProt annotations. In some aspects, the ECD is soluble. In some aspects, the extracellular domain is expressed in the context of a full-length protein. In other aspects, the extracellular domain is expressed as an isolated extracellular domain, e.g., a sequence of amino acid residues comprising only the amino acid residues of a protein that are predicted to be extracellular.

As used herein, the terms "SARS-CoV-2 spike protein" and "SARS-CoV-2 S protein" refer to a protein that is anchored on the outer surface of the viral envelope of SARS-CoV-2 and forms the spike-like projections visible on the surface of the virus. The SARS-CoV-2 spike protein is composed of S1 and S2 subunits, with the S1 subunit located at the head of the spike and comprising the receptor-binding domain (RBD). Each spike is a trimer composed of three S proteins, which are referred to herein as "spike protein trimers" or "spike trimers". An exemplary SARS-CoV-2 spike protein has the sequence of SEQ ID NO: 1.

As used herein, the terms "SARS-CoV-2 spike protein receptor binding domain," "SARS-CoV-2 S protein receptor binding domain," "SARS-CoV-2 spike protein RBD," and "SARS-CoV-2 S protein RBD" refer to a portion of the SARS-CoV-2 S protein S1 subunit that is involved in binding receptors of a host cell (e.g., a human cell). An exemplary SARS-CoV-2 S protein RBD has the sequence of SEQ ID NO: 3. Other truncations of the SARS-CoV-2 S protein S1 subunit are also contemplated.

In some aspects, an isolated ECD or SARS-CoV-2 S protein RBD is included in a fusion protein. In some aspects, inclusion in a fusion protein increases solubility, ease of expression, ease of capture (e.g., on a protein A-coated plate), multimerization, or some other desirable property of the ECD or SARS-CoV-2 S protein RBD. In some aspects, the ECD or ECD fusion protein or the SARS-CoV-2 S protein RBD or SARS-CoV-2 S protein RBD fusion protein is a monomer. In other aspects, the ECD or ECD fusion protein or the SARS-CoV-2 S protein RBD or SARS-CoV-2 S protein RBD fusion protein is a multimer, e.g., a tetramer or a pentamer. In some aspects, the ECD or SARS-CoV-2 S protein RBD is fused to a human IgG. In some aspects, the ECD or SARS-CoV-2 S protein RBD is fused to a human Fc tag. In some aspects, the ECD or SARS-CoV-2 S protein RBD is fused to an Avidity AVITAG™ (Avi tag). In some aspects, the ECD or SARS-CoV-2 S protein RBD is fused to a polyhistidine (His) tag. In some aspects, the ECD or SARS-CoV-2 S protein RBD is fused to a glycoprotein D (gD) tag and a glycosylphosphatidylinositol (GPI) linker, e.g., a gD-GPI tag. In other aspects, the ECD or SARS-CoV-2 S protein RBD is fused to the pentamerization domain of rat cartilaginous oligomeric matrix protein (COMP) and the β-lactamase protein, e.g., as described in Bushell et al., *Genome Res,* 18: 622-630, 2008. In some aspects, the ECD fusion protein or SARS-CoV-2 S protein RBD fusion protein further includes a cleavage sequence, e.g., a TEV cleavage sequence, to allow removal of one or more domains. In some instances, an ECD fusion protein or SARS-CoV-2 S protein RBD fusion protein having an Avi tag and an Fc tag cleavable at a cleavage sequence is further processed to remove the Fc tag, to biotinylate the Avi tag, and to fuse the biotinylated ECD fusion protein or SARS-CoV-2 S protein RBD fusion protein to a fluorescent streptavidin (SA), e.g., to form a tetramerized ECD fusion protein or SARS-CoV-2 S protein RBD fusion protein. In some instances, the isolated ECD or ECD fusion protein or SARS-CoV-2 S protein RBD fusion protein is purified.

As used herein, a "modulator" is an agent that modulates (e.g., increases, decreases, activates, or inhibits) a given biological activity, e.g., an interaction or a downstream activity resulting from an interaction. A modulator or candidate modulator may be, e.g., a small molecule, an antibody, an antigen-binding fragment (e.g., a bis-Fab, an Fv, a Fab, a Fab'-SH, a F(ab')$_2$, a diabody, a linear antibody, an scFv, an ScFab, a VH domain, or a VHH domain), a peptide, a mimic, an antisense oligonucleotide, or an inhibitory nucleic acid (e.g., an antisense oligonucleotide (ASO) or a small interfering RNA (siRNA)).

By "increase" or "activate" is meant the ability to cause an overall increase, for example, of 20% or greater, of 50% or greater, or of 75%, 85%, 90%, or 95% or greater. In certain aspects, increase or activate can refer to a downstream activity of a protein-protein interaction.

By "reduce" or "inhibit" is meant the ability to cause an overall decrease, for example, of 20% or greater, of 50% or greater, or of 75%, 85%, 90%, or 95% or greater. In certain aspects, reduce or inhibit can refer to a downstream activity of a protein-protein interaction.

"Affinity" refers to the strength of the sum total of noncovalent interactions between a single binding site of a molecule (e.g., a receptor) and its binding partner (e.g., a ligand). Unless indicated otherwise, as used herein, "binding affinity" refers to intrinsic binding affinity, which reflects a 1:1 interaction between members of a binding pair (e.g., receptor and ligand). The affinity of a molecule X for its partner Y can generally be represented by the dissociation constant ($K_D$). Affinity can be measured by common methods known in the art, including those described herein.

"Complex" or "complexed" as used herein refers to the association of two or more molecules that interact with each other through bonds and/or forces (e.g., Van der Waals, hydrophobic, hydrophilic forces) that are not peptide bonds. In one aspect, a complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin or a detection agent).

The terms "host cell," "host cell line," and "host cell culture" are used interchangeably and refer to cells into which exogenous nucleic acid has been introduced, including the progeny of such cells. Host cells include "transfected cells," "transformed cells," and "transformants," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In some aspects, the host cell is stably transformed with the exogenous nucleic acid. In other aspects, the host cell is transiently transformed with the exogenous nucleic acid.

The term "angiotensin-converting enzyme 2" or "ACE2," as used herein, broadly refers to any native ACE2 from any mammalian source, including primates (e.g. humans) and rodents (e.g., mice and rats), unless otherwise indicated. The term encompasses full-length ACE2 and isolated regions or domains of ACE2, e.g., the ACE2 ECD. The term also encompasses naturally occurring variants of ACE2, e.g., splice variants or allelic variants. The amino acid sequence of an exemplary human ACE2 is shown under UniProt Accession No. Q9BYF1. Minor sequence variations, especially conservative amino acid substitutions of ACE2 that do not affect ACE2 function and/or activity, are also contemplated by the invention.

The term "contactin-1" or "CNTN1," as used herein, broadly refers to any native CNTN1 from any mammalian source, including primates (e.g. humans) and rodents (e.g., mice and rats), unless otherwise indicated. The term encompasses full-length CNTN1 and isolated regions or domains of CNTN1, e.g., the CNTN1 ECD. The term also encompasses naturally occurring variants of CNTN1, e.g., splice variants or allelic variants. The amino acid sequence of an exemplary human CNTN1 is shown under UniProt Accession No. O12860. Minor sequence variations, especially conservative amino acid substitutions of CNTN1 that do not affect CNTN1 function and/or activity, are also contemplated by the invention.

The term "neuropilin-2" or "NRP2," as used herein, broadly refers to any native NRP2 from any mammalian source, including primates (e.g. humans) and rodents (e.g., mice and rats), unless otherwise indicated. The term encompasses full-length NRP2 and isolated regions or domains of NRP2, e.g., the NRP2 ECD. The term also encompasses naturally occurring variants of NRP2, e.g., splice variants or allelic variants. The amino acid sequence of an exemplary human NRP2 is shown under UniProt Accession No. 060462. Minor sequence variations, especially conservative amino acid substitutions of NRP2 that do not affect NRP2 function and/or activity, are also contemplated by the invention.

The term "interleukin 12 receptor subunit beta 1" or "IL12RB1," as used herein, broadly refers to any native IL12RB1 from any mammalian source, including primates (e.g. humans) and rodents (e.g., mice and rats), unless otherwise indicated. The term encompasses full-length IL12RB1 and isolated regions or domains of IL12RB1, e.g., the IL12RB1 ECD. The term also encompasses naturally occurring variants of IL12RB1, e.g., splice variants or allelic variants. The amino acid sequence of an exemplary human IL12RB1 is shown under UniProt Accession No. P42701. Minor sequence variations, especially conservative amino acid substitutions of IL12RB1 that do not affect IL12RB1 function and/or activity, are also contemplated by the invention.

The term "interleukin 1 receptor accessory protein like 2" or "IL1RAPL2," as used herein, broadly refers to any native IL1RAPL2 from any mammalian source, including primates (e.g. humans) and rodents (e.g., mice and rats), unless otherwise indicated. The term encompasses full-length IL1RAPL2 and isolated regions or domains of IL1RAPL2, e.g., the IL1RAPL2 ECD. The term also encompasses naturally occurring variants of IL1RAPL2, e.g., splice variants or allelic variants. The amino acid sequence of an exemplary human IL1RAPL2 is shown under UniProt Accession No. Q9NP60. Minor sequence variations, especially conservative amino acid substitutions of IL1RAPL2 that do not affect IL1RAPL2 function and/or activity, are also contemplated by the invention.

The term "antagonist of CNTN1" or "CNTN1 antagonist" refers to a molecule that decreases signal transduction resulting from the interaction of CNTN1 with one or more of its binding partners, e.g., the SARS-CoV-2 spike (S) protein. The CNTN1 antagonist may result in a decrease in the binding of CNTN1 to one or more of its binding partners (e.g., the SARS-CoV-2 S protein) relative to binding of the two proteins in the absence of the antagonist. Antagonists of CNTN1 activity may include antibodies, antigen binding fragments thereof, immunoadhesins, fusion proteins, peptides (e.g., multimerized peptides, e.g., multimerized CNTN1 polypeptides), oligopeptides, inhibitory nucleic acids (e.g., ASOs or siRNAs), and other molecules that decrease signal transduction resulting from the interaction of CNTN1 with one or more of its binding partners, e.g., the SARS-CoV-2 S protein.

The term "antagonist of IL12RB1" or "IL12RB1 antagonist" refers to a molecule that decreases signal transduction resulting from the interaction of IL12RB1 with one or more of its binding partners, e.g., the SARS-CoV-2 S protein. The IL12RB1 antagonist may result in a decrease in the binding of IL12RB1 to one or more of its binding partners (e.g., the SARS-CoV-2 S protein) relative to binding of the two proteins in the absence of the antagonist. Antagonists of IL12RB1 activity may include antibodies, antigen binding fragments thereof, immunoadhesins, fusion proteins, peptides (e.g., multimerized peptides, e.g., multimerized IL12RB1 polypeptides), oligopeptides, inhibitory nucleic acids (e.g., ASOs or siRNAs), and other molecules that decrease signal transduction resulting from the interaction of IL12RB1 with one or more of its binding partners, e.g., the SARS-CoV-2 S protein.

The term "antagonist of IL1RAPL2" or "IL1RAPL2 antagonist" refers to a molecule that decreases signal transduction resulting from the interaction of IL1RAPL2 with one or more of its binding partners, e.g., the SARS-CoV-2 S protein. The IL1RAPL2 antagonist may result in a decrease in the binding of IL1RAPL2 to one or more of its binding partners (e.g., the SARS-CoV-2 S protein) relative to binding of the two proteins in the absence of the antagonist. Antagonists of IL1RAPL2 activity may include antibodies, antigen binding fragments thereof, immunoadhesins, fusion proteins, peptides (e.g., multimerized peptides, e.g., multimerized IL1RAPL2 polypeptides), oligopeptides, inhibitory nucleic acids (e.g., ASOs or siRNAs), and other molecules that decrease signal transduction resulting from the interaction of IL1RAPL2 with one or more of its binding partners, e.g., the SARS-CoV-2 S protein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "antibody" herein is used in the broadest sense and encompasses various antibody structures, including but not limited to monoclonal antibodies, polyclonal antibodies, multispecific antibodies (e.g., bispecific antibodies), and antibody fragments (e.g., bis-Fabs) so long as they exhibit the desired antigen-binding activity.

An "antigen-binding fragment" or "antibody fragment" refers to a molecule other than an intact antibody that comprises a portion of an intact antibody that binds the antigen to which the intact antibody binds. Examples of antigen-binding fragments include but are not limited to bis-Fabs; Fv; Fab; Fab, Fab'-SH; F(ab')$_2$; diabodies; linear antibodies; single-chain antibody molecules (e.g., scFv, scFab); and multispecific antibodies formed from antibody fragments.

A "single-domain antibody" refers to an antibody fragment comprising all or a portion of the heavy chain variable domain or all or a portion of the light chain variable domain of an antibody. In certain aspects, a single-domain antibody is a human single-domain antibody (see, e.g., U.S. Pat. No. 6,248,516 B1). Examples of single-domain antibodies include but are not limited to a VHH.

A "Fab" fragment is an antigen-binding fragment generated by papain digestion of antibodies and consists of an entire L chain along with the variable region domain of the H chain (VH), and the first constant domain of one heavy chain (CH1). Papain digestion of antibodies produces two identical Fab fragments. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having an additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all Lys447 residues removed, antibody populations with no Lys447 residues removed, and antibody populations having a mixture of antibodies with and without the Lys447 residue.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

The terms "full-length antibody," "intact antibody," and "whole antibody" are used herein interchangeably to refer to an antibody having a structure substantially similar to a native antibody structure or having heavy chains that contain an Fc region as defined herein.

"Single-chain Fv" also abbreviated as "sFv" or "scFv" are antibody fragments that comprise the VH and VL antibody domains connected into a single polypeptide chain. Preferably, the scFv polypeptide further comprises a polypeptide linker between the VH and VL domains, which enables the scFv to form the desired structure for antigen binding. For a review of scFv, see Pluckthun, The Pharmacology of Monoclonal Antibodies, vol. 113, Rosenburg and Moore eds., Springer-Verlag, New York, pp. 269-315 (1994); Malmborg et al., J. Immunol. Methods 183:7-13, 1995.

The term "small molecule" refers to any molecule with a molecular weight of about 2000 daltons or less, e.g., about 1000 daltons or less. In some aspects, the small molecule is a small organic molecule.

The term "mimic" or "molecular mimic," as used herein, refers to a polypeptide having sufficient similarity in conformation and/or binding ability (e.g., secondary structure, tertiary structure) to a given polypeptide or to a portion of said polypeptide to bind to a binding partner of said polypeptide. The mimic may bind the binding partner with equal, less, or greater affinity than the polypeptide it mimics. A molecular mimic may or may not have obvious amino acid sequence similarity to the polypeptide it mimics. A mimic may be naturally occurring or may be engineered. In some aspects, the mimic is a mimic of a member of a binding pair. In yet other aspects, the mimic is a mimic of another protein that binds to a member of the binding pair. In some aspects, the mimic may perform all functions of the mimicked polypeptide. In other aspects, the mimic does not perform all functions of the mimicked polypeptide.

As used herein, the term "conditions permitting the binding" of two or more proteins to each other refers to conditions (e.g., protein concentration, temperature, pH, salt concentration) under which the two or more proteins would interact in the absence of a modulator or a candidate modulator. Conditions permitting binding may differ for individual proteins and may differ between protein-protein interaction assays (e.g., surface plasmon resonance assays, biolayer interferometry assays, enzyme-linked immunosorbent assays (ELISA), extracellular interaction assays, and cell surface interaction assays.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "sample," as used herein, refers to a composition that is obtained or derived from a subject and/or individual of interest that contains a cellular and/or other molecular entity that is to be characterized and/or identified, for example, based on physical, biochemical, chemical, and/or physiological characteristics. For example, the phrase "disease sample" and variations thereof refers to any sample obtained from a subject of interest that would be expected or is known to contain the cellular and/or molecular entity that is to be characterized. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, plasma, serum, blood-derived cells, urine, cerebro-spinal fluid, saliva, buccal swab, sputum, tears, perspiration, mucus, tumor lysates, and tissue culture medium, tissue extracts such as homogenized tissue, tumor tissue, cellular extracts, and combinations thereof. The sample may be an archival sample, a fresh sample, or a frozen sample. In some aspects, the sample is a formalin-fixed and paraffin-embedded (FFPE) tumor tissue sample.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease (e.g., preventing a respiratory disease (e.g., pneumonia (e.g. viral pneumonia, including COVID-19 pneumonia (e.g., severe COVID-19 pneumonia)), ARDS, asthma, chronic obstructive pulmonary disorder (COPD), influenza (e.g., influenza A or B), lung diseases, and the like) or CRS (e.g., CRS caused by a viral infection (e.g., SARS-CoV-2) or CAR-T-cell-induced CRS)), reducing or preventing secondary infection in a patient having an infection (e.g., reducing or preventing secondary infection of nervous tissue, immune cells, lymphoid tissue, and/or lung tissue), alleviation of symptoms, diminishment of any direct or indirect pathological consequences of the disease, decreasing the rate of disease progression, amelioration or palliation of the disease state, and remission or improved prognosis.

The "pathology" of a disease or condition includes all phenomena that compromise the well-being of the patient.

"Amelioration," "ameliorating," "alleviation," "alleviating," or equivalents thereof, refers to both therapeutic treatment and prophylactic or preventative measures, wherein the object is to ameliorate, prevent, slow down (lessen), decrease or inhibit a disease or condition, e.g., a respiratory disease (e.g., pneumonia (e.g. viral pneumonia, including COVID-19 pneumonia (e.g., severe COVID-19 pneumonia)), ARDS, asthma, chronic obstructive pulmonary disorder (COPD), influenza (e.g., influenza A or B), lung diseases, and the like) or CRS (e.g., CRS caused by a viral infection (e.g., COVID-19) or CAR-T-cell-induced CRS). Those in need of treatment include those already with the disease or condition as well as those prone to having the disease or condition or those in whom the disease or condition is to be prevented.

II. Methods of Identifying Modulators of Protein-Protein Interactions

A. Methods of Identifying Modulators of the Interaction Between the SARS-CoV-2 S Protein and CNTN1

Contactin-1 (CNTN1) was identified as a previously unrecognized host cell factor that directly interacts with the SARS-CoV-2 spike (S) protein. Provided herein are methods for identifying modulators of the interaction between CNTN1 and the SARS-CoV-2 S protein (e.g., modulators of the interaction between CNTN1 and the SARS-CoV-2 S protein RBD), e.g., CNTN1 or SARS-CoV-2 S protein antagonists that decrease binding of CNTN1 and the SARS-CoV-2 S protein and/or decrease the amount, strength, or duration of a downstream activity resulting from the interaction, e.g., decrease infection of a host cell by the SARS-CoV-2 virus.

In some aspects, the disclosure features a method of identifying a modulator of the interaction between the SARS-CoV-2 S protein and CNTN1, the method comprising (a) providing a candidate modulator; (b) contacting the SARS-CoV-2 S protein RBD with CNTN1 in the presence or absence of the candidate modulator under conditions permitting the binding of the SARS-CoV-2 S protein RBD to CNTN1; and (c) measuring the binding of the protein of the SARS-CoV-2 S protein RBD to CNTN1, wherein an increase or decrease in binding in the presence of the candidate modulator relative to binding in the absence of the candidate modulator identifies the candidate modulator as a modulator of the interaction between the SARS-CoV-2 S protein and CNTN1. Increased or decreased binding may be assessed using, e.g., surface plasmon resonance, biolayer interferometry, or an enzyme-linked immunosorbent assay (ELISA).

In some aspects, the candidate modulator is identified as a modulator if the increase in binding is at least 40%. In some aspects, the increase in binding is at least 5%, at least 10%, at least 20%, at least 30%, at least 40%, at least 50%, at least 60%, at least 70%, at least 80%, at least 90%, at least 100%, or more than 100% (e.g., 5%-15%, 15%-25%, 25%-35%, 35%-45%, 45%-55%, 55%-65%, 65%-75%, 75%-85%, 85%-95%, 95%-100%, or more than 100%). In some aspects, the increase in binding is at least 40%.

In some aspects, the candidate modulator is identified as a modulator if the decrease in binding is at least 40%. In some aspects, the decrease in binding is at least 5%, at least 10%, at least 20%, at least 30%, at least 40%, at least 50%, at least 60%, at least 70%, at least 80%, at least 90%, or 100% (e.g., 5%-15%, 15%-25%, 25%-35%, 35%-45%, 45%-55%, 55%-65%, 65%-75%, 75%-85%, 85%-95%, or 95%-100%). In some aspects, the decrease in binding is at least 40%.

In some aspects, the disclosure features a method of identifying a modulator of a downstream activity of the SARS-CoV-2 S protein, the method comprising (a) providing a candidate modulator; (b) contacting the SARS-CoV-2 S protein RBD with CNTN1 in the presence or absence of the candidate modulator under conditions permitting the binding of the SARS-CoV-2 S protein RBD to CNTN1; and (c) measuring a downstream activity of the SARS-CoV-2 S protein RBD, wherein a change in the downstream activity in the presence of the candidate modulator relative to the downstream activity in the absence of the candidate modulator identifies the candidate modulator as a modulator of the downstream activity of the SARS-CoV-2 S protein.

In some aspects, the disclosure features a method of identifying a modulator of a downstream activity of CNTN1, the method comprising (a) providing a candidate modulator; (b) contacting CNTN1 with the SARS-CoV-2 S protein RBD in the presence or absence of the candidate modulator under conditions permitting the binding of CNTN1 to the SARS-CoV-2 S protein RBD; and (c) measuring a downstream activity of CNTN1, wherein a change in the downstream activity in the presence of the candidate modulator relative to the downstream activity in the absence of the candidate modulator identifies the candidate modulator as a modulator of the downstream activity of CNTN1.

In some aspects, the modulator is an inhibitor of the downstream activity of the SARS-CoV-2 S protein or CNTN1. In some aspects, the change in the downstream activity is a decrease in the amount, strength, or duration of the downstream activity. In some aspects, the downstream activity of the SARS-CoV-2 S protein or CNTN1 is infection of a cell by SARS-CoV-2. In some aspects, infection decreased in the presence of the modulator, e.g., decreased by at least 5%, 10%, 15%, 20%, 25%, 30%, 35%, 40%, 45%, 50%, 55%, 60%, 65%, 70%, 75%, 80%, 85%, 90%, 95%, 98%, or 99% or decreased by 100% (i.e., abolished), e.g., decreased by 5%-15%, 15%-25%, 25%-35%, 35%-45%, 45%-55%, 55%-65%, 65%-75%, 75%-85%, 85%-95%, or 95%-100% as measured in a viral infection assay (e.g., as described in Cantuti-Castelvetri et al., *Science, DOI:* 10.1126/science.abd2985, 2020 or a viral entry assay using SARS-CoV-2 S protein pseudotyped particles). In some aspects, infection is decreased by at least 40% in the presence of the modulator.

In some aspects, the modulator is an antibody or antigen-binding fragment thereof that binds the SARS-CoV-2 S protein, e.g., binds to an epitope of the SARS-CoV-2 S protein that interacts with CNTN1. In some aspects, the modulator binds to the SARS-CoV-2 S protein RBD, e.g., binds to an epitope of the SARS-CoV-2 S protein RBD that interacts with CNTN1. In some aspects, the antibody or antigen-binding fragment thereof that binds the SARS-CoV-2 S protein RBD blocks the interaction of the SARS-CoV-2 S protein RBD with CNTN1.

In some aspects, the modulator is an antibody or antigen-binding fragment thereof that binds CNTN1, e.g., binds to an epitope of CNTN1 that interacts with the SARS-CoV-2 S protein RBD. In some aspects, the antibody or antigen-binding fragment thereof that binds CNTN1 blocks the interaction of CNTN1 with the SARS-CoV-2 S protein RBD. A list of exemplary anti-CNTN1 antibodies is provided in Table 1.

TABLE 1

| Anti-CNTN1 antibodies | |
| --- | --- |
| Antibody | Vendor |
| LS-B10585 | LifeSpan BioSciences |
| MBS9210942 | MyBioSource |
| 13843-1-AP | PROTEINTECH ® |
| orb646228 | biorbyt |
| DF12904 | Affinity Biosciences |
| PA5-109564 | Thermo Fisher Scientific |
| MA5-29177 | Invitrogen |
| 10383-MM01 | Sino Biological |
| MAB11954 | Abnova |
| 102-27743 | RayBiotech |
| AF904 | R&D Systems |
| NBP2-68900 | Novus Biologicals |
| ab66265 | Abcam |

In some aspects, the modulator is a bispecific antibody that binds ACE2 and CNTN1.

B. Methods of Identifying Modulators of the Interaction Between the SARS-CoV-2 S Protein and IL12RB1

Interleukin 12 receptor subunit beta 1 (IL12RB1) was identified as a previously unrecognized host cell factor that directly interacts with the SARS-CoV-2 S protein. Provided herein are methods for identifying modulators of the interaction between IL12RB1 and the SARS-CoV-2 S protein (e.g., modulators of the interaction between IL12RB1 and the SARS-CoV-2 S protein RBD), e.g., IL12RB1 or SARS-CoV-2 S protein antagonists that decrease binding of IL12RB1 and the SARS-CoV-2 S protein RBD and/or decrease the amount, strength, or duration of a downstream activity resulting from the interaction, e.g., decrease infection of a host cell by the SARS-CoV-2 virus.

In some aspects, the disclosure features a method of identifying a modulator of the interaction between the SARS-CoV-2 S protein and IL12RB1, the method comprising (a) providing a candidate modulator; (b) contacting the SARS-CoV-2 S protein RBD with IL12RB1 in the presence or absence of the candidate modulator under conditions permitting the binding of the SARS-CoV-2 S protein RBD to IL12RB1; and (c) measuring the binding of the protein of the SARS-CoV-2 S protein RBD to IL12RB1, wherein an increase or decrease in binding in the presence of the candidate modulator relative to binding in the absence of the candidate modulator identifies the candidate modulator as a modulator of the interaction between the SARS-CoV-2 S protein and IL12RB1. Increased or decreased binding may be assessed using, e.g., surface plasmon resonance, biolayer interferometry, or an enzyme-linked immunosorbent assay (ELISA).

In some aspects, the candidate modulator is identified as a modulator if the increase in binding is at least 40%. In some aspects, the increase in binding is at least 5%, at least 10%, at least 20%, at least 30%, at least 40%, at least 50%, at least 60%, at least 70%, at least 80%, at least 90%, at least 100%, or more than 100% (e.g., 5%-15%, 15%-25%, 25%-35%, 35%-45%, 45%-55%, 55%-65%, 65%-75%, 75%-85%, 85%-95%, 95%-100%, or more than 100%). In some aspects, the increase in binding is at least 40%.

In some aspects, the candidate modulator is identified as a modulator if the decrease in binding is at least 40%. In some aspects, the decrease in binding is at least 5%, at least 10%, at least 20%, at least 30%, at least 40%, at least 50%, at least 60%, at least 70%, at least 80%, at least 90%, or 100% (e.g., 5%-15%, 15%-25%, 25%-35%, 35%-45%, 45%-55%, 55%-65%, 65%-75%, 75%-85%, 85%-95%, or 95%-100%). In some aspects, the decrease in binding is at least 40%.

In some aspects, the disclosure features a method of identifying a modulator of a downstream activity of the SARS-CoV-2 S protein, the method comprising (a) providing a candidate modulator; (b) contacting the SARS-CoV-2 S protein RBD with IL12RB1 in the presence or absence of the candidate modulator under conditions permitting the binding of the SARS-CoV-2 S protein RBD to IL12RB1; and (c) measuring a downstream activity of the SARS-CoV-2 S protein RBD, wherein a change in the downstream activity in the presence of the candidate modulator relative to the downstream activity in the absence of the candidate modulator identifies the candidate modulator as a modulator of the downstream activity of the SARS-CoV-2 S protein.

In some aspects, the disclosure features a method of identifying a modulator of a downstream activity of IL12RB1, the method comprising (a) providing a candidate modulator; (b) contacting IL12RB1 with the SARS-CoV-2 S protein RBD in the presence or absence of the candidate modulator under conditions permitting the binding of IL12RB1 to the SARS-CoV-2 S protein RBD; and (c) measuring a downstream activity of IL12RB1, wherein a change in the downstream activity in the presence of the candidate modulator relative to the downstream activity in the absence of the candidate modulator identifies the candidate modulator as a modulator of the downstream activity of IL12RB1.

In some aspects, the modulator is an inhibitor of the downstream activity of the SARS-CoV-2 S protein or IL12RB1. In some aspects, the change in the downstream activity is a decrease in the amount, strength, or duration of the downstream activity. In some aspects, the downstream activity of the SARS-CoV-2 S protein or IL12RB1 is infection of a cell by SARS-CoV-2. In some aspects, infection decreased in the presence of the modulator, e.g., decreased by at least 5%, 10%, 15%, 20%, 25%, 30%, 35%, 40%, 45%, 50%, 55%, 60%, 65%, 70%, 75%, 80%, 85%, 90%, 95%, 98%, or 99% or decreased by 100% (i.e., abolished), e.g., decreased by 5%-15%, 15%-25%, 25%-35%, 35%-45%, 45%-55%, 55%-65%, 65%-75%, 75%-85%, 85%-95%, or 95%-100% as measured in a viral infection assay (e.g., as described in Cantuti-Castelvetri et al., *Science, DOI:* 10.1126/science.abd2985 (2020) or a viral entry assay using SARS-CoV-2 S protein pseudotyped particles. In some aspects, infection is decreased by at least 40% in the presence of the modulator.

In some aspects, the modulator is an antibody or antigen-binding fragment thereof that binds the SARS-CoV-2 S protein, e.g., binds to an epitope of the SARS-CoV-2 S protein that interacts with IL12RB1. In some aspects, the modulator binds to the SARS-CoV-2 S protein RBD, e.g., binds to an epitope of the SARS-CoV-2 S protein RBD that interacts with IL12RB1. In some aspects, the antibody or antigen-binding fragment thereof that binds the SARS-CoV-2 S protein RBD blocks the interaction of the SARS-CoV-2 S protein RBD with IL12RB1.

In some aspects, the modulator is an antibody or antigen-binding fragment thereof that binds IL12RB1, e.g., binds to an epitope of IL12RB1 that interacts with the SARS-CoV-2 S protein RBD. In some aspects, the antibody or antigen-binding fragment thereof that binds IL12RB1 blocks the interaction of IL12RB1 with the SARS-CoV-2 S protein RBD. A list of exemplary anti-IL12RB1 antibodies is provided in Table 2.

TABLE 2

| Anti-IL12RB1 antibodies | |
| --- | --- |
| Antibody | Vendor |
| LS-C387696 | LifeSpan BioSciences |
| 13287-1-AP | PROTEINTECH ® |
| CF405M | biorbyt |
| LS-C335191 | LifeSpan BioSciences |
| 11674-MM05 | Sino Biological |
| PA5-21527 | Thermo Fisher Scientific |
| PAB18563 | Abnova |
| FAB1998P-100 | R&D Systems |

In some aspects, the modulator is a bispecific antibody that binds ACE2 and IL12RB1.

C. Methods of Identifying Modulators of the Interaction Between the SARS-CoV-2 S Protein and IL1RAPL2

Interleukin 1 receptor accessory protein like 2 (IL1RAPL2) was identified as a previously unrecognized host cell factor that directly interacts with the SARS-CoV-2 S protein. Provided herein are methods for identifying modulators of the interaction between IL1RAPL2 and the SARS-CoV-2 S protein (e.g., modulators of the interaction between IL1RAPL2 and the SARS-CoV-2 S protein RBD), e.g., IL1RAPL2 or SARS-CoV-2 S protein antagonists that decrease binding of IL1RAPL2 and the SARS-CoV-2 S protein and/or decrease the amount, strength, or duration of a downstream activity resulting from the interaction, e.g., decrease infection of a host cell by the SARS-CoV-2 virus.

In some aspects, the disclosure features a method of identifying a modulator of the interaction between the SARS-CoV-2 S protein and IL1RAPL2, the method comprising (a) providing a candidate modulator; (b) contacting the SARS-CoV-2 S protein RBD with IL1RAPL2 in the presence or absence of the candidate modulator under conditions permitting the binding of the SARS-CoV-2 S protein RBD to IL1RAPL2; and (c) measuring the binding of the protein of the SARS-CoV-2 S protein RBD to IL1RAPL2, wherein an increase or decrease in binding in the presence of the candidate modulator relative to binding in the absence of the candidate modulator identifies the candidate modulator as a modulator of the interaction between the SARS-CoV-2 S protein and IL1RAPL2. Increased or decreased binding may be assessed using, e.g., surface plasmon resonance, biolayer interferometry, or an enzyme-linked immunosorbent assay (ELISA).

In some aspects, the candidate modulator is identified as a modulator if the increase in binding is at least 40%. In some aspects, the increase in binding is at least 5%, at least 10%, at least 20%, at least 30%, at least 40%, at least 50%, at least 60%, at least 50%, at least 80%, at least 90%, at least 100%, or more than 100% (e.g., 5%-15%, 15%-25%, 25%-35%, 35%-45%, 45%-55%, 55%-65%, 65%-75%, 75%-85%, 85%-95%, 95%-100%, or more than 100%). In some aspects, the increase in binding is at least 40%.

In some aspects, the candidate modulator is identified as a modulator if the decrease in binding is at least 40%. In some aspects, the decrease in binding is at least 5%, at least 10%, at least 20%, at least 30%, at least 40%, at least 50%, at least 60%, at least 70%, at least 80%, at least 90%, or 100% (e.g., 5%-15%, 15%-25%, 25%-35%, 35%-45%, 45%-55%, 55%-65%, 65%-75%, 75%-85%, 85%-95%, or 95%-100%). In some aspects, the decrease in binding is at least 40%.

In some aspects, the disclosure features a method of identifying a modulator of a downstream activity of the SARS-CoV-2 S protein, the method comprising (a) providing a candidate modulator; (b) contacting the SARS-CoV-2 S protein RBD with IL1RAPL2 in the presence or absence of the candidate modulator under conditions permitting the binding of the SARS-CoV-2 S protein RBD to IL1RAPL2; and (c) measuring a downstream activity of the SARS-CoV-2 S protein RBD, wherein a change in the downstream activity in the presence of the candidate modulator relative to the downstream activity in the absence of the candidate modulator identifies the candidate modulator as a modulator of the downstream activity of the SARS-CoV-2 S protein.

In some aspects, the disclosure features a method of identifying a modulator of a downstream activity of IL1RAPL2, the method comprising (a) providing a candidate modulator; (b) contacting IL1RAPL2 with the SARS-CoV-2 S protein RBD in the presence or absence of the candidate modulator under conditions permitting the binding of IL1RAPL2 to the SARS-CoV-2 S protein RBD; and (c) measuring a downstream activity of IL1RAPL2, wherein a change in the downstream activity in the presence of the candidate modulator relative to the downstream activity in the absence of the candidate modulator identifies the candidate modulator as a modulator of the downstream activity of IL1RAPL2.

In some aspects, the modulator is an inhibitor of the downstream activity of the SARS-CoV-2 S protein or IL1RAPL2. In some aspects, the change in the downstream activity is a decrease in the amount, strength, or duration of the downstream activity. In some aspects, the downstream activity of the SARS-CoV-2 S protein or IL1RAPL2 is infection of a cell by SARS-CoV-2. In some aspects, infection decreased in the presence of the modulator, e.g., decreased by at least 5%, 10%, 15%, 20%, 25%, 30%, 35%, 40%, 45%, 50%, 55%, 60%, 65%, 70%, 75%, 80%, 85%, 90%, 95%, 98%, or 99% or decreased by 100% (i.e., abolished), e.g., decreased by 5%-15%, 15%-25%, 25%-35%, 35%-45%, 45%-55%, 55%-65%, 65%-75%, 75%-85%, 85%-95%, or 95%-100%) as measured in a viral infection assay (e.g., as described in Cantuti-Castelvetri et al., *Science, DOI:* 10.1126/science.abd2985 (2020) or a viral entry assay using SARS-CoV-2 S protein pseudotyped particles. In some aspects, infection is decreased by at least 40% in the presence of the modulator.

In some aspects, the modulator is an antibody or antigen-binding fragment thereof that binds the SARS-CoV-2 S protein RBD, e.g., binds to an epitope of the SARS-CoV-2 S protein RBD that interacts with IL1RAPL2. In some aspects, the antibody or antigen-binding fragment thereof that binds the SARS-CoV-2 S protein RBD blocks the interaction of the SARS-CoV-2 S protein RBD with IL1RAPL2.

In some aspects, the modulator is an antibody or antigen-binding fragment thereof that binds IL1RAPL2, e.g., binds to an epitope of IL1RAPL2 that interacts with the SARS-CoV-2 S protein. In some aspects, the modulator binds to the SARS-CoV-2 S protein RBD, e.g., binds to an epitope of the SARS-CoV-2 S protein RBD that interacts with CNTN1. In some aspects, the antibody or antigen-binding fragment thereof that binds IL1RAPL2 blocks the interaction of IL1RAPL2 with the SARS-CoV-2 S protein RBD. A list of exemplary anti-IL1RAPL2 antibodies is provided in Table 3.

TABLE 3

| Anti-IL1RAPL2 antibodies | |
|---|---|
| Antibody | Vendor |
| GTX46331 | GeneTex |
| AF1007 | R&D Systems |
| LS-C487490 | Thermo Fisher Scientific |
| HPA036129 | Atlas Antibodies |
| SAB2101149-100UL | MilliporeSigma |

In some aspects, the modulator is a bispecific antibody that binds ACE2 and IL1RAPL2.

D. Modulators

In some aspects, the modulator or candidate modulator of the interaction between CNTN1 and the SARS-CoV-2 S protein; IL12RB1 and the SARS-CoV-2 S protein, or IL1RAPL2 and the SARS-CoV-2 S protein is a small molecule, an antibody or antigen-binding fragment thereof, a peptide, a mimic, or an inhibitory nucleic acid (e.g., an antisense oligonucleotide (ASO) or an siRNA). In some aspects, the antigen-binding fragment is a bis-Fab, an Fv, a Fab, a Fab'-SH, a F(ab')2, a diabody, a linear antibody, an scFv, an scFab, a VH domain, or a VHH domain. Exemplary modulators are further described in Section III herein.

E. Assays for Modulation of Protein-Protein Interactions

In some aspects, the binding of CNTN1, IL12RB1, or IL1RAPL2 and the SARS-CoV-2 S protein in the presence or absence of the candidate modulator is assessed in an assay for protein-protein interaction. Modulation of the interaction between CNTN1 and the SARS-CoV-2 S protein; IL12RB1 and the SARS-CoV-2 S protein, or IL1RAPL2 and the SARS-CoV-2 S protein may be identified as an increase in protein-protein interaction in the presence of the modulator compared to protein-protein interaction in the absence of the modulator, e.g., an increase of 5%, 10%, 15%, 20%, 25%, 30%, 35%, 40%, 45%, 50%, 55%, 60%, 65%, 70%, 80%, 90%, 95%, 100%, or more than 100% (e.g., 5%-15%, 15%-25%, 25%-35%, 35%-45%, 45%-55%, 55%-65%, 65%-75%, 75%-85%, 85%-95%, 95%-100%, or more than 100%) in protein-protein interaction. Alternatively, modulation may be identified as a decrease in protein-protein interaction in the presence of the modulator compared to protein-protein interaction in the absence of the modulator, e.g., an decrease of 5%, 10%, 15%, 20%, 25%, 30%, 35%, 40%, 45%, 50%, 55%, 60%, 65%, 70%, 80%, 90%, 95%, or 100% (e.g., 5%-15%, 15%-25%, 25%-35%, 35%-45%, 45%-55%, 55%-65%, 65%-75%, 75%-85%, 85%-95%, or 95%-100%) in protein-protein interaction. The assay for protein-protein interaction may be, e.g., an SPR assay, a biolayer interferometry (BLI) assay, an enzyme-linked immunosorbent assay (ELISA), an extracellular interaction assay, or a cell surface interaction assay.

Cell Surface Interaction Assays

In some aspects of the invention, the protein-protein interaction assay is a cell surface interaction assay. In this type of assay, one or more prey proteins (e.g., one or more STM receptors, e.g., CNTN1, IL12RB1, or IL1RAPL2) are expressed as extracellular domain (ECD) fusion proteins on the cell surface and are tested for interaction with one or more bait proteins (e.g., the SARS-CoV-2 S protein RBD) expressed as a soluble construct using, e.g., a fluorescent assay wherein the bait protein comprises a fluorescent tag.

In some aspects, the prey protein or prey proteins comprise one or more fusion proteins in which the extracellular domain (ECD) of a prey protein of interest (e.g., CNTN1, IL12RB1, or IL1RAPL2) is conjugated (e.g., fused) to one or more additional moieties (e.g., a glycosylphosphatidylinositol (GPI)-gD (gDGPI) tag) such that the prey fusion protein is expressed on the cell surface.

In some aspects in which the polypeptide comprises an extracellular domain, a tag, and an anchor, the anchor is capable of tethering the extracellular domain to the surface of a plasma membrane of a cell. In some aspects, the anchor is a glycosylphosphatidyl-inositol (GPI) polypeptide. In some aspects, the anchor is a moiety used in protein lipidation, e.g., a moiety used in cysteine palmitoylation, glycine myristoylation, lysine fatty-acylation, cholesterol esterification, cysteine prenylation, or serine fatty-acylation.

In some aspects, the tag can be directly or indirectly visualized, or otherwise detected. For example, the tag may comprise a moiety that can be detected using an antibody or an antibody fragment, e.g., may be a glycoprotein D (gD) polypeptide. In some aspects, the tag comprises a fluorescent protein.

The bait protein (e.g., the SARS-CoV-2 S protein RBD) may be conjugated to one or more additional moieties such that the bait fusion protein is soluble. The additional moiety or moieties may also increase the avidity of the bait fusion protein for the prey protein, e.g., by multimerizing the bait protein. Increasing avidity may increase the detection of low-affinity interactions. In some aspects, the additional moiety causes tetramerization of the bait protein (e.g., the SARS-CoV-2 S protein RBD).

In some aspects, the bait fusion protein comprises an Avi tag, a cleavage sequence (e.g., a TEV cleavage sequence), and an Fc tag, such that the Fc tag can be cleaved from the protein upon addition of the enzyme TEV protease. To prepare this protein for a cell surface interaction assay, the Fc tag is cleaved, the Avi tag is biotinylated, and the biotinylated bait fusion protein is conjugated to a fluorescent streptavidin (SA), e.g., a streptavidin conjugated to allophycocyanin (APC), to form a tetramerized bait fusion protein detectable in a fluorescence assay.

The prey fusion protein (e.g., CNTN1, IL12RB1, or IL1RAPL2 or the ECD thereof) may be expressed (e.g., transfected, e.g., transiently transfected) in a cell. The cell may be a human cell, e.g., a COS7 cell. Transfected cells may be placed in a well, e.g., a well in a 384-well plate.

The bait fusion protein ((e.g., the SARS-CoV-2 S protein RBD) may be expressed (e.g., transfected, e.g., transiently transfected) in a cell, e.g., a mammalian cell. Bait fusion proteins may be purified using standard protocols, e.g., as described in Ramani et al., *Anal Biochem,* 420: 127-138, 2012.

To perform the protein-protein interaction assay, a solution comprising the bait protein (e.g., the purified bait fusion protein conjugated to fluorescent SA) may be added to one or more wells containing cells expressing a prey protein (e.g., to one or more wells of a 384-well plate). The assay may then be incubated and washed one or more times to remove non-bound bait protein. The cells may then be fixed, e.g., with 4% paraformaldehyde, to preserve protein-protein interactions.

In some aspects, detecting an interaction comprises detecting a signal, e.g., a fluorescent signal, at a location on the solid surface that is above a threshold level (e.g., a signal indicating the presence of a query protein at the location, e.g., a signal from a moiety comprised by the bait fusion protein (e.g., multimerized query protein)). The signal may be directly or indirectly visualizable or otherwise detectable. In some aspects, the detecting is semi-automated or automated. The interaction may be a transient interaction and/or a low-affinity interaction, e.g., a micromolar-affinity interaction.

In aspects in which the bait fusion protein (e.g., a multimerized query protein) comprises a fluorescent SA, interaction between the bait fusion protein and the prey fusion protein may be detected by fluorescence microscopy. Relatively high fluorescence indicates that the bait fusion protein is present, i.e., that the bait fusion protein and the prey fusion protein interact.

Extracellular Interaction Assays

In some aspects of the invention, the protein-protein interaction assay is an extracellular interaction assay, e.g., an avidity-based extracellular interaction screen (AVEXIS) (Bushell et al., *Genome Res,* 18: 622-630, 2008; Martinez-Martin et al., *J Immunol Res,* 2197615, 2017).

SPR Assays for Modulation of Protein-Protein Interaction

In some aspects, the assay for protein-protein interaction is a surface plasmon resonance (SPR) assay. In some aspects, SPR assays are used to confirm or validate assays detected in an extracellular interaction assay or a cell surface interaction assay, e.g., a high-throughput extracellular interaction screen or a high-throughput cell surface interaction screen.

In some aspects, a prey protein is expressed as a fusion protein comprising the extracellular domain (ECD) of the protein conjugated to an additional moiety, e.g., an Fc tag. The prey fusion protein may be purified. The prey protein may be immobilized on a sensor chip, e.g. a GLC or CM5 sensor chip, by amine coupling.

The bait protein may be provided in a soluble form, e.g., as a protein domain (e.g., the SARS-CoV-2 S protein RBD) fused to a soluble tag. The bait fusion protein may be purified.

In some aspects, modulation of the binding of CNTN1, IL12RB1, or IL1RAPL2 and the SARS-CoV-2 S protein is measured as a difference in SPR signal response units (RU) in the presence compared to the absence of the modulator.

BLI Assays for Modulation of Protein-Protein Interaction

In some aspects, the assay for protein-protein interaction is a biolayer interferometry (BLI) assay. In some aspects, the BLI assay is performed using isolated ECDs, e.g., isolated ECDs as described herein, and the SARS-CoV-2 S protein RBD. In some aspects, modulation of the binding of CNTN1, IL12RB1, or IL1RAPL2 and the SARS-CoV-2 S protein RBD is measured as a difference in wavelength shift ($\Delta\lambda$) measured at a biosensor tip in the presence compared to the absence of the modulator.

ELISA for Modulation of Protein-Protein Interaction

In some aspects, the assay for protein-protein interaction is an enzyme-linked immunosorbent assay (ELISA). In some aspects, a first protein is bound to a plate (e.g., directly bound to a plate or bound to a plate via an affinity tag recognized by an antibody bound to a plate) and a second protein is provided in a soluble form, e.g., as an isolated ECD as described herein. An interaction between the first protein and the second protein may be detected by providing an antibody that binds to the second protein or to an affinity tag thereof, wherein the antibody can be detected, e.g., visualized, in an assay for presence of the antibody.

Other Assays for Modulation of Protein-Protein Interaction

In some aspects, the assay is an isothermal titration calorimetry (ITC) assay, an assay comprising immunoprecipitation, or an assay comprising an ALPHASCREEN™ technology.

In some aspects of the above assays, the candidate modulator is provided to a cell (e.g., a mammalian cell), to cell culture media, to conditioned media, and/or to a purified form of CNTN1, IL12RB1, or IL1RAPL2 and/or the SARS-CoV-2 S protein. In some aspects, the candidate modulator is provided at a concentration of at least 0.1 nM, 0.5 nM, 1 nM, 10 nM, 50 nM, 100 nM, 250 nM, 500 nM, 750 nM, 1 µM, 2 µM, 3 µM, 5 µM, or 10 µM. In some aspects, the candidate modulator is provided at a concentration of between 0.1 nM and 10 µM. In some aspects, the candidate modulator is provided in a solution, e.g., in a soluble form.

In some aspects, the candidate modulator is identified as a modulator if the increase in binding is at least 50%. In some aspects, the increase in binding is at least 5%, at least 10%, at least 20%, at least 30%, at least 40%, at least 50%, at least 60%, at least 70%, at least 80%, at least 90%, at least 100%, or more than 100% (e.g., 5%-15%, 15%-25%, 25%-35%, 35%-45%, 45%-55%, 55%-65%, 65%-75%, 75%-85%, 85%-95%, 95%-100%, or more than 100%). In some aspects, the increase in binding is at least 50%.

In some aspects, the candidate modulator is identified as a modulator if the decrease in binding is at least 50%. In some aspects, the decrease in binding is at least 5%, at least 10%, at least 20%, at least 30%, at least 40%, at least 50%, at least 60%, at least 70%, at least 80%, at least 90%, or 100% (e.g., 5%-15%, 15%-25%, 25%-35%, 35%-45%, 45%-55%, 55%-65%, 65%-75%, 75%-85%, 85%-95%, or 95%-100%). In some aspects, the decrease in binding is at least 50%.

Exemplary methods for identifying modulators of protein-protein interactions, as well as agents that may modulate such interactions, are described in PCT/US2020/025471, which is hereby incorporated by reference.

III. Modulators of Protein-Protein Interactions

A. Modulators of the Interaction Between the SARS-CoV-2 S Protein and CNTN1

In some aspects, the disclosure features an isolated modulator of the interaction between the SARS-CoV-2 S protein (e.g., the SARS-CoV-2 S protein RBD) and CNTN1, wherein the modulator causes a decrease in the binding of the SARS-CoV-2 S protein to CNTN1 relative to binding in the absence of the modulator.

In some aspects, the decrease in binding is at least 5%, 10%, 15%, 20%, 25%, 30%, 35%, 40%, 45%, 50%, 55%, 60%, 65%, 70%, 75%, 80%, 85%, 90%, 95%, 98%, or 99% or is 100% (i.e., binding is abolished), e.g., the decrease is 5%-15%, 15%-25%, 25%-35%, 35%-45%, 45%-55%, 55%-65%, 65%-75%, 75%-85%, 85%-95%, or 95%-100%, relative to binding in the absence of the modulator. In some aspects, the decrease in binding is at least 50%, e.g., as measured by surface plasmon resonance, biolayer interferometry, or an enzyme-linked immunosorbent assay (ELISA).

In some aspects, the disclosure features an isolated modulator of the downstream activity of the SARS-CoV-2 S protein or CNTN1, wherein the modulator causes a change in the downstream activity of the SARS-CoV-2 S protein or CNTN1 relative to downstream activity in the absence of the modulator.

In some aspects, the change in the downstream activity is a decrease in the amount, strength, or duration of the downstream activity. In some aspects, the downstream activity of the SARS-CoV-2 S protein or CNTN1 is infection of a cell by SARS-CoV-2.

In some aspects, the modulator is a small molecule, an antibody or antigen-binding fragment thereof, a peptide, a mimic, or an inhibitory nucleic acid (e.g., ASO or a siRNA). Modulators are further described below.

B. Modulators of the Interaction Between the SARS-CoV-2 S Protein and IL12RB1

In some aspects, the disclosure features an isolated modulator of the interaction between the SARS-CoV-2 S protein (e.g., the SARS-CoV-2 S protein) and IL12RB1, wherein the modulator causes a decrease in the binding of the SARS-CoV-2 S protein to IL12RB1 relative to binding in the absence of the modulator.

In some aspects, the decrease in binding is at least 5%, 10%, 15%, 20%, 25%, 30%, 35%, 40%, 45%, 50%, 55%, 60%, 65%, 70%, 75%, 80%, 85%, 90%, 95%, 98%, or 99% or is 100% (i.e., binding is abolished), e.g., the decrease is 5%-15%, 15%-25%, 25%-35%, 35%-45%, 45%-55%, 55%-65%, 65%-75%, 75%-85%, 85%-95%, or 95%-100%, relative to binding in the absence of the modulator. In some aspects, the decrease in binding is at least 50%, e.g., as measured by surface plasmon resonance, biolayer interferometry, or an enzyme-linked immunosorbent assay (ELISA).

In some aspects, the disclosure features an isolated modulator of the downstream activity of the SARS-CoV-2 S protein or IL12RB1, wherein the modulator causes a change in the downstream activity of the SARS-CoV-2 S protein or IL12RB1 relative to downstream activity in the absence of the modulator. In some aspects, the change in the downstream activity is a decrease in the amount, strength, or duration of the downstream activity. In some aspects, the downstream activity of the SARS-CoV-2 S protein or IL12RB1 is infection of a cell by SARS-CoV-2.

In some aspects, the modulator is a small molecule, an antibody or antigen-binding fragment thereof, a peptide, a mimic, or an inhibitory nucleic acid (e.g., ASO or a siRNA). Modulators are further described below.

C. Modulators of the Interaction Between the SARS-CoV-2 S Protein and IL1RAPL2

In some aspects, the disclosure features an isolated modulator of the interaction between the SARS-CoV-2 S protein (e.g., the SARS-CoV-2 S protein) and IL1RAPL2, wherein the modulator causes a decrease in the binding of the SARS-CoV-2 S protein to IL1RAPL2 relative to binding in the absence of the modulator.

In some aspects, the decrease in binding is at least 5%, 10%, 15%, 20%, 25%, 30%, 35%, 40%, 45%, 50%, 55%, 60%, 65%, 70%, 75%, 80%, 85%, 90%, 95%, 98%, or 99% or is 100% (i.e., binding is abolished), e.g., the decrease is 5%-15%, 15%-25%, 25%-35%, 35%-45%, 45%-55%, 55%-65%, 65%-75%, 75%-85%, 85%-95%, or 95%-100%, relative to binding in the absence of the modulator. In some aspects, the decrease in binding is at least 50%, e.g., as measured by surface plasmon resonance, biolayer interferometry, or an enzyme-linked immunosorbent assay (ELISA).

In some aspects, the disclosure features an isolated modulator of the downstream activity of the SARS-CoV-2 S protein or IL1RAPL2, wherein the modulator causes a change in the downstream activity of the SARS-CoV-2 S protein or IL1RAPL2 relative to downstream activity in the absence of the modulator.

In some aspects, the change in the downstream activity is a decrease in the amount, strength, or duration of the downstream activity. In some aspects, the downstream activity of the SARS-CoV-2 S protein or IL1RAPL2 is infection of a cell by SARS-CoV-2.

In some aspects, the modulator is a small molecule, an antibody or antigen-binding fragment thereof, a peptide, a mimic, or an inhibitory nucleic acid (e.g., ASO or a siRNA). Modulators are further described below.

D. Small Molecules

In some aspects, the modulator or candidate modulator is a small molecule. Small molecules are molecules other than binding polypeptides or antibodies as defined herein that may bind, preferably specifically, to CNTN1, IL12RB1, or IL1RAPL2 and/or the SARS-CoV-2 S protein. Binding small molecules may be identified and chemically synthesized using known methodology (see, e.g., PCT Publication Nos. WO00/00823 and WO00/39585). Binding small molecules are usually less than about 2000 daltons in size (e.g., less than about 2000, 1500, 750, 500, 250 or 200 daltons in size), wherein such organic small molecules that are capable of binding, preferably specifically, to a polypeptide as described herein may be identified without undue experimentation using well known techniques. In this regard, it is noted that techniques for screening small molecule libraries for molecules that are capable of binding to a polypeptide target are well known in the art (see, e.g., PCT Publication Nos. WO00/00823 and WO00/39585). Binding small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

In some aspects, the binding of the SARS-CoV-2 S protein and CNTN1, IL12RB1, or IL1RAPL2 is decreased (e.g., decreased by 5%, 10%, 20%, 30%, 40%, 50%, 60%, 70%, 80%, 90%, or 100%, e.g., decreased by 5%-15%, 15%-25%, 25%-35%, 35%-45%, 45%-55%, 55%-65%, 65%-75%, 75%-85%, 85%-95%, or 95%-100%) in the presence of the small molecule. In some aspects, the binding of the SARS-CoV-2 S protein and CNTN1, IL12RB1, or IL1RAPL2 is increased (e.g., increased by 5%, 10%, 20%, 30%, 40%, 50%, 60%, 70%, 80%, 90%, 100%, or more than 100%, e.g., increased by 5%-15%, 15%-25%, 25%-35%, 35%-45%, 45%-55%, 55%-65%, 65%-75%, 75%-85%, 85%-95%, 95%-100%, or more than 100%) in the presence of the small molecule. In some aspects, a downstream activity (e.g., infection of a cell by SARS-CoV-2) of SARS-CoV-2 S protein and/or CNTN1, IL12RB1, or IL1RAPL2 is decreased (e.g., decreased by 5%, 10%, 20%, 30%, 40%, 50%, 60%, 70%, 80%, 90%, or 100%, e.g., decreased by 5%-15%, 15%-25%, 25%-35%, 35%-45%, 45%-55%, 55%-65%, 65%-75%, 75%-85%, 85%-95%, or 95%-100%) in the presence of the small molecule.

E. Antibodies and Antigen-Binding Fragments

In some aspects, the modulator or candidate modulator is an antibody or an antigen-binding fragment thereof binding CNTN1, IL12RB1, or IL1RAPL2 and/or the SARS-CoV-2 S protein (e.g., the SARS-CoV-2 S protein RBD). In some aspects, the antigen-binding fragment is a bis-Fab, an Fv, a Fab, a Fab'-SH, a F(ab')₂, a diabody, a linear antibody, an scFv, an ScFab, a VH domain, or a VHH domain.

In some aspects, the modulator is an antibody or antigen-binding fragment thereof that binds the SARS-CoV-2 S protein (e.g., binds the SARS-CoV-2 S protein RBD), e.g., binds to an epitope of the SARS-CoV-2 S protein that interacts with CNTN1, IL12RB1, or IL1RAPL2. In some aspects, the antibody or antigen-binding fragment thereof that binds the SARS-CoV-2 S protein blocks the interaction of the SARS-CoV-2 S protein with CNTN1, IL12RB1, or IL1RAPL2, e.g., blocks the interaction of the SARS-CoV-2 S protein with CNTN1, IL12RB1, or IL1RAPL2.

In some aspects, the modulator is an antibody or antigen-binding fragment thereof that binds CNTN1, IL12RB1, or IL1RAPL2, e.g., binds to an epitope of CNTN1, IL12RB1, or IL1RAPL2 that interacts with the SARS-CoV-2 S protein (e.g., interacts with the SARS-CoV-2 S protein RBD). In some aspects, the antibody or antigen-binding fragment thereof that binds CNTN1, IL12RB1, or IL1RAPL2 blocks the interaction of CNTN1, IL12RB1, or IL1RAPL2 with the SARS-CoV-2 S protein, e.g., blocks the interaction of CNTN1, IL12RB1, or IL1RAPL2 with the SARS-CoV-2 S protein RBD.

In some aspects, the modulator is a multispecific antibody, e.g., a bispecific antibody. In some aspects, the modulator is a bispecific antibody binds ACE2 and CNTN1; ACE2 and IL12RB1; or ACE2 and IL1RAPL2.

In some aspects, the binding of the SARS-CoV-2 S protein and CNTN1, IL12RB1, or IL1RAPL2 is decreased (e.g., decreased by 5%, 10%, 20%, 30%, 40%, 50%, 60%, 70%, 80%, 90%, or 100%, e.g., decreased by 5%-15%, 15%-25%, 25%-35%, 35%-45%, 45%-55%, 55%-65%, 65%-75%, 75%-85%, 85%-95%, or 95%-100%) in the presence of the antibody or antigen-binding fragment. In some aspects, the binding of the SARS-CoV-2 S protein and CNTN1, IL12RB1, or IL1RAPL2 is increased (e.g., increased by 5%, 10%, 20%, 30%, 40%, 50%, 60%, 70%, 80%, 90%, 100%, or more than 100%, e.g., increased by 5%-15%, 15%-25%, 25%-35%, 35%-45%, 45%-55%, 55%-65%, 65%-75%, 75%-85%, 85%-95%, 95%-100%, or more than 100%) in the presence of the antibody or antigen-binding fragment. In some aspects, a downstream activity (e.g., infection of a cell by SARS-CoV-2) of SARS-CoV-2 S protein and/or CNTN1, IL12RB1, or IL1RAPL2 is decreased (e.g., decreased by 5%, 10%, 20%, 30%, 40%, 50%, 60%, 70%, 80%, 90%, or 100%, e.g., decreased by 5%-15%, 15%-25%, 25%-35%, 35%-45%, 45%-55%, 55%-65%, 65%-75%, 75%-85%, 85%-95%, or 95%-100%) in the presence of the antibody or antigen-binding fragment.

F. Peptides

In some aspects, the modulator or candidate modulator is a peptide that binds to CNTN1, IL12RB1, or IL1RAPL2 and/or the SARS-CoV-2 S protein. The peptide may be the peptide may be naturally occurring or may be engineered. In some aspects, the peptide is a fragment of CNTN1, IL12RB1, or IL1RAPL2 or the SARS-CoV-2 S protein (e.g., the SARS-CoV-2 S protein RBD), or another protein that binds to CNTN1, IL12RB1, or IL1RAPL2 or the SARS-CoV-2 S protein. The peptide may bind the binding partner with equal, less, or greater affinity than the full-length protein. In some aspects, the peptide performs all functions of the full-length protein. In other aspects, the peptide does not perform all functions of the full-length protein.

In some aspects, the binding of the SARS-CoV-2 S protein and CNTN1, IL12RB1, or IL1RAPL2 is decreased (e.g., decreased by 5%, 10%, 20%, 30%, 40%, 50%, 60%, 70%, 80%, 90%, or 100%, e.g., decreased by 5%-15%, 15%-25%, 25%-35%, 35%-45%, 45%-55%, 55%-65%, 65%-75%, 75%-85%, 85%-95%, or 95%-100%) in the presence of the peptide. In some aspects, the binding of the SARS-CoV-2 S protein and CNTN1, IL12RB1, or IL1RAPL2 is increased (e.g., increased by 5%, 10%, 20%, 30%, 40%, 50%, 60%, 70%, 80%, 90%, 100%, or more than 100%, e.g., increased by 5%-15%, 15%-25%, 25%-35%, 35%-45%, 45%-55%, 55%-65%, 65%-75%, 75%-85%, 85%-95%, 95%-100%, or more than 100%) in the presence of the peptide. In some aspects, a downstream activity of the SARS-CoV-2 S protein and/or CNTN1, IL12RB1, or IL1RAPL2 (e.g., infection of a cell by SARS-CoV-2) is decreased (e.g., decreased by 5%, 10%, 20%, 30%, 40%, 50%, 60%, 70%, 80%, 90%, or 100%, e.g., decreased by 5%-15%, 15%-25%, 25%-35%, 35%-45%, 45%-55%, 55%-65%, 65%-75%, 75%-85%, 85%-95%, or 95%-100%) in the presence of the peptide.

G. Mimics

In some aspects, the modulator or candidate modulator is a mimic, e.g., a molecular mimic, that binds to CNTN1, IL12RB1, or IL1RAPL2 and/or the SARS-CoV-2 S protein. The mimic may be a molecular mimic of the SARS-CoV-2 S protein (e.g., the SARS-CoV-2 S protein RBD), CNTN1, IL12RB1, or IL1RAPL2, or another protein that binds to the SARS-CoV-2 S protein or CNTN1, IL12RB1, or IL1RAPL2. In some aspects, the mimic may perform all functions of the mimicked polypeptide. In other aspects, the mimic does not perform all functions of the mimicked polypeptide.

In some aspects, the binding of the SARS-CoV-2 S protein and CNTN1, IL12RB1, or IL1RAPL2 is decreased (e.g., decreased by 5%, 10%, 20%, 30%, 40%, 50%, 60%, 70%, 80%, 90%, or 100%, e.g., decreased by 5%-15%, 15%-25%, 25%-35%, 35%-45%, 45%-55%, 55%-65%, 65%-75%, 75%-85%, 85%-95%, or 95%-100%) in the presence of the mimic. In some aspects, the binding of the SARS-CoV-2 S protein and CNTN1, IL12RB1, or IL1RAPL2 increased (e.g., increased by 5%, 10%, 20%, 30%, 40%, 50%, 60%, 70%, 80%, 90%, 100%, or more than 100%, e.g., increased by 5%-15%, 15%-25%, 25%-35%, 35%-45%, 45%-55%, 55%-65%, 65%-75%, 75%-85%, 85%-95%, 95%-100%, or more than 100%) in the presence of the mimic. In some aspects, a downstream activity of the SARS-CoV-2 S protein and/or CNTN1, IL12RB1, or IL1RAPL2 (e.g., infection of a cell by SARS-CoV-2) is decreased (e.g., decreased by 5%, 10%, 20%, 30%, 40%, 50%, 60%, 70%, 80%, 90%, or 100%, e.g., decreased by 5%-15%, 15%-25%, 25%-35%, 35%-45%, 45%-55%, 55%-65%, 65%-75%, 75%-85%, 85%-95%, or 95%-100%) in the presence of the mimic.

IV. Methods of Treating or Preventing SARS-COV-2 Infections

A. Methods of Treating Individuals Having SARS-CoV-2 Infections

In some aspects, the disclosure features a method of treating an individual having a SARS-CoV-2 infection comprising administering to the individual an effective amount of a contactin-1 (CNTN1) antagonist, an interleukin 12 receptor subunit beta 1 (IL12RB1) antagonist, or an interleukin 1 receptor accessory protein like 2 (IL1RAPL2) antagonist.

In some aspects, the disclosure features a method of decreasing SARS-CoV-2 infection in an individual comprising administering to the individual an effective amount of a CNTN1 antagonist, an IL12RB1 antagonist, or an IL1RAPL2 antagonist.

In some aspects, the disclosure features a method of reducing SARS-CoV-2 attachment to a cell of an individual comprising administering to the individual an effective amount of a CNTN1 antagonist, an IL12RB1 antagonist, or an IL1RAPL2 antagonist.

In some aspects, the administering comprises contacting the cell of the individual with an effective amount of a CNTN1 antagonist, an IL12RB1 antagonist, or an IL1RAPL2 antagonist.

In some aspects, (a) the CNTN1 antagonist results in a decrease in the binding of CNTN1 and the SARS-CoV-2 spike (S) protein relative to binding of the two proteins in the absence of the antagonist; (b) the IL12RB1 antagonist results in a decrease in the binding of IL12RB1 and the SARS-CoV-2 S protein relative to binding of the two proteins in the absence of the antagonist; or (c) the IL1RAPL2 antagonist results in a decrease in the binding of IL1RAPL2 and the SARS-CoV-2 S protein relative to binding of the two proteins in the absence of the antagonist. In some aspects, the decrease in binding is at least 5%, at least 10%, at least 20%, at least 30%, at least 40%, at least 50%, at least 60%, at least 70%, at least 80%, at least 90%, or 100% (e.g., 5%-15%, 15%-25%, 25%-35%, 35%-45%, 45%-55%, 55%-65%, 65%-75%, 75%-85%, 85%-95%, or 95%-100%). In some aspects, the decrease in binding is at least 40%.

In some aspects, the CNTN1 antagonist, IL12RB1 antagonist, or IL1RAPL2 antagonist reduces the extent and/or severity of SARS-CoV-2 infection of the individual relative to infection in the absence of the CNTN1 antagonist, IL12RB1 antagonist, or IL1RAPL2 antagonist, respectively.

In some aspects, the CNTN1 antagonist, IL12RB1 antagonist, or IL1RAPL2 antagonist is a small molecule, an antibody or antigen-binding fragment thereof, a peptide, a mimic, or an inhibitory nucleic acid.

In some aspects, the inhibitory nucleic acid is an antisense oligonucleotide (ASO) or a small interfering RNA (siRNA).

In some aspects, the CNTN1 antagonist, IL12RB1 antagonist, or IL1RAPL2 antagonist is a peptide.

In some aspects, the CNTN1 antagonist, IL12RB1 antagonist, or IL1RAPL2 antagonist is an antibody or antigen-binding fragment thereof. In some aspects, the antibody or antigen-binding fragment thereof binds the SARS-CoV-2 S protein and inhibits its binding to CNTN1, IL12RB1, and/or IL1RAPL2. In some aspects, the antibody or antigen-binding fragment thereof binds CNTN1, IL12RB1, or IL1RAPL2. In some aspects, the antibody or antigen-binding fragment thereof inhibits the binding of CNTN1, IL12RB1, or IL1RAPL2 to the SARS-CoV-2 S protein. In some aspects, the antibody or antigen-binding fragment thereof inhibits the binding of CNTN1, IL12RB1, or IL1RAPL2 to the SARS-CoV-2 S protein receptor binding domain (RBD). In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody is a bispecific antibody. In some aspects, the bispecific antibody binds (a) angiotensin-converting enzyme 2 (ACE2) and CNTN1; (b) ACE2 and IL12RB1; or (c) ACE2 and IL1RAPL2.

In some aspects, the individual has COVID-19. In some aspects, the individual has pneumonia (e.g., viral pneumonia, e.g., COVID-19 pneumonia) or acute respiratory distress syndrome (ARDS).

B. Methods of Prophylaxis Against Secondary SARS-CoV-2 Infection of Nervous Tissue In some aspects, the disclosure features a method of prophylaxis against secondary infection of a tissue of the nervous system (e.g., one or more of brain tissue, choroid plexus, amygdala, basal ganglia, cerebellum, frontal cortex, parenchyma, cerebral cortex, corpus callosum, hippocampal formation, hypothalamus, midbrain, pons and medulla, spinal cord, substantia nigra, ependymal cells, nervous system cells, and associated tissues such as the olfactory epithelium) in an individual having a SARS-CoV-2 infection comprising administering to the individual an effective amount of a CNTN1 antagonist or an IL1RAPL2 antagonist. In some aspects, the tissue of the nervous system is choroid plexus (e.g., epithelial, mesenchymal, ependymal, monocyte, neural, glial, or endothelial cells of the choroid plexus). In some aspects, the tissue of the nervous system is cortex parenchyma (e.g., oligodendrocyte, excitatory neuron, astrocyte, OPC, microglia, interneuron, radial glia, or maturing neuron cells of the cortex parenchyma). In some aspects, the tissue of the nervous system is olfactory epithelium. In some aspects, secondary infection of nervous tissue in patients having a SARS-CoV-2 infection (e.g., a SARS-CoV-2 infection of the respiratory tract, e.g., the upper respiratory tract) is decreased or eliminated in patients treated according to the above-described methods relative to untreated patients or relative to patients treated using a control method (e.g., SOC), e.g., decreased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% (e.g., decreased by 5%-15%, 15%-25%, 25%-35%, 35%-45%, 45%-55%, 55%-65%, 65%-75%, 75%-85%, 85%-95%, or 95%-100%).

In some aspects, (a) the CNTN1 antagonist results in a decrease in the binding of CNTN1 and the SARS-CoV-2 S protein relative to binding of the two proteins in the absence of the antagonist; or (b) the IL1RAPL2 antagonist results in a decrease in the binding of IL1RAPL2 and the SARS-CoV-2 S protein relative to binding of the two proteins in the absence of the antagonist. In some aspects, the decrease in binding is at least 5%, at least 10%, at least 20%, at least 30%, at least 40%, at least 50%, at least 60%, at least 70%, at least 80%, at least 90%, or 100% (e.g., 5%-15%, 15%-25%, 25%-35%, 35%-45%, 45%-55%, 55%-65%, 65%-75%, 75%-85%, 85%-95%, or 95%-100%). In some aspects, the decrease in binding is at least 40%.

In some aspects, the CNTN1 antagonist or IL1RAPL2 antagonist reduces the extent and/or severity of SARS-CoV-2 infection of nervous tissue in the individual relative to infection in the absence of the CNTN1 antagonist or IL1RAPL2 antagonist, respectively. In some aspects, the extent and/or severity of SARS-CoV-2 infection of nervous tissue in patients having a SARS-CoV-2 infection (e.g., a SARS-CoV-2 infection of the respiratory tract, e.g., the upper respiratory tract) is decreased in patients treated according to the above-described methods relative to untreated patients or relative to patients treated using a control method (e.g., SOC), e.g., decreased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% (e.g., decreased by 5%-15%, 15%-25%, 25%-35%, 35%-45%, 45%-55%, 55%-65%, 65%-75%, 75%-85%, 85%-95%, or 95%-100%).

In some aspects, the CNTN1 antagonist or IL1RAPL2 antagonist is a small molecule, an antibody or antigen-binding fragment thereof, a peptide, a mimic, or an inhibitory nucleic acid.

In some aspects, the inhibitory nucleic acid is an ASO or a siRNA.

In some aspects, the CNTN1 antagonist or IL1RAPL2 antagonist is a peptide.

In some aspects, the CNTN1 antagonist or IL1RAPL2 antagonist is an antibody or antigen-binding fragment thereof.

In some aspects, the antibody or antigen-binding fragment thereof binds the SARS-CoV-2 S protein and inhibits its binding to CNTN1 and/or IL1RAPL2. In some aspects, the antibody or antigen-binding fragment thereof binds CNTN1 or IL1RAPL2.

In some aspects, the antibody or antigen-binding fragment thereof inhibits the binding of CNTN1 or IL1RAPL2 to the SARS-CoV-2 S protein. In some aspects, the antibody or antigen-binding fragment thereof inhibits the binding of CNTN1 or IL1RAPL2 to the SARS-CoV-2 S protein RBD. In some aspects, the antigen-binding fragment is a bis-Fab, an Fv, a Fab, a Fab'-SH, a F(ab')₂, a diabody, a linear antibody, an scFv, an scFab, a VH domain, or a VHH domain.

In some aspects, the antibody is a bispecific antibody. In some aspects, the bispecific antibody binds (a) ACE2 and CNTN1 or (b) ACE2 and IL1RAPL2. In some aspects, the bispecific antibody binds CNTN1 and IL1RAPL2.

In some aspects, the individual has COVID-19. In some aspects, the individual has pneumonia (e.g., viral pneumonia, e.g., COVID-19 pneumonia) or acute respiratory distress syndrome (ARDS). In some aspects, the individual is a human.

C. Methods of Prophylaxis Against Secondary SARS-CoV-2 Infection of Immune Cells and Lymphoid Tissue In some aspects, the disclosure features a method of prophylaxis against secondary infection of immune cells and/or lymphoid tissue (e.g., one or more of B-cells, dendritic cells, granulocytes, monocytes, natural killer cells, T-cells, and total peripheral blood mononuclear cells (PMBCs)) in an individual having a SARS-CoV-2 infection comprising administering to the individual an effective amount of an IL12RB1 antagonist. In some aspects, secondary infection of immune cells and/or lymphoid tissue in patients having a SARS-CoV-2 infection (e.g., a SARS-CoV-2 infection of the respiratory tract, e.g., the upper respiratory tract) is decreased or eliminated in patients treated according to the above-described methods relative to untreated patients or relative to patients treated using a control method (e.g., SOC), e.g., decreased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% (e.g., decreased by 5%-15%, 15%-25%, 25%-35%, 35%-45%, 45%-55%, 55%-65%, 65%-75%, 75%-85%, 85%-95%, or 95%-100%).

In some aspects, the IL12RB1 antagonist results in a decrease in the binding of IL12RB1 and the SARS-CoV-2 S protein relative to binding of the two proteins in the absence of the antagonist. In some aspects, the decrease in binding is at least 5%, at least 10%, at least 20%, at least 30%, at least 40%, at least 50%, at least 60%, at least 70%, at least 80%, at least 90%, or 100%. In some aspects, the decrease in binding is at least 40% (e.g., 5%-15%, 15%-25%, 25%-35%, 35%-45%, 45%-55%, 55%-65%, 65%-75%, 75%-85%, 85%-95%, or 95%-100%).

In some aspects, the IL12RB1 antagonist reduces the extent and/or severity of SARS-CoV-2 infection of immune cells and/or lymphoid tissue in the individual relative to infection in the absence of the IL12RB1 antagonist. In some aspects, the extent and/or severity of SARS-CoV-2 infection of immune cells and/or lymphoid tissue in patients having a SARS-CoV-2 infection (e.g., a SARS-CoV-2 infection of the respiratory tract, e.g., the upper respiratory tract) is decreased in patients treated according to the above-described methods relative to untreated patients or relative to patients treated using a control method (e.g., SOC), e.g., decreased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% (e.g., decreased by 5%-15%, 15%-25%, 25%-35%, 35%-45%, 45%-55%, 55%-65%, 65%-75%, 75%-85%, 85%-95%, or 95%-100%).

In some aspects, the IL12RB1 antagonist is a small molecule, an antibody or antigen-binding fragment thereof, a peptide, a mimic, or an inhibitory nucleic acid. In some aspects, the inhibitory nucleic acid is an ASO or a siRNA.

In some aspects, the IL12RB1 antagonist is a peptide.

In some aspects, the IL12RB1 antagonist is an antibody or antigen-binding fragment thereof.

In some aspects, the antibody or antigen-binding fragment thereof binds the SARS-CoV-2 S protein and inhibits its binding to IL12RB1. In some aspects, the antibody or antigen-binding fragment thereof binds IL12RB1. In some aspects, the antibody or antigen-binding fragment thereof inhibits the binding of IL12RB1 to the SARS-CoV-2 S protein. In some aspects, the antibody or antigen-binding fragment thereof inhibits the binding of IL12RB1 to the SARS-CoV-2 S protein RBD. In some aspects, the antigen-binding fragment is a bis-Fab, an Fv, a Fab, a Fab'-SH, a F(ab')2, a diabody, a linear antibody, an scFv, an scFab, a VH domain, or a VHH domain.

In some aspects, the antibody is a bispecific antibody. In some aspects, the bispecific antibody binds ACE2 and IL12RB1.

In some aspects, the individual has COVID-19. In some aspects, the individual has pneumonia (e.g., viral pneumonia, e.g., COVID-19 pneumonia) or acute respiratory distress syndrome (ARDS). In some aspects, the individual is a human.

D. Methods of Prophylaxis Against Secondary SARS-CoV-2 Infection of the Lungs

In some aspects, the disclosure features a method of prophylaxis against secondary infection of the lungs in an individual having a SARS-CoV-2 infection comprising administering to the individual an effective amount of a CNTN1 antagonist or an IL12RB1 antagonist. In some aspects, secondary infection of the lungs in patients having a SARS-CoV-2 infection (e.g., a SARS-CoV-2 infection of the upper respiratory tract) is decreased or eliminated in patients treated according to the above-described methods relative to untreated patients or relative to patients treated using a control method (e.g., SOC), e.g., decreased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% (e.g., decreased by 5%-15%, 15%-25%, 25%-35%, 35%-45%, 45%-55%, 55%-65%, 65%-75%, 75%-85%, 85%-95%, or 95%-100%).

In some aspects, (a) the CNTN1 antagonist results in a decrease in the binding of CNTN1 and the SARS-CoV-2 S protein relative to binding of the two proteins in the absence of the antagonist; or (b) the IL12RB1 antagonist results in a decrease in the binding of IL12RB1 and the SARS-CoV-2 S protein relative to binding of the two proteins in the absence of the antagonist. In some aspects, the decrease in binding is at least 5%, at least 10%, at least 20%, at least 30%, at least 40%, at least 50%, at least 60%, at least 70%, at least 80%, at least 90%, or 100% (e.g., 5%-15%, 15%-25%, 25%-35%, 35%-45%, 45%-55%, 55%-65%, 65%-75%, 75%-85%, 85%-95%, or 95%-100%). In some aspects, the decrease in binding is at least 40%.

In some aspects, the CNTN1 antagonist or IL12RB1 antagonist reduces the extent and/or severity of SARS-CoV-2 infection of the lungs in the individual relative to infection in the absence of the CNTN1 antagonist or IL12RB1 antagonist, respectively. In some aspects, the extent and/or severity of SARS-CoV-2 infection of the lungs in patients having a SARS-CoV-2 infection (e.g., a SARS-CoV-2 infection of the upper respiratory tract) is decreased in patients treated according to the above-described methods relative to untreated patients or relative to patients treated using a control method (e.g., SOC), e.g., decreased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% (e.g., decreased by 5%-15%, 15%-25%, 25%-35%, 35%-45%, 45%-55%, 55%-65%, 65%-75%, 75%-85%, 85%-95%, or 95%-100%).

In some aspects, the CNTN1 antagonist or IL12RB1 antagonist is a small molecule, an antibody or antigen-binding fragment thereof, a peptide, a mimic, or an inhibitory nucleic acid. In some aspects, the inhibitory nucleic acid is an ASO or a siRNA.

In some aspects, the CNTN1 antagonist or IL12RB1 antagonist is a peptide.

In some aspects, the CNTN1 antagonist or IL12RB1 antagonist is an antibody or antigen-binding fragment thereof. In some aspects, the antibody or antigen-binding fragment thereof binds the SARS-CoV-2 S protein and inhibits its binding to CNTN1 and/or IL12RB1. In some aspects, the antibody or antigen-binding fragment thereof binds CNTN1 or IL12RB1. In some aspects, the antibody or antigen-binding fragment thereof inhibits the binding of CNTN1 or IL12RB1 to the SARS-CoV-2 S protein. In some aspects, the antibody or antigen-binding fragment thereof inhibits the binding of CNTN1 or IL12RB1 to the SARS-CoV-2 S protein RBD. In some aspects, the antigen-binding fragment is a bis-Fab, an Fv, a Fab, a Fab'-SH, a F(ab')$_2$, a diabody, a linear antibody, an scFv, an scFab, a VH domain, or a VHH domain.

In some aspects, the antibody is a bispecific antibody. In some aspects, the bispecific antibody binds (a) ACE2 and CNTN1 or (b) ACE2 and IL12RB1. In some aspects, the bispecific antibody binds CNTN1 and IL12RB1.

In some aspects, the individual has COVID-19. In some aspects, the individual has pneumonia (e.g., viral pneumonia, e.g., COVID-19 pneumonia) or acute respiratory distress syndrome (ARDS). In some aspects, the individual is a human.

E. Combination Therapies

In some aspects of the above-described methods of treatment and prophylaxis, the method comprises administering to the individual at least one additional therapy (e.g., one, two, three, four, or more than four additional therapies). The CNTN1 antagonist, IL12RB1 antagonist, or IL1RAPL2 antagonist may be administered to the individual prior to, concurrently with, or after the at least one additional therapy.

In some aspects, the at least one additional therapy is an IL-6 antagonist, e.g., tocilizumab. In some aspects, the individual is administered a first weight-based 8 mg/kg intravenous dose of tocilizumab optionally followed by a second weight-based 8 mg/kg intravenous dose of tocilizumab 8-24 hours after the first dose.

In some aspects, the at least one additional therapy is an angiotensin-converting enzyme 2 (ACE2) antagonist. ACE2 antagonists may include, e.g., a small molecule, an antibody or antigen-binding fragment thereof, a peptide, a mimic, or an inhibitory nucleic acid (e.g., ASO or a siRNA) that reduces or inhibits a function of ACE2, e.g., reduces or inhibits ACE2 binding to the SARS Cov-2 S protein. Exemplary ACE2 proteins or fragments thereof for use as therapeutic agents are described in U.S. Pat. Nos. 9,561,263 and 10,443,049.

In some aspects, the at least one additional therapy is a neuropilin-2 (NRP2) antagonist. NRP2 antagonists may include, e.g., a small molecule, an antibody or antigen-binding fragment thereof, a peptide, a mimic, or an inhibitory nucleic acid (e.g., ASO or a siRNA) that reduces or inhibits a function of NRP2, e.g., reduces or inhibits NRP2 binding to the SARS Cov-2 S protein. Exemplary anti-NRP2 antibodies are described in U.S. Pat. No. 8,920,905.

In some aspects, the at least one additional therapy is a supportive care therapy (e.g., oxygen therapy), an anti-viral therapy (e.g., alpha-interferon, lopinavir, ritonavir, lopinavir/ritonavir, remdesivir, ribavirin, hydroxychloroquine, chloroquine, umifenovir, favipiravir, or a combination thereof), or a corticosteroid therapy (e.g., prednisone, prednisolone, methylprednisolone, methylprednisolone sodium succinate, dexamethasone, dexamethasone triamcinolone, hydrocortisone, betamethasone, or a combination thereof). In some aspects, the corticosteroid therapy is a low-dose corticosteroid therapy.

F. Clinical Outcomes

In some aspects of the above-described methods of treatment and prophylaxis, the method achieves a greater improvement in clinical outcome compared to standard of care (SOC). In some aspects, the clinical outcome is time to clinical improvement (TTCI) defined as a National Early Warning Score 2 (NEWS2) of ≤2 maintained for 24 hours. The NEWS2 score is described in Myrstad et al., *Scand J Trauma Resusc Emerg Med,* 28(66), 2020.

In some aspects, the clinical outcome is incidence of mechanical ventilation. In some aspects, the need for mechanical ventilation is reduced or eliminated in patients treated according to the above-described methods relative to untreated patients or relative to patients treated using a control method (e.g., standard of care (SOC)).

In some aspects, the clinical outcome is incidence of intensive care unit (ICU) stay. In some aspects, the incidence of ICU stay is reduced or eliminated in patients treated according to the above-described methods relative to untreated patients or relative to patients treated using a control method (e.g., SOC).

In some aspects, the clinical outcome is duration of ICU stay. In some aspects, duration of ICU stay is reduced in patients treated according to the above-described methods relative to untreated patients or relative to patients treated using a control method (e.g., SOC).

In some aspects, the clinical outcome is time to clinical failure defined as the time to death, mechanical ventilation, ICU admission, or withdrawal, whichever occurs first. In some aspects, time to clinical failure is increased in patients treated according to the above-described methods relative to untreated patients or relative to patients treated using a control method (e.g., SOC).

In some aspects, the clinical outcome is time to hospital discharge; or ready for discharge as evidenced by normal body temperature and respiratory rate, and stable oxygen saturation on ambient air or ≤2 L supplemental oxygen. In some aspects, time to hospital discharge or ready for discharge is increased in patients treated according to the above-described methods relative to untreated patients or relative to patients treated using a control method (e.g., SOC).

In some aspects, the clinical outcome is duration of supplemental oxygen. In some aspects, duration of supplemental oxygen is decreased in patients treated according to the above-described methods relative to untreated patients or relative to patients treated using a control method (e.g., SOC).

In some aspects, the clinical outcome is selected from the group consisting of incidence of vasopressor use, duration of vasopressor use, incidence of extracorporeal membrane oxygenation (ECMO), incidence of starting dialysis, SARS-CoV-2 viral load on Day 15 or day of hospital discharge (whichever occurs first), and proportion of individuals with secondary bacterial infections. In some aspects, one or more of incidence of vasopressor use, duration of vasopressor use, incidence of extracorporeal membrane oxygenation (ECMO), incidence of starting dialysis, SARS-CoV-2 viral load on Day 15 or day of hospital discharge (whichever occurs first), or proportion of individuals with secondary bacterial infections are decreased in patients treated according to the above-described methods relative to untreated patients or relative to patients treated using a control method (e.g., SOC).

In some aspects of the above-described methods of treatment and prophylaxis, the method is associated with an acceptable safety outcome compared with SOC. In some aspects, the safety outcome is selected from the group consisting of: incidence and severity of adverse events; incidence and severity of adverse events with severity determined according to National Cancer Institute Common Terminology Criteria for Adverse Events (NCI CTCAE) v5.0; change from baseline in targeted vital signs; and change from baseline in targeted clinical laboratory test results. In some aspects, the SOC comprises supportive care, administration of one or more anti-viral agents, and/or administration of one or more low-dose corticosteroids.

G. Methods of Delivery

The compositions utilized in the methods described herein (e.g., a modulator of an interaction between the SARS CoV-2 S protein RBD and CNTN1, IL12RB1, or IL1RAPL2, e.g., a small molecule, an antibody, an antigen-binding fragment, a peptide, a mimic, an antisense oligonucleotide, or an siRNA) can be administered by any suitable method, including, for example, intravenously, intramuscularly, subcutaneously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, orally, transdermally, intravitreally (e.g., by intravitreal injection), by eye drop, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In some aspects, a modulator of a protein-protein interaction is administered intravenously, intramuscularly, subcutaneously, topically, orally, transdermally, intraperitoneally, intraorbitally, by implantation, by inhalation, intrathecally, intraventricularly, or intranasally. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

A modulator of a protein-protein interaction described herein (and any additional therapeutic agent) may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The modulator need not be, but is optionally formulated with and/or administered concurrently with one or more agents currently used to prevent or treat the disorder in question. The effective amount of such other agents depends on the amount of the modulator present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

All patent, patent publication and literature references cited in the present specification are hereby incorporated by reference in their entirety.

V. Examples

Example 1. A High-Throughput Platform for Detection of Extracellular Interactions The tissue tropism of most human viruses is determined by receptors and other cofactors expressed on the host cell surface that mediate viral attachment and entry. Despite their relevance for therapeutic development, the extracellular protein interactions that mediate infection remain poorly characterized, in part due to their biochemical intractability, which renders them difficult to study using most common technologies (Martinez-Martin et al., *Cell,* 174: 1158-1171 e1119, 2018; Martinez-Martin, *J Immunol Res,* 2017: 2197615, 2017). In particular, membrane proteins often show poor expression and solubility, and receptor-ligand interactions on the plasma membrane, overall challenging detection by mass spectrometry, including recently developed proximity proteomics methods (Wright et al., *Biochem Soc Trans,* 38: 191-922, 2010; Husain et al., *Mol Cell Proteomics,* 18: 2310-2323, 2019; Verschueren et al., *Cell,* 182; 329-344 e319, 2020). The implementation of new technologies optimally suited for detection of protein interactions on the cell surface will be key to better understand viral infection and cellular entry, and ultimately enable identification of new targets for therapeutic development.

Figure 1A:
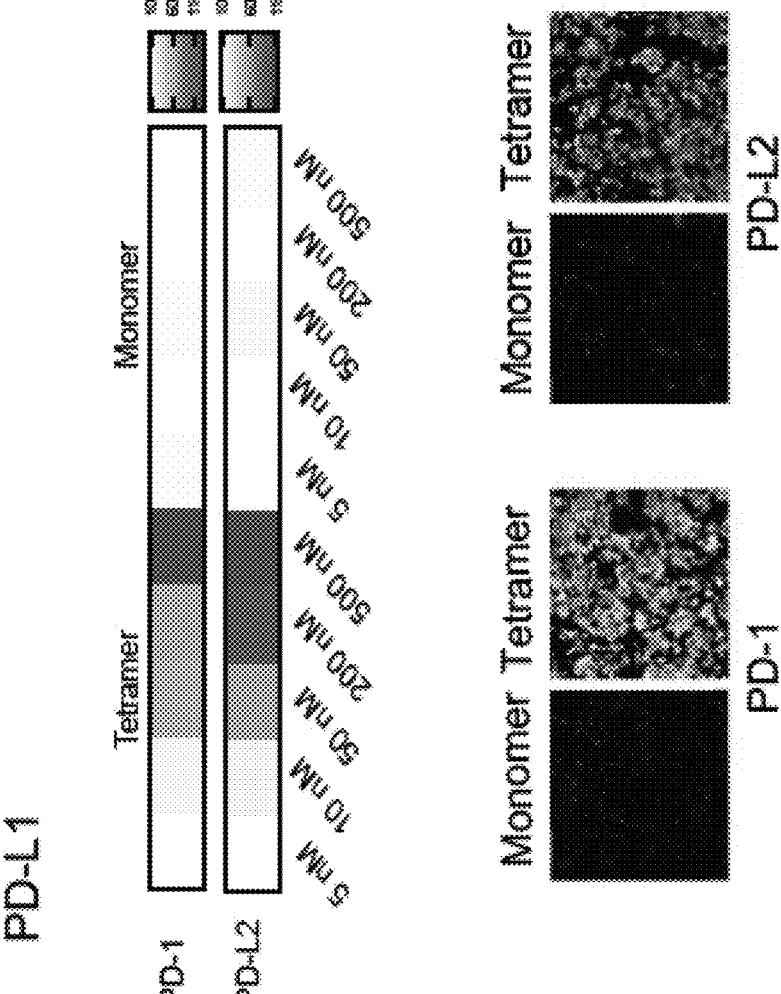
FIG. 1A is a set of representative photomicrographs showing the fluorescent signal of PD-L1 expressed as either a fluorescently labeled recombinant monomeric ectodomain (monomer) or a fluorescently labeled tetrameric ectodomain (tetramer) bound to the surface of cells transiently expressing PD-1 or PD-L2 and a pair of diagrams showing quantification of the normalized fluorescence intensity in the assays at the indicated concentrations of the tetramer or monomer (top).
Figure 1C:
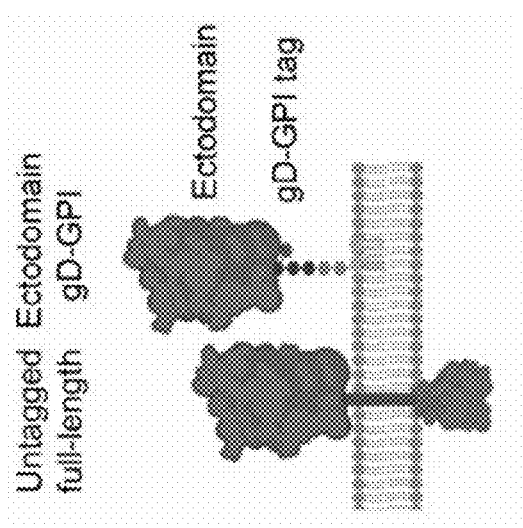
FIG. 1C is a schematic diagram showing an untagged, full-length transmembrane protein and a construct comprising the transmembrane protein ectodomain fused to a glycoprotein D (gD) tag and a glycosylphosphatidylinositol (GPI) linker (gD-GPI tag).
Figure 1B:
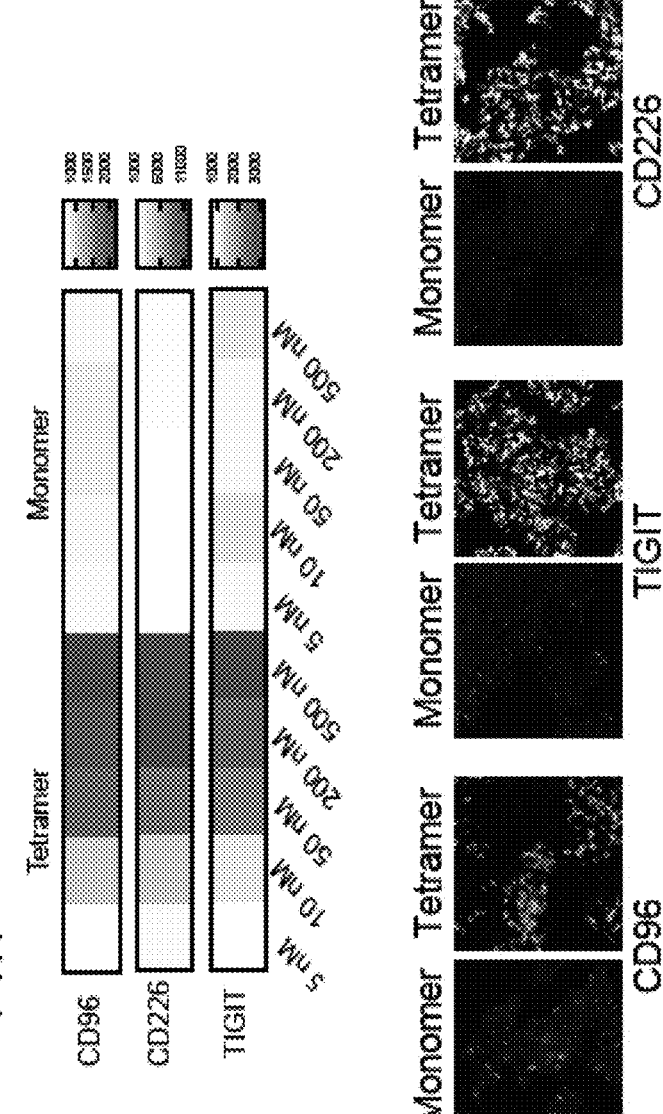
FIG. 1B is a set of representative photomicrographs showing the fluorescent signal of PVR expressed as either a fluorescently labeled recombinant monomeric ectodomain (monomer) or a fluorescently labeled tetrameric ectodomain (tetramer) bound to the surface of cells transiently expressing CD96, TIGIT, or CD226 and diagrams showing quantification of the normalized fluorescence intensity in the assays at the indicated concentrations of the tetramer or monomer (top).
Figure 1D:
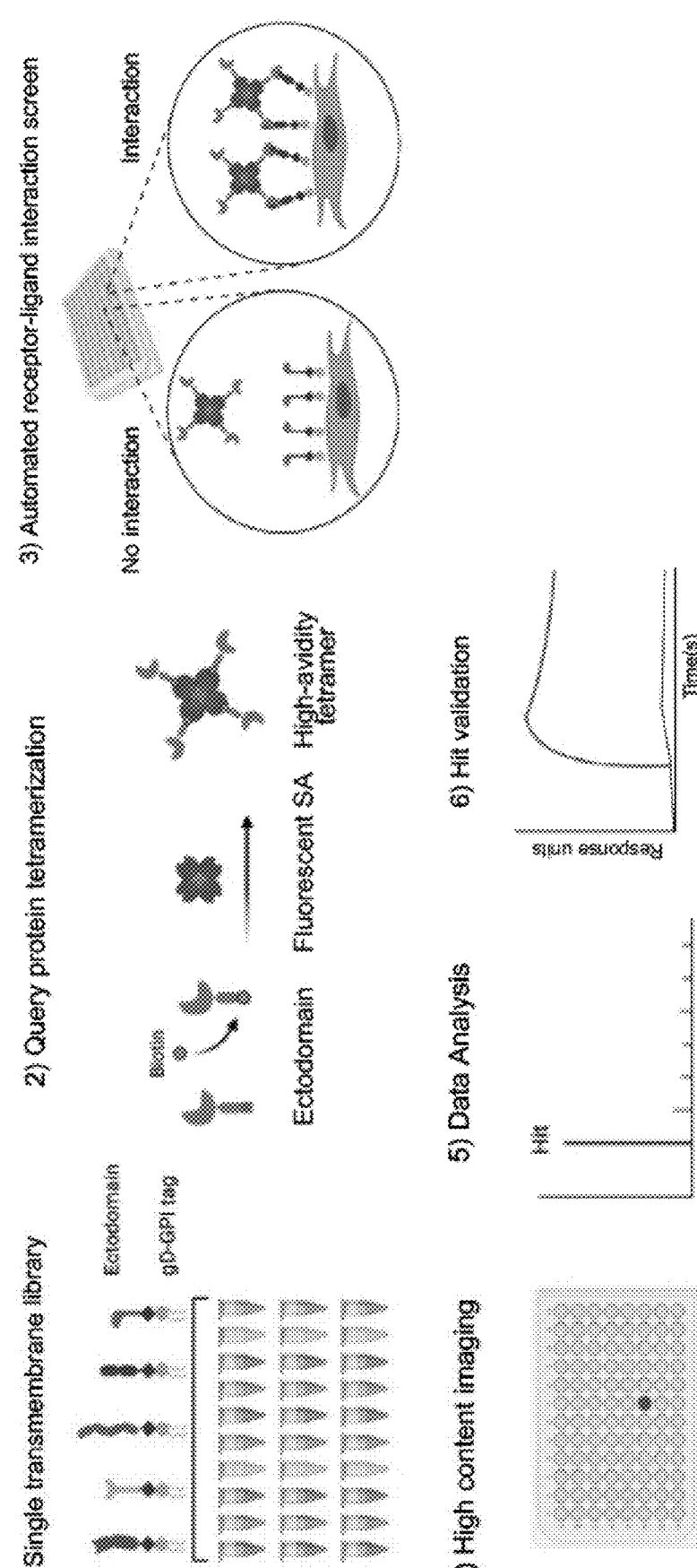
FIG. 1D is a schematic diagram showing the design of an automated cell-based platform for receptor-ligand discovery. (1) shows a library consisting of ≈1,200 unique STM receptors and selected isoforms (STM library), expressed as ectodomains fused to a gD-GPI tag. (2) shows a representative query protein, which is expressed as a recombinant ectodomain, is biotinylated, and is tetramerized using fluorescent streptavidin (SA) for increased binding avidity. (3) shows a plate comprising wells in which the gD-GPI-tagged ectodomains of the STM library are expressed on the surface of mammalian cells and are contacted with the tetramerized query protein. Binding of the query protein tetramer to the cell surface was detected by measuring the fluorescent signal. Images from individual wells are acquired using a high content microscope (4). Fluorescent signal intensity is calculated for each image, and represents query protein binding to each receptor expressed on the plasma membrane (5). Following data analysis and hit calling, new interactors are confirmed using orthogonal techniques such as surface plasmon resonance (6).

To overcome some of the limitations of the current methodologies, a comprehensive library of human proteins engineered for enhanced display on the plasma membrane was built and was coupled to a high-avidity tetramer-based approach for increased avidity and detection of receptor-ligand interactions in high throughput (FIG. 1D).

Using this high-throughput platform, the extracellular interactomes of SARS CoV spike proteins were characterized. Host factors specifically targeted by SARS CoV-2 and not SARS CoV-1 were identified, including receptors prominently expressed in the nervous system and the olfactory epithelium.

A. Query Protein Tetramerization

First, query protein tetramerization was used to test interactions between the immune receptor PD-L1/CD274, the poliovirus receptor (PVR), and their respective ligands. Protein tetramerization increases the likelihood of detection of weak or transient receptor interactions. Briefly, PD-L1 or PVR, the query proteins, were expressed as recombinant biotinylated ectodomains, and then tetramerized using fluorescent streptavidin to enable quantification of receptor-ligand interactions. Tetrameric PD-L1 or PVR and monomeric PD-L1 or PVR controls were tested for binding to cells transiently expressing the relevant binding partners. Tetramerization of the query protein significantly enhanced detection of receptor-ligand interactions over the monomeric ectodomain, including micromolar-affinity interactions such as PD1-PD-L1 (FIGS. 1A and 1B).

B. STM Library

Figure 5:
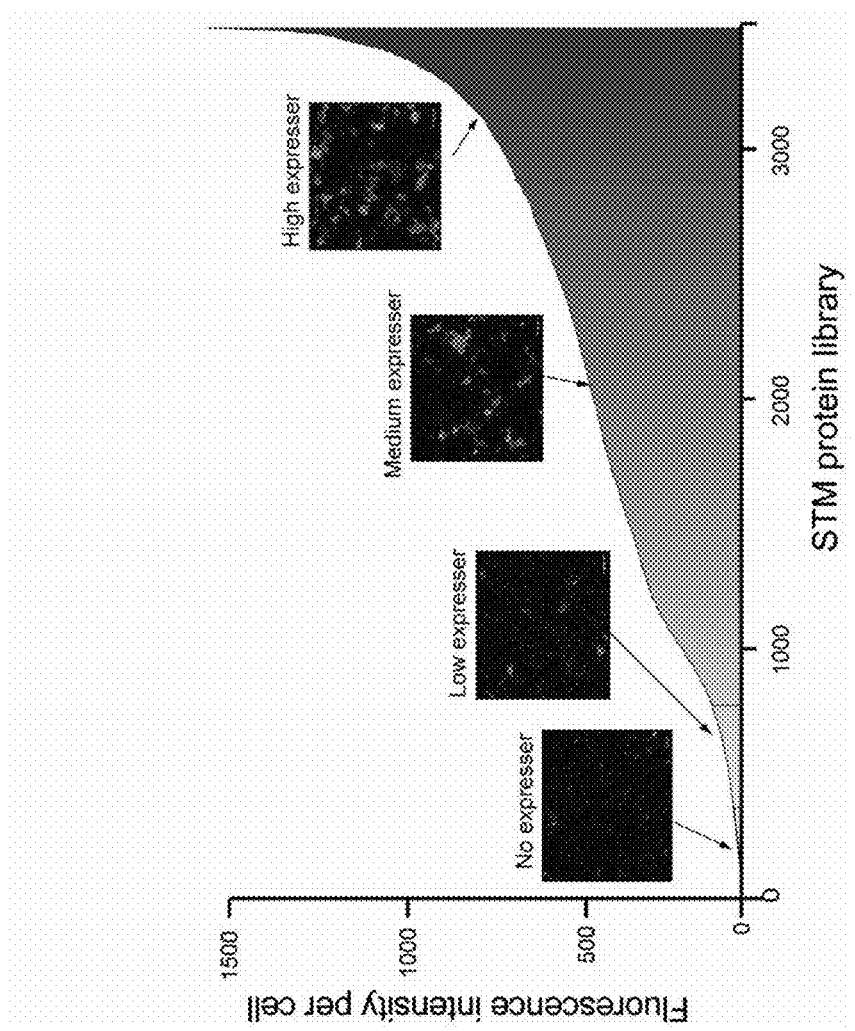
FIG. 5 is a graph showing quantification of surface expression (fluorescence intensity per cell) for members of the ectodomain-gD-GPI library measured using an anti-gD antibody for detection. Representative images of surface staining for not detectable (no expresser), low, medium, and high expressers are shown. Dotted lines indicate arbitrary cut-offs for the different expression levels. Expression is representative of two independent assays.

Next, to enable controlled display and detection of proteins expressed on the cell surface, a large library was built encompassing most single-pass transmembrane (STM) proteins in the human genome, engineered as ectodomains fused to a glycoprotein D (gD) tag and a glycosylphosphatidyl-inositol (GPI)-linker (referred to as "ectodomain-gD-GPI") (FIG. 1C). This receptor tagging strategy enables protein targeting to the plasma membrane (via the GPI linker) and quantification of protein expression on the cell surface (measured by gD tag staining). The protein library was tested for expression on transiently transfected cells using a semi-automated transfection procedure. Notably, medium to high cell surface expression levels were achieved for over 75% of the over 3,500 STM proteins analyzed, whereas only about 10% of the proteins did not show detectable expression on the plasma membrane, indicating that most of the receptors in the library are displayed on the cell surface and available for interaction with the relevant binding partners (FIG. 5).

Generation of the Ectodomain gD-GPI-Tagged Receptor Library and Plasmids Used for Confirmation of RBD Receptors The list of STM-containing receptors was compiled upon bioinformatics analysis using various algorithms for prediction of protein features such as protein domains and subcellular localizations, followed by manual curation and review of published annotations. The boundaries of the ectodomains were annotated after in silico prediction of the signal peptides and transmembrane regions or GPI-linkage sites. The ectodomain of each receptor, containing its native signal sequence, was synthesized and cloned into a pRK5 vector (Genentech) in frame with a gD-GPI tag. The final library contains 1,195 unique STM receptors, alongside selected receptor isoforms, expressed as ectodomain-gD-GPI fusions. ~700 receptor isoforms were included in the library. For generation of the full-length clones for cell expression and binding studies, the relevant STM proteins were cloned into a pRK vector (Genentech) as full-length, untagged, proteins. Full-length and ectodomain-gDGPI plasmids were transiently expressed on HEK/293T cells, as described.

C. High-Throughput Screen

Figure 1E:
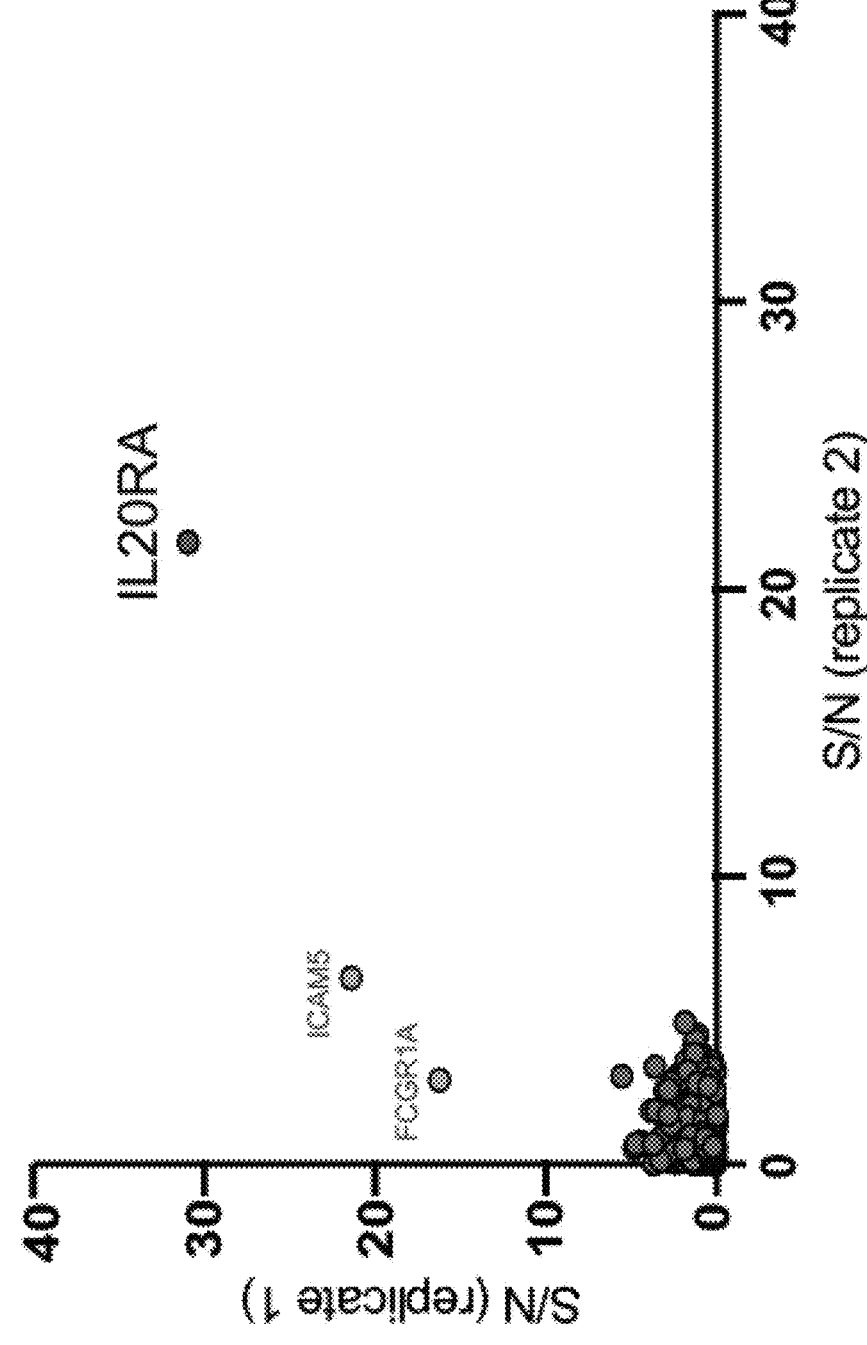
FIG. 1E is an intersection plot showing two replicates of an assay for binding of the receptor B7-H3, expressed as a tetramerized ectodomain, to each of the proteins of the STM library. Each circle represents query protein binding to a unique receptor in the library. Unique high-scoring hits are shown in red. Hits shown in grey are empirically determined nonspecific binders.
Figure 1F:
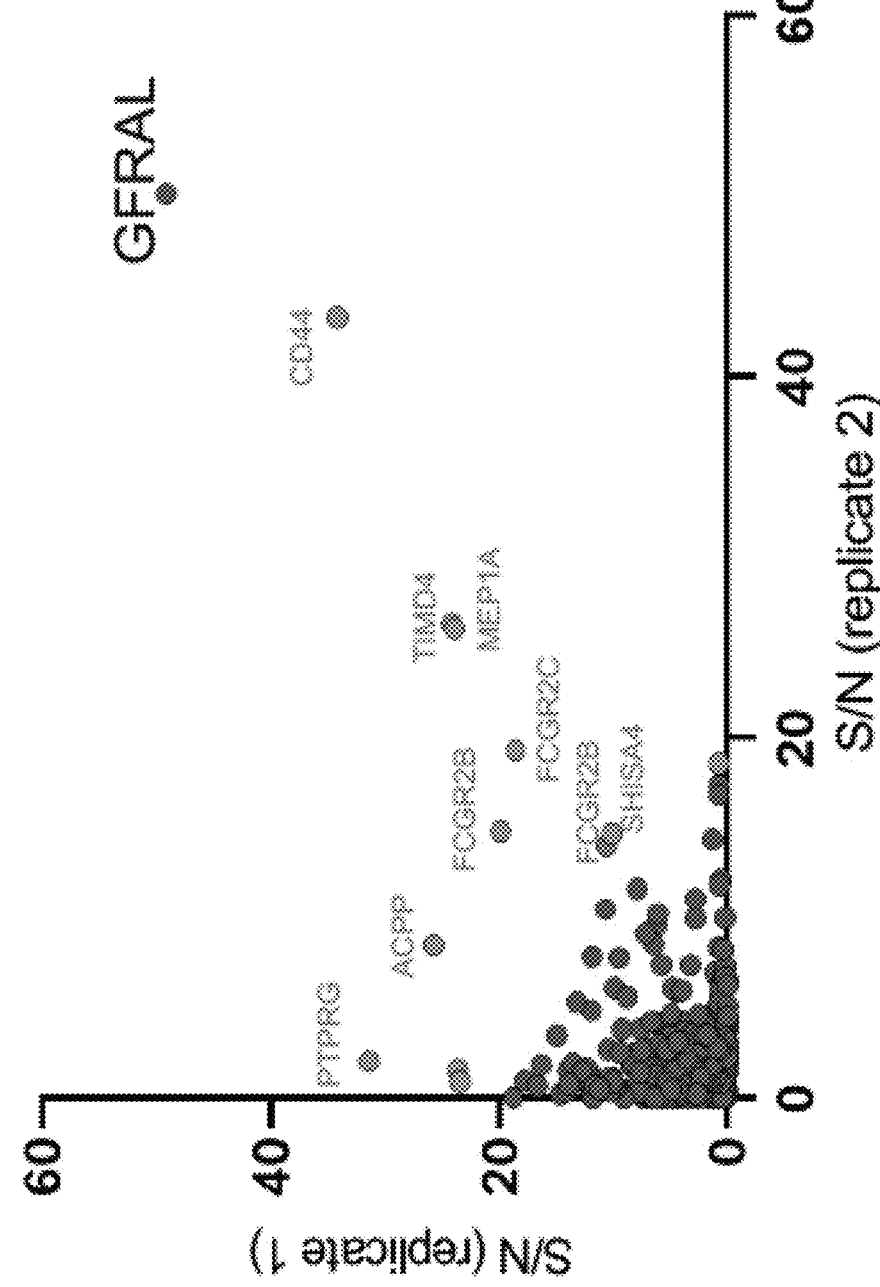
FIG. 1F is an intersection plot showing two replicates of an assay for binding of the secreted factor GDF15, expressed as a tetramerized ectodomain, to each of the proteins of the STM library. Each circle represents query protein binding to a unique receptor in the library. Unique high-scoring hits are shown in red. Hits shown in grey are empirically determined nonspecific binders.

Next, the newly developed ectodomain-gD-GPI STM protein collection was used in combination with the tetramer-based screening method to enhance discovery of receptor-ligand interactions in high throughput. To do so, a method for automated cell transfection and screening was implemented, followed by high content imaging for detection of tetrameric query protein binding to the cell surface (FIG. 1D). This high throughput platform was first used to identify cell surface interactors of the immune receptor B7-H3/CD276 in an unbiased fashion (FIG. 1E). The interleukin-20 receptor subunit alpha (IL20-RA) was detected as the only specific high-scoring hit, in agreement with recent findings (Husain et al., *Mol Cell Proteomics,* 18: 2310-2323, 2019). Next, screening was performed using GDF15, a secreted factor that belongs of the transforming growth factor beta superfamily. The receptor GFRAL was identified as the only specific and high-scoring hit (FIG. 1F), as previously observed (Mullican et al., *Nat Med,* 23: 1150-1157, 2017). Thus, the newly established platform enabled systematic identification of binding partners for unrelated query proteins with high sensitivity.

Automated Single-Clone, Cell-Based, Receptor Discovery Platform

The library of STM human receptors was expressed on HEK/293T cells. Cells were transiently transfected with individual receptor clones following a reverse transfection protocol using semi-automated procedure. Briefly, 25 μL of LIPOFECTAMINE™ LTX-PLUS™ mixture in Opti-MEM™ medium (Thermo) was dispensed to 384 well microtiter plates containing 6 ng of DNA per well. The DNA-LIPOFECTAMINE™ complexes were incubated for 30 min at 37° C., and subsequently the cells (resuspended in DMEM media at 0.125 million cells/ml) were aliquoted in the assay plates using an automatic cell dispenser. Screening for RBD binding partners was performed 48 hours after transfection. A number of GFP-tagged clones were included to control for cell transfection efficiency.

Analysis of RBD tetramer binding to the cell surface was performed using an integrated robotic system consisting of automated liquid handling devices. Growth media was removed from cell cultures and cells were incubated with the RBD tetramer for 45 minutes at 4° C. Cell surface binding was assayed in PBS containing 0.1% BSA supplemented with calcium and magnesium. Following incubation with RBD, the cells were washed and fixed with 4% PFA and stored at 4° C. protected from light. Images were acquired from individual wells using a high content microscope (In Cell 6000, GE Healthcare). Image data were exported as tiff files and processed using the Developer Toolbox version v1.6 software. Cell surface tetramer staining was represented as fluorescent signal intensities. Images were analyzed using a custom analysis module, and segmentations were performed based on positive cell surface staining. Minimal post-processing analysis and exclusion parameters were set up to obtain optimal outline of desired objects and minimize any background signals due to screening artifacts. RBD binding to the cell surface was represented as signal/noise ratio.

The RBD protein was assayed as an APC-conjugated tetramer to enhance detection of binding partners due to enhanced avidity. RBD was randomly biotinylated, as described, and subsequently tetramerized following the protocol provided by the NIH Tetramer Core Facility, using fluorescent streptavidin purchased from PROZYME®. Streptavidin was added at room temperature with the samples protected from light, and tetramers were subsequently stored on ice until the assay was performed.

Example 2. Characterization of the Extracellular Interactome of the SARS-CoV-Spike Protein The method was next used to study the spike (S) protein of SARS-CoV-2, the causative agent of COVID-19. Like the highly related SARS-CoV-1, SARS-CoV-2 has been shown to utilize the angiotensin-converting enzyme 2 (ACE2) as a main receptor for host cell attachment and entry, through an interaction mediated by the receptor binding domain (RBD) of the spike protein (Hoffmann et al., *Cell*, 181: 271-280 e278, 2020; Lan et al., *Nature*, 581: 215-220, 2020). Subsequent membrane fusion is facilitated by S protein priming by host cell proteases, including TMPRSS2 and serine protease cathepsins. While intensive research has focused on the role of ACE2 in SARS-CoV-2 infection, the expression profile of ACE2 does not explain the multi-organ tropism observed for this virus, which includes kidneys, liver and the heart, among other organs (Puelles et al., *N Engl J Med*, 383: 590-592, 2020; Iadecola et al., *Cell*, 183: 16-27 el 1, 2020; Braun et al., *Lancet*, 396: 597-598, 2020). Moreover, numerous studies have now demonstrated the neuro-invasive potential of SARS-CoV-2, and increasing evidence from in vitro studies, organoid cultures and postmortem analyses have now shown that diverse populations of neural cells are susceptible to infection by SARS CoV-2. Over half of patients show neurological symptoms, from migraine, olfactory and gustatory dysfunctions to impaired consciousness, which in many cases persist in the individuals that recover from the infection (Alomari et al., *Clin Neurol Neurosurg*, 198: 106116, 2020; Matschke et al., *Lancet Neurol*, 19: 919-929, 2020; De Felice et al., *Trends Neurosci*, 43: 355-357, 2020). Such extended tropism and increased transmissibility suggest the existence of additional, and currently unknown, host factors that may facilitate interactions with host cells and that may importantly influence the outcome of infection and the clinical severity of SARS-CoV-2.

Thus, to enable an unbiased characterization of the cellular factors targeted by the SARS-CoV-2 spike protein that might participate in viral attachment and entry, the SARS-CoV-2 spike protein RBD was screened using the new platform described in Example 1 (FIG. 1D). These efforts identified ACE2 as a prominent hit (FIG. 2A), alongside Neuropilin-2, recently described as a factor that facilitates viral infection (Cantuti-Castelvetri et al., *Science*, 370: 856-860, 2020; Daly et al., *Science*, 370: 861-865, 2020).

Figure 2A:
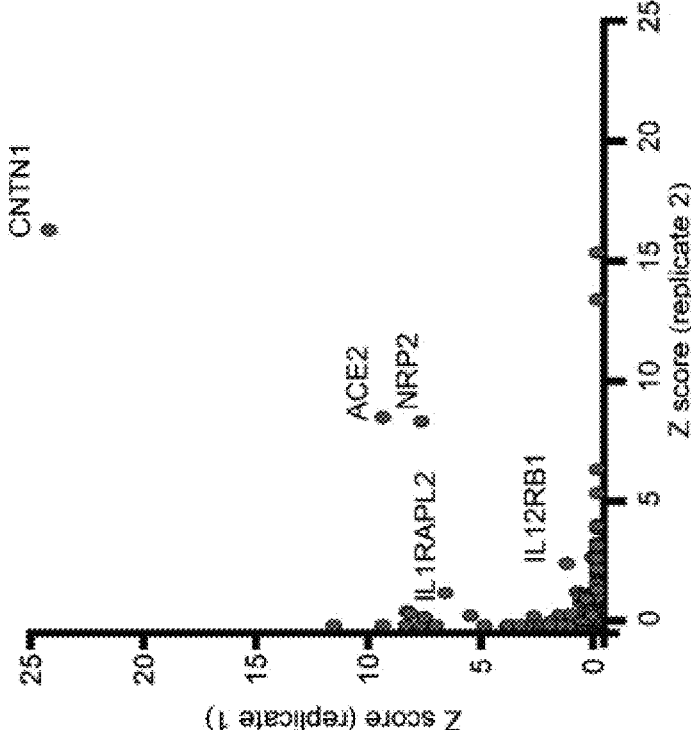
FIG. 2A is an intersection plot showing two replicates of an assay for binding of the severe acute respiratory syndrome coronavirus 2 (SARS-CoV-2) spike protein receptor binding domain (RBD), expressed as a tetramerized ectodomain, to each of the proteins of the STM library. Each circle represents query protein binding to a unique receptor in the library. Unique high-scoring hits are shown in red. ACE2, IL12RB1, IL1RAPL2, contactin-1 (CNTN1), and neuropilin-2 (NRP2) were identified as high-scoring hits.

Notably, three additional proteins were identified and validated as high-scoring hits for the SARS-CoV-2 spike protein RBD, including the interleukin receptor IL12RB1 and the neural cell-associated proteins Contactin-1 (CNTN1) and IL1RAPL2 (FIG. 2A). Analysis of publicly available transcriptomics datasets for indicates that the cell surface proteins targeted by the spike are expressed in a variety of tissues, including prominent expression in the nervous system. CNTN1 is a cell surface protein involved in axon guidance.

Figure 2B:
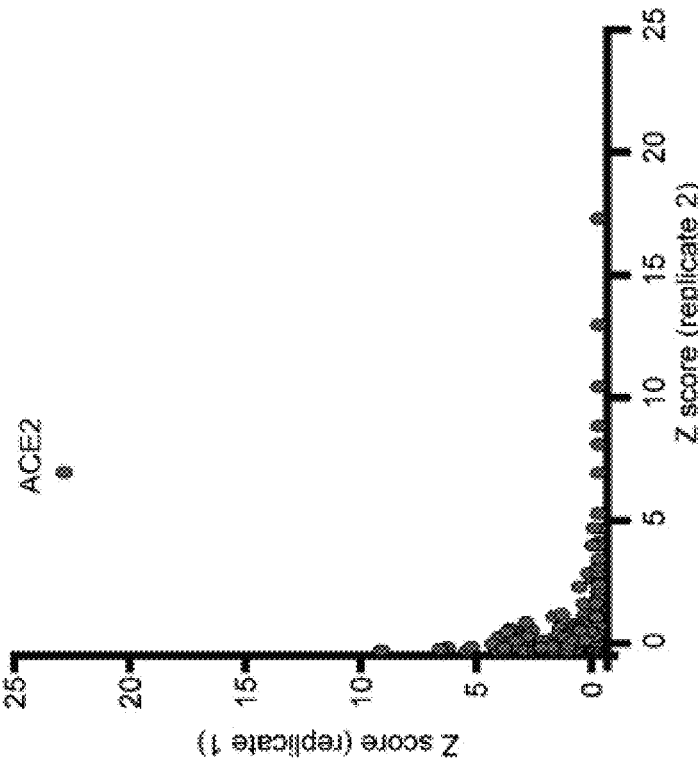
FIG. 2B is an intersection plot showing two replicates of an assay for binding of the SARS-CoV-1 RBD, expressed as a tetramerized ectodomain, to each of the proteins of the STM library. Each circle represents query protein binding to a unique receptor in the library. Unique high-scoring hits are shown in red. ACE2 was identified as a high-scoring hit.
Figure 6A:
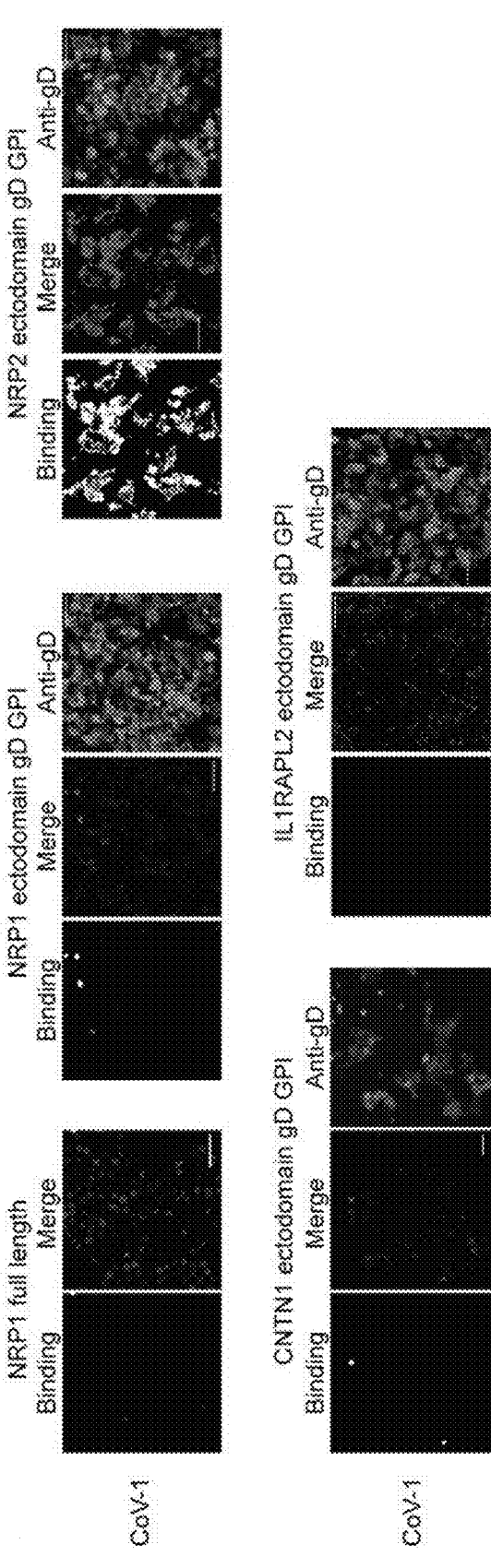
FIG. 6A is a set of representative immunofluorescence photomicrographs showing SARS CoV-1 RBD binding to cells expressing NRP1, NRP2, or IL1RAPL2 expressed as g D-GPI-tagged ectodomains. RBD proteins were biotinylated and tetramerized, and binding to the cell surface was measured by immunofluorescence (binding; shown in red). An anti-gD antibody was utilized to analyze expression of the RBD binding partners on the plasma membrane (anti-gD; shown in green). Nuclei are represented in blue. Images show RBD tetramer binding at 50 nM concentration. Scale bar=50 μm.
Figure 6B:
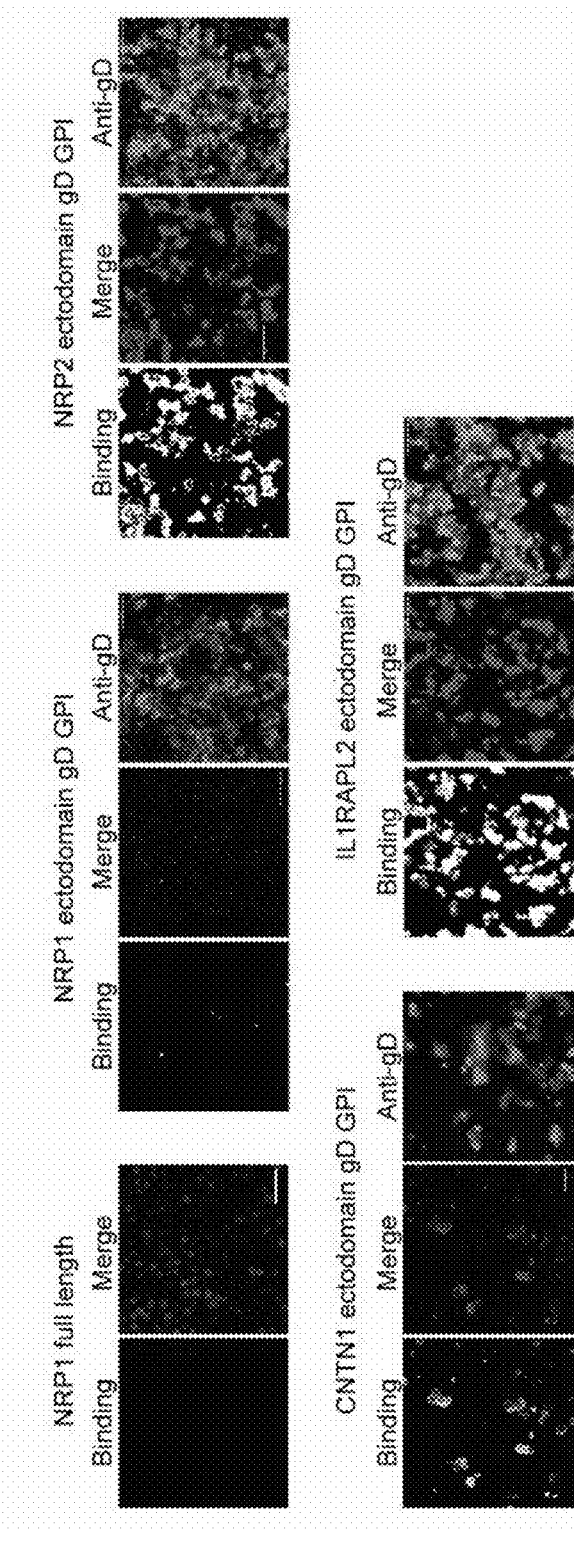
FIG. 6B is a set of representative immunofluorescence photomicrographs showing SARS CoV-2 RBD binding to cells expressing NRP1, NRP2, or IL1RAPL2 expressed as g D-GPI-tagged ectodomains. RBD proteins were biotinylated and tetramerized, and binding to the cell surface was measured by immunofluorescence (binding; shown in red). An anti-gD antibody was utilized to analyze expression of the RBD binding partners on the plasma membrane (anti-gD.

Next, to assess cellular receptor specificity for SARS CoV-2 and the highly related SARS CoV-1, similar screens were performed for the SARS-CoV-1 spike protein RBD. An exemplary SARS-CoV-2 spike protein has the sequence of SEQ ID NO: 5. These screens identified ACE2 as the only top-scoring hit (FIG. 2B). No binding to CNTN1, IL12RB1 or IL1RAPL2, identified as putative binding partners for SARS CoV-1 spike protein RBD, was detected in these screens (FIGS. 6A and 6B). Interestingly, although weak binding to NRP2 was observed for the SARS CoV-1 spike protein RBD upon close inspection of the images, this putative interactor was not detected as high-scoring hit due to the weak SARS CoV-1 spike protein RBD binding to the NRP2-expressing cells.

Receptor Binding Domain (RBD) and Spike Trimer Production and Biotinylation

Optimized coding DNAs for SARS-CoV-1 RBD (SEQ ID NO: 6; R319-5591) and SARS-CoV-2 RBD (SEQ ID NO: 4; R319-F541) and spike (SEQ ID NO: 2; M1-01208) were cloned into a pRK vector behind a CMV promoter and, in the case of the RBDs, an N-terminal secretion signal. RBD constructs were generated containing a C-terminal Avi-His8 and spike was generated containing a C-terminal trimeric coiled-coil sequence and Avi-His8 tag. DNA constructs were transfected with polyethylenimine using standard protocols into Expi293™ cells when the cell density reached 4×10⁶ cells per ml, and suspension cultures were grown in SMM 293T-I medium under 5% $CO_2$ at 37° C. Culture supernatants were harvested after 6 days, filtered, and subsequently passed over 2 mL of Ni-Excel resin. Resin was washed with ten column volumes of 50 mM Tris pH 8, 100 mM NaCl, 20 mM imidazole, and eluted with the same buffer containing 250 mM imidazole. Samples were concentrated and passed over a Superdex 200 16/60 column in 50 mM Tris pH 8, 100 mM NaCl, and peak fractions were pooled and biotinylated using BirA and standard protocols. Following biotinylation of the Avi-tag, proteins were subsequently passed over the Superdex 200 16/60 column and peak fractions were pooled and frozen at −80° C. until further use.

For the STM interactome discovery screens, the RBD proteins were randomly biotinylated using EZ-LINK™ Sulfo-NHS-Biotin (Cat. No. 21217, Thermo Fisher) following the manufacturer's protocol with some modifications to minimize biotin incorporation. Following biotinylation, the proteins were tetramerized using APC-conjugated streptavidin (PROZYME®) following the protocol described by the NIH tetramer core facility.

Recombinant Proteins and Antibodies RBD and spike protein were generated as described above. The following proteins were purchased from R&D Systems: IL12RB1-Fc; IL1RAPL2-Fc; CNTN1-Fc; ACE2-Fc; Neuropilin2-Fc and Neuropilin1-His. His-tagged CNTN1 and ACE2-Fc were purchased from Sino Biologicals.

Example 3. Validation of SARS-CoV-Spike Protein Interactions

Figure 2C:
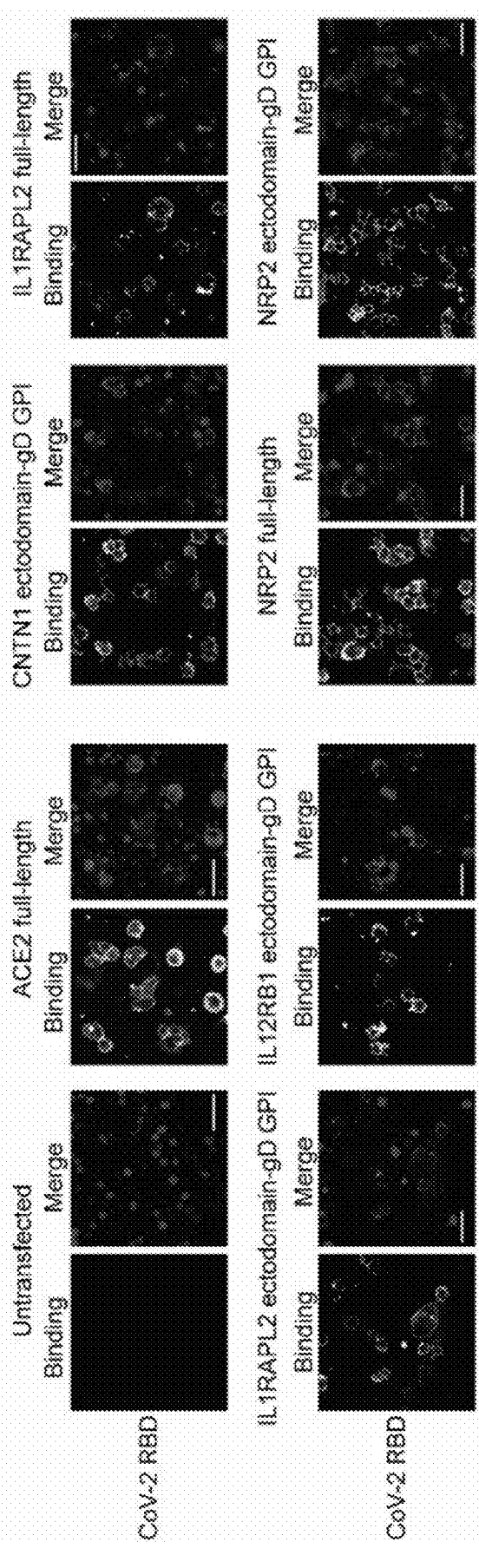
FIG. 2C is a set of representative immunofluorescence photomicrographs showing the SARS-CoV-2 spike protein RBD (Cov-2 RBD), expressed as a fluorescently labeled tetrameric ectodomain, bound to the surface of cells expressing full-length ACE2, full-length IL12RB1, IL12RB1 expressed as an ectodomain fused to gD-GPI, CNTN1 expressed as an ectodomain fused to gD-GPI, full-length IL1RAPL2, full-length NRP2, and NRP2 expressed as an ectodomain fused to gD-GPI. Untransfected cells are shown as a control. Cells were contacted with the RBD tetramer at a 50 nM concentration. Red: RBD tetramer. Blue: nuclei. Scale bar=50 μM.

The findings of Example 2 were then confirmed using orthogonal methods. First, the putative binding partners were transiently expressed on HEK/293T cells as either ectodomain gD-GPI constructs or full-length, native receptors, and binding of SARS CoV-2 spike protein RBD as a recombinant, tetramerized protein was analyzed by immunofluorescence. Clear binding to the plasma membrane of cells transiently over-expressing ACE2 was observed, as expected (FIG. 2C). Importantly, these assays also confirmed the interactions of the SARS CoV-2 spike protein RBD with NRP2, IL12RB1, and CNTN1 when these full-length receptors were expressed on the plasma membrane (FIG. 2C). HEK/293T cells were grown in DMEM high glucose medium supplemented with 10% FBS, glutamine and antibiotics, and cultured at 37° C. and 5% $CO_2$. For transient expression of the screening hits, the cells were transfected in poly-D-lysine-coated 96- or 384-well plates, using Lipofectamine LTX-Plus (Thermo).

Figure 2D:
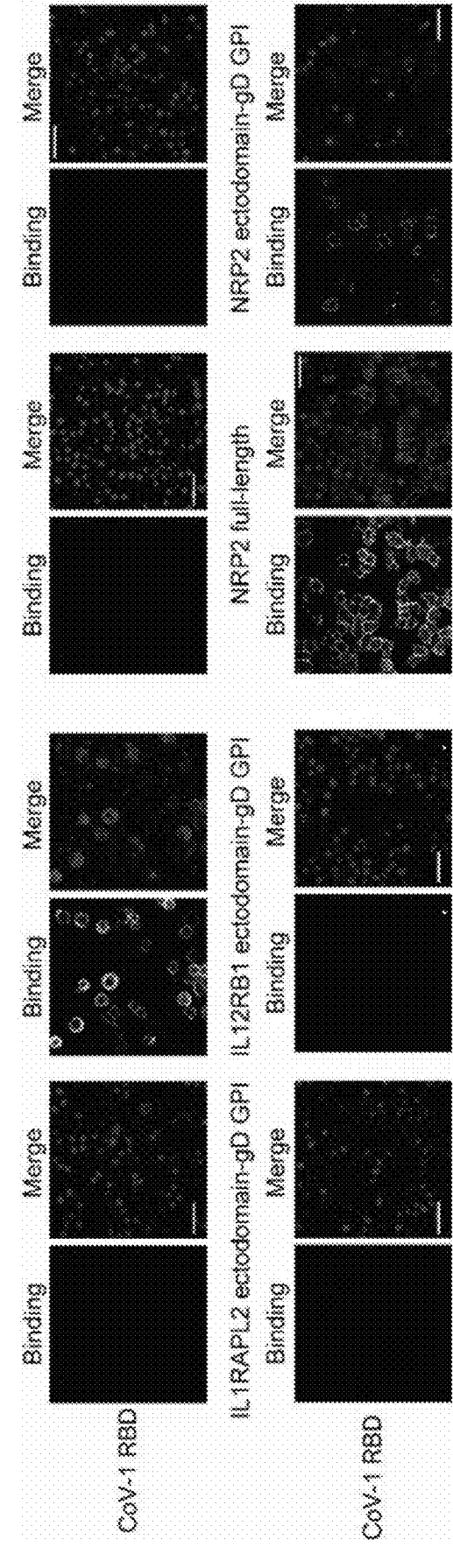
FIG. 2D is a set of representative immunofluorescence photomicrographs showing the SARS-CoV-1 spike protein RBD (Cov-1 RBD), expressed as a fluorescently labeled tetrameric ectodomain, bound to the surface of cells expressing full-length ACE2, full-length IL12RB1, IL12RB1 expressed as an ectodomain fused to gD-GPI, CNTN1 expressed as an ectodomain fused to gD-GPI, full-length IL1RAPL2, full-length NRP2, and NRP2 expressed as an ectodomain fused to gD-GPI. Untransfected cells are shown as a control. Cells were contacted with the RBD tetramer at a 50 nM concentration. Red: RBD tetramer. Blue: nuclei. Scale bar=50 μM.

Similar assays were performed to analyze binding between the SARS CoV-1 spike protein RBD and the receptors identified for the SARS CoV-2 spike protein RBD to further evaluate the specificity of the interactions. Notably, while these assays confirmed a relatively weak interaction with NRP2, no detectable binding was observed to the additional receptors CNTN1, IL12RB1 and IL1RAPL2 expressed on the cell surface (FIG. 2D), despite all receptors being expressed at sufficient levels on the cell surface (FIGS. 6A and 6B). Interestingly, detectable binding was not observed between either SARS CoV-1 or SARS CoV-2 RBD proteins and NRP1, expressed on the cell surface either as full-length receptor or a gD-GPI ectodomain (FIGS. 6A and 6B).

Figure 2E:
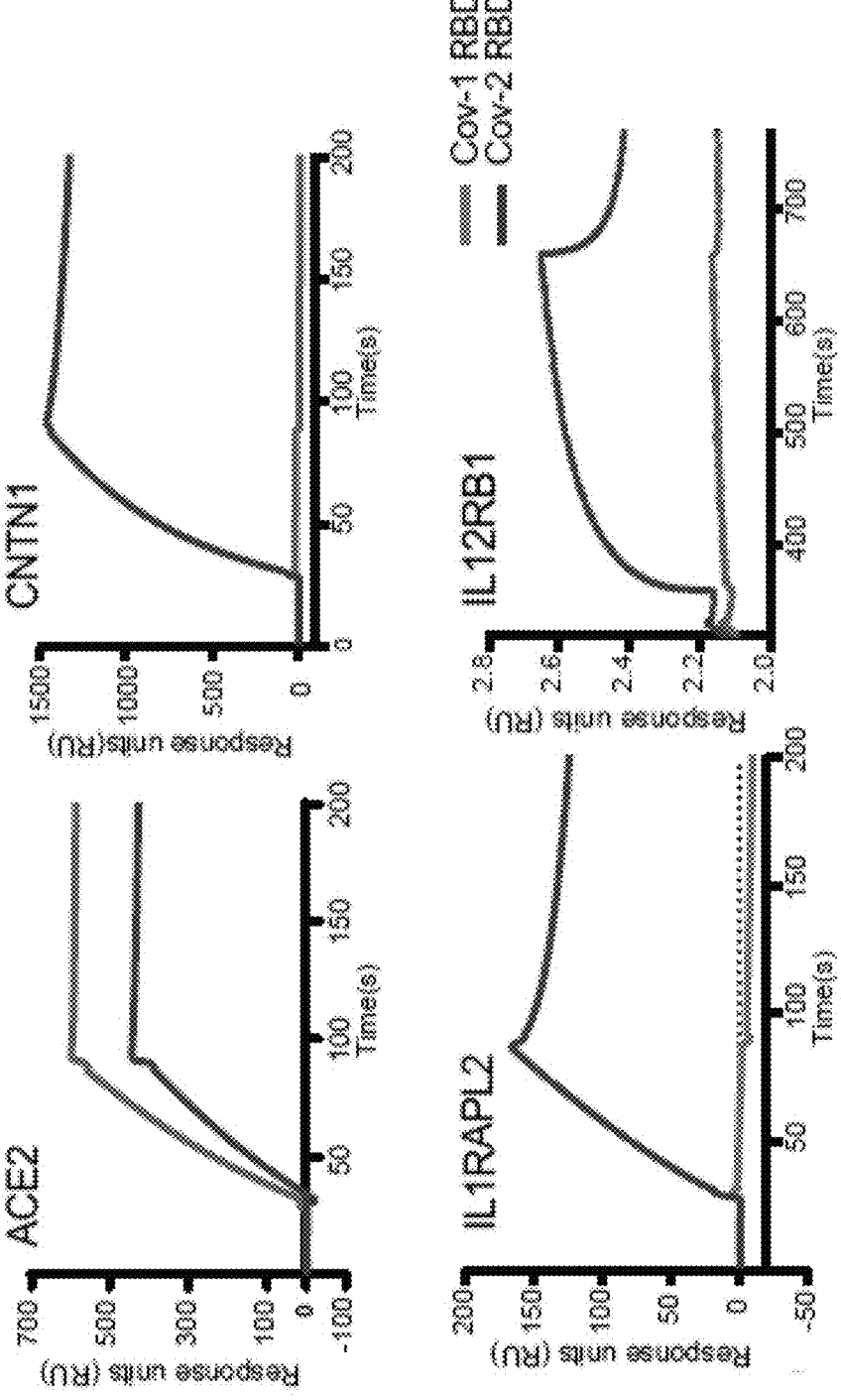
FIG. 2E is a set of surface plasmon resonance (SPR) plots showing binding of Cov-1 RBD (grey) or Cov-2 RBD (red) to ACE2, CNTN1, IL1RAPL2, or IL12RB1. RBD proteins were immobilized on sensor chips, and the indicated binding partners were provided at 500 nM concentration as recombinant Fc-tagged proteins used as soluble analytes. To test binding to IL12RB1, the biotinylated RBD proteins were captured onto streptavidin sensors and analyzed for binding to soluble IL21RB1-Fc using biolayer interferometry.

As an additional approach to validate and characterize these interactions, surface plasmon resonance (SPR) analysis was utilized to study binding between the SARS CoV-2 and SARS CoV-1 RBDs and the cellular receptors, assayed as purified proteins. These assays further confirmed the identified interactions, and corroborated the specificity of CNTN1, IL12RB1 and IL1RAPL2, as they showed no measurable binding to SARS CoV-1 spike protein RBD (FIG. 2E).

Figure 2F:
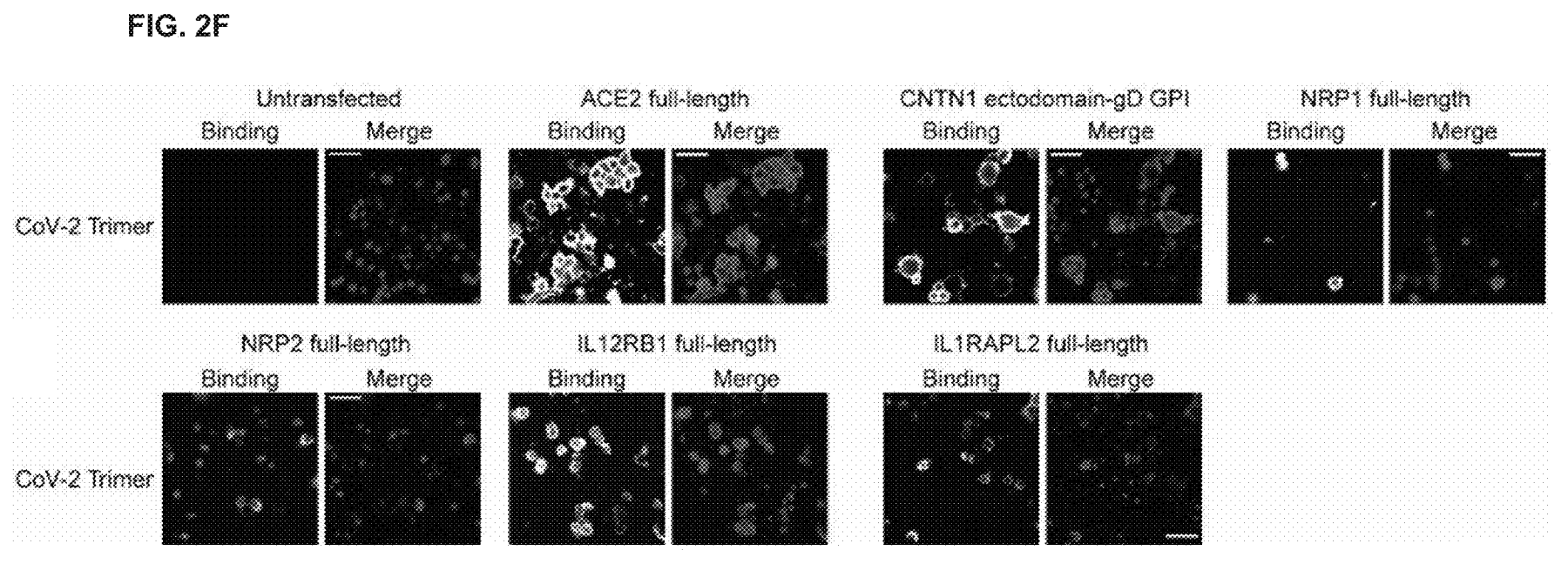

Next, the interactions between the host binding partners identified for the SARS CoV-2 spike protein RBD and the full ectodomain of the SARS CoV-2 spike trimer were studied. The spike trimer bound to ACE2, CNTN1, NRP2, IL12RB1 and IL12RAPL2 expressed on the cell surface (FIG. 2F). Interestingly, weak binding between the spike trimer and NRP1 expressed on cells was detected, in agreement with recent observations (Daly et al., *Science,* 370: 861-865, 2020).

A polybasic cleavage site in SARS-CoV-2 spike protein (not present in the SARS CoV-1 spike protein) has been shown to prime fusion, resulting in increased infection in vitro (Hoffmann et al., *Mol Cell,* 78: 779-784 e776. 2020). Proteolytic cleavage by furin and other host proteases results in a solvent-exposed loop that might create additional receptor binding sites (Walls et al., *Cell,* 181: 281-292 e286, 2020). In keeping with this, the results provided herein identify human IL12RB1, ILRAPL2 and CNTN1 as cellular factors that specifically bind to the SARS CoV-2 spike protein, suggesting that these proteins do not interact with the SARS CoV-1 spike, or do so with significantly lower binding affinities that are not detectable in the experimental conditions analyzed. By contrast, and of note, the data indicate that the recently described interaction with the Neuropilin coreceptors is common to both SARS CoV-1 and CoV-2 spike proteins, suggesting that, notwithstanding the relevance of Neuropilin during SARS CoV-2 infection, additional factors may be involved in the differential pathogenesis and extended tissue tropism of this virus. Interestingly, the findings herein show the RBD of both SARS CoV-1 and CoV-2 is sufficient to establish a measurable interaction with NRP2 and not NRP1 in the experimental conditions tested (FIGS. 2A-2F, 8A, and 8B), suggesting a differential binding mode between the spike and these co-receptors. Spike binding to NRP1 is largely mediated by the CendR peptide ($^{682}$RRAR$^{685}$) in the S1 protein generated upon furin cleavage. This region is absent in the RBD proteins utilized in the present study, spanning amino-acids R319 to 5591, thus explaining the lack of binding to NRP1, which is indeed recapitulated when the full trimer ectodomain was analyzed (FIG. 2F). Nonetheless, the observed differences in binding to NRP1 and NRP2 in this work suggest that different determinants within RBD are involved in these interactions.

Surface Plasmon Resonance and Biolayer Interferometry

RBD interactions with the relevant host proteins were analyzed by SPR using a BIACORE™ 8K (GE Healthcare) or Proteon instrument (Biorad). Indicated proteins were immobilized on CM5 or GLC sensors chips, respectively, using standard amino coupling method. Analytes were run at the concentrations indicated in each case, in HBS-P buffer (0.01 M HEPES, 0.15 M NaCl and 0.005% surfactant P20, pH7.4) or in PBS-0.01 tween 20 when the Proteon instrument was used. For kinetic calculations, ligands were immobilized at low resonance units, and $K_D$ values were calculated in equilibrium. All sensograms were analyzed with BiaEvaluation 4.1 (BIACORE™) or Proteon Manager 3.1.0.6 (Proteon) software.

Validation of RBD Cell Receptors by Immunofluorescence

The host receptors identified as binding partners for the spike protein were transiently expressed in HEK/293T cells, and assayed at 48 hours or 72 hours post-transfection. Randomly biotinylated RBD or site specific-biotinylated spike trimer were tetramerized using fluorescent streptavidin (PROZYME®) for increased avidity. Typically, the proteins were incubated with the cells for 1 hour at 4° C., washed, and subsequently fixed with 4% PFA. For detection of ectodomain-g DGPI expression on the cell surface, cells were fixed with 4% PFA, blocked with PBS containing 5% BSA, and subsequently stained using an anti-gD antibody (Abcam). Samples were washed and incubated with fluorescently-labeled Alexa Fluor antibodies (Thermo Scientific). Incubations with the primary and secondary antibodies were performed in PBS-1% BSA at 4° C. O/N, or 1 hour at 37° C., respectively. Images were acquired using a Leica SP5 confocal or an InCell 6000 high content imager and analyzed using Fiji software.

Example 4. Cell and Tissue Expression of
SARS-CoV-2 Spike Protein RBD Binders

Infection Assays with SARS CoV-2 Spike Pseudotyped
Particles

Mounting evidence suggest that the neurological complications associated with the infection may be associated to infection of the choroid plexus, a key barrier that prevents cell influx and thus excessive inflammation in the cerebrospinal fluid and brain. In support of the notion that SARS CoV-2 can productively infect neural cells, a recently published single nucleus transcriptome of deceased COVID-19 patients show a significant impact on the transcriptional profile of all major cortex parenchymal and choroid plexus cell types, findings that correlated with infection of the barrier-forming cortical vasculature, meninges and choroid plexus (Yang et al., bioRxiv, doi.org/10.1101/2020.10.22, 2020).

Viral tropism and infectivity are greatly determined by the expression of cellular receptors and entry cofactors on the cell surface. Thus, having demonstrated that IL12RB1, IL1RAPL2, NRP2 and CNTN1 are previously unrecognized cellular factors that directly interact with the SARS-CoV-2 spike, the expression patterns of these human factors were next analyzed using published databases, both at the tissue level (The Human Protein Atlas) and in single cell transcriptomes in the major organs (Han et al., Nature, 581: 303-309, 2020; Durante et al., Nat Neurosci, 23: 323-326, 2020).

Figure 3A:
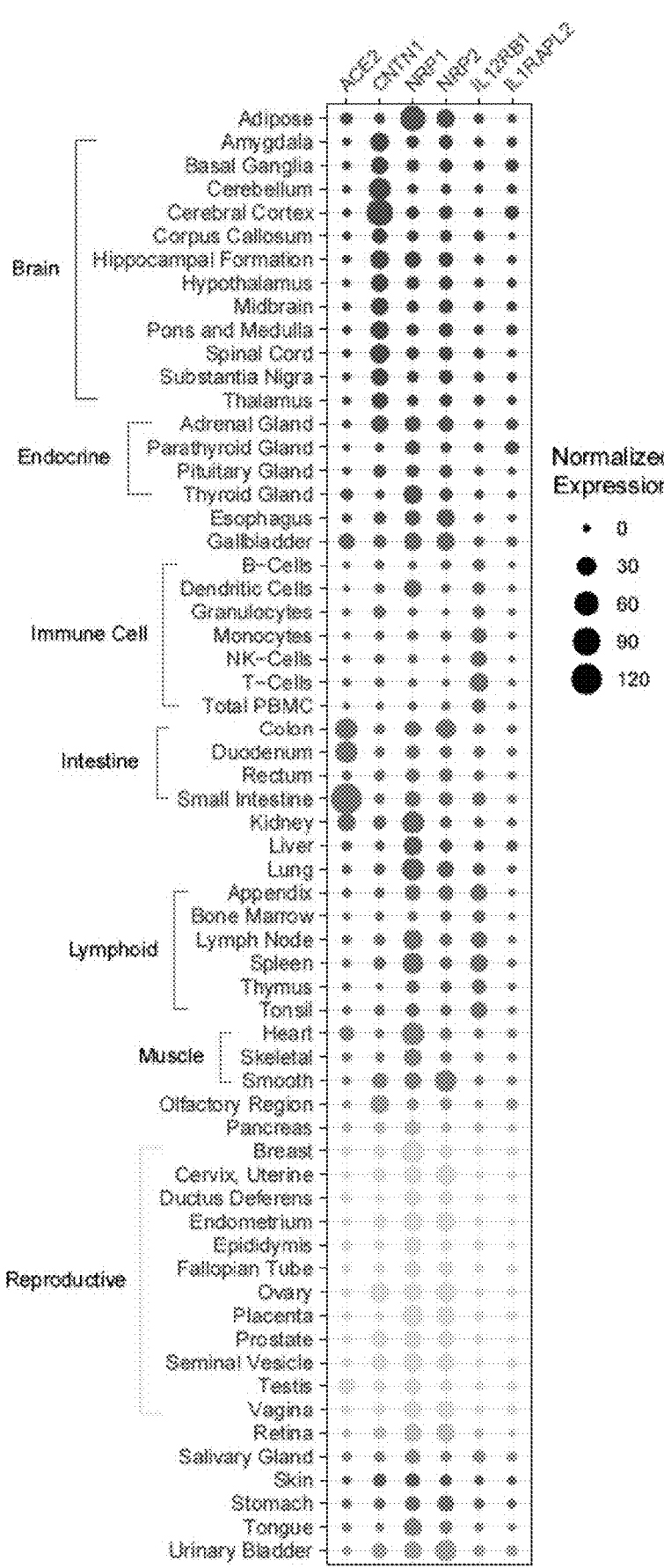
FIG. 3A is a dotplot showing RNA expression of SARS CoV-2 spike binding partners across human tissues (RNAseq data from Human Protein Atlas). Normalized expression levels are indicated by the size of the dot.
Figure 3B:
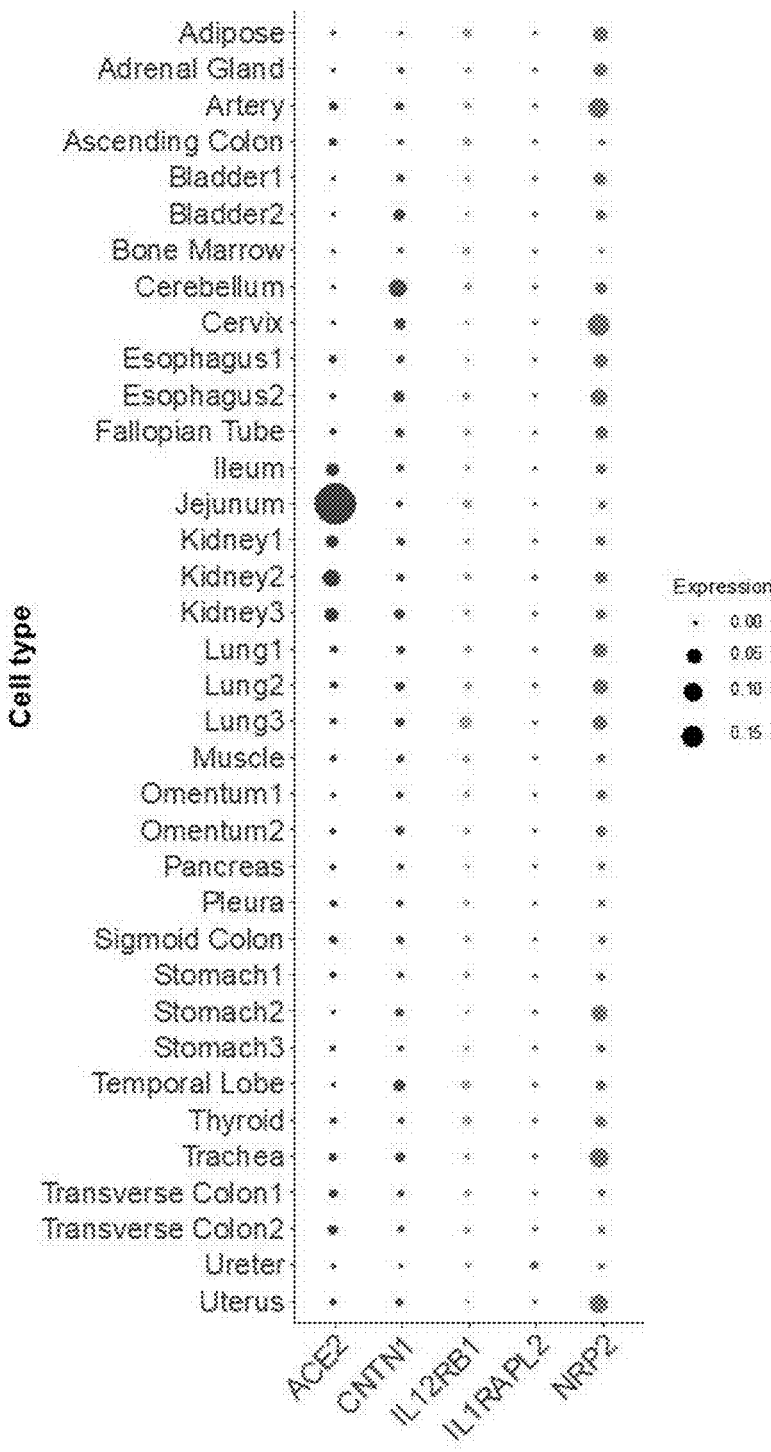
FIG. 3B is a dot showing expression of ACE2 and the additional spike protein receptors IL12RB1, IL1RAPL2, NRP2 and CNTN1 in single-cell (sc) RNAseq data in 36 different tissue types in healthy individuals. scRNAseq data were obtained from GSE13455. Expression levels are indicated by the size of the dot.
Figure 3C:
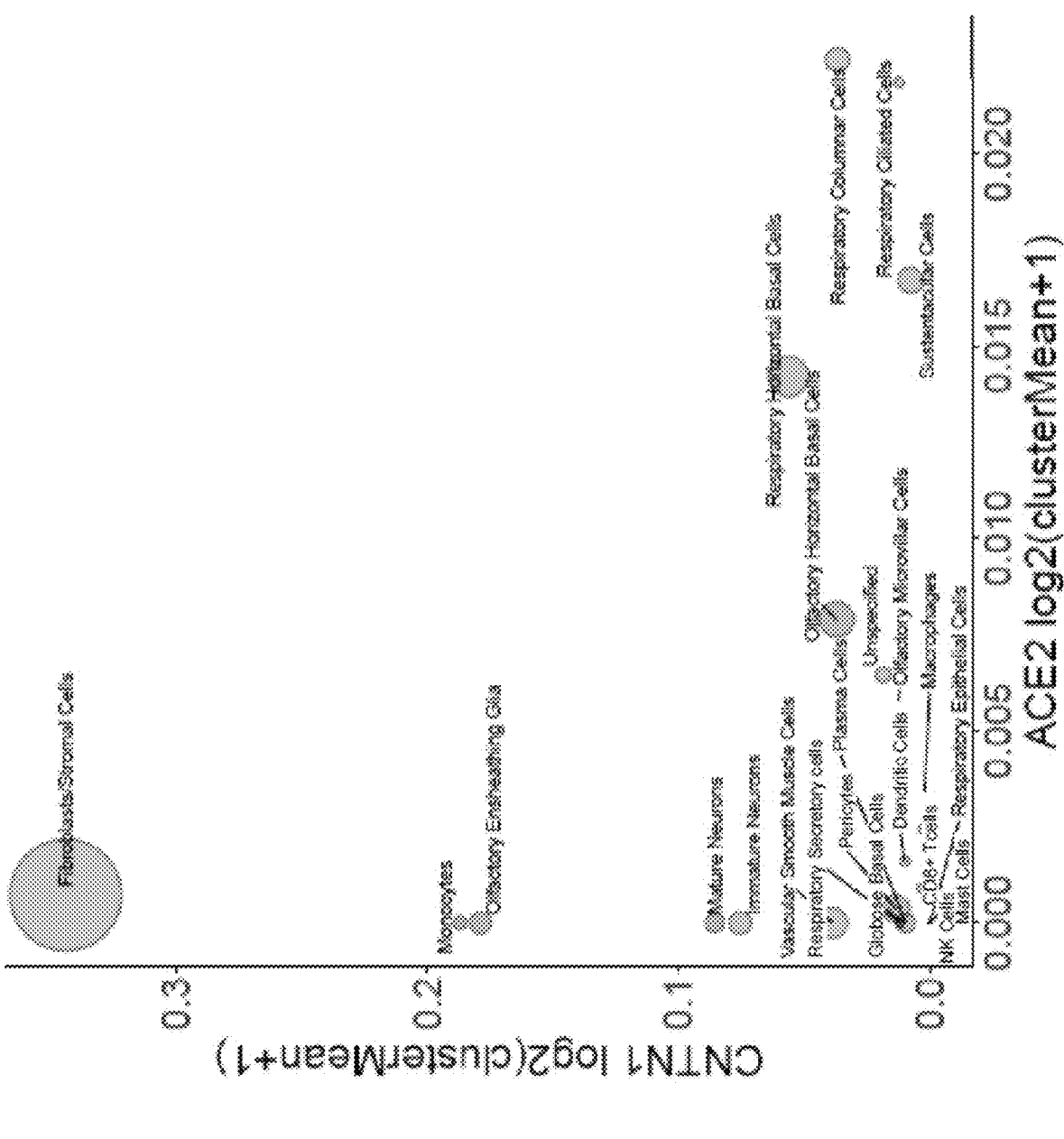
FIG. 3C is a bubble plot showing the expression levels of ACE2 and CNTN1 in the indicated cell types. N=26. Size of bubbles represents the number of cells expressing the receptors. Size of bubbles represents the number of cells expressing the spike protein receptors. scRNAseq data were obtained from GSE139522.

IL1RAPL2 showed overall low expression levels both at the tissue and single cell (scRNA) level in most tissues (FIGS. 3A and 3B). In contrast, IL12RB1 was predominantly expressed in immune and lymphoid cells (FIG. 3A), showing relatively higher expression scRNA transcriptomes from lung cells (FIG. 3B). NRP2 was broadly represented and highly expressed in brain, reproductive and gastrointestinal tissues (FIG. 3A), as well as lung, esophagus or tracheal cellular types at the single cell level (FIG. 3B). scRNAseq data for FIGS. 30 to 3K was obtained from GSE139522.

Figure 3D:
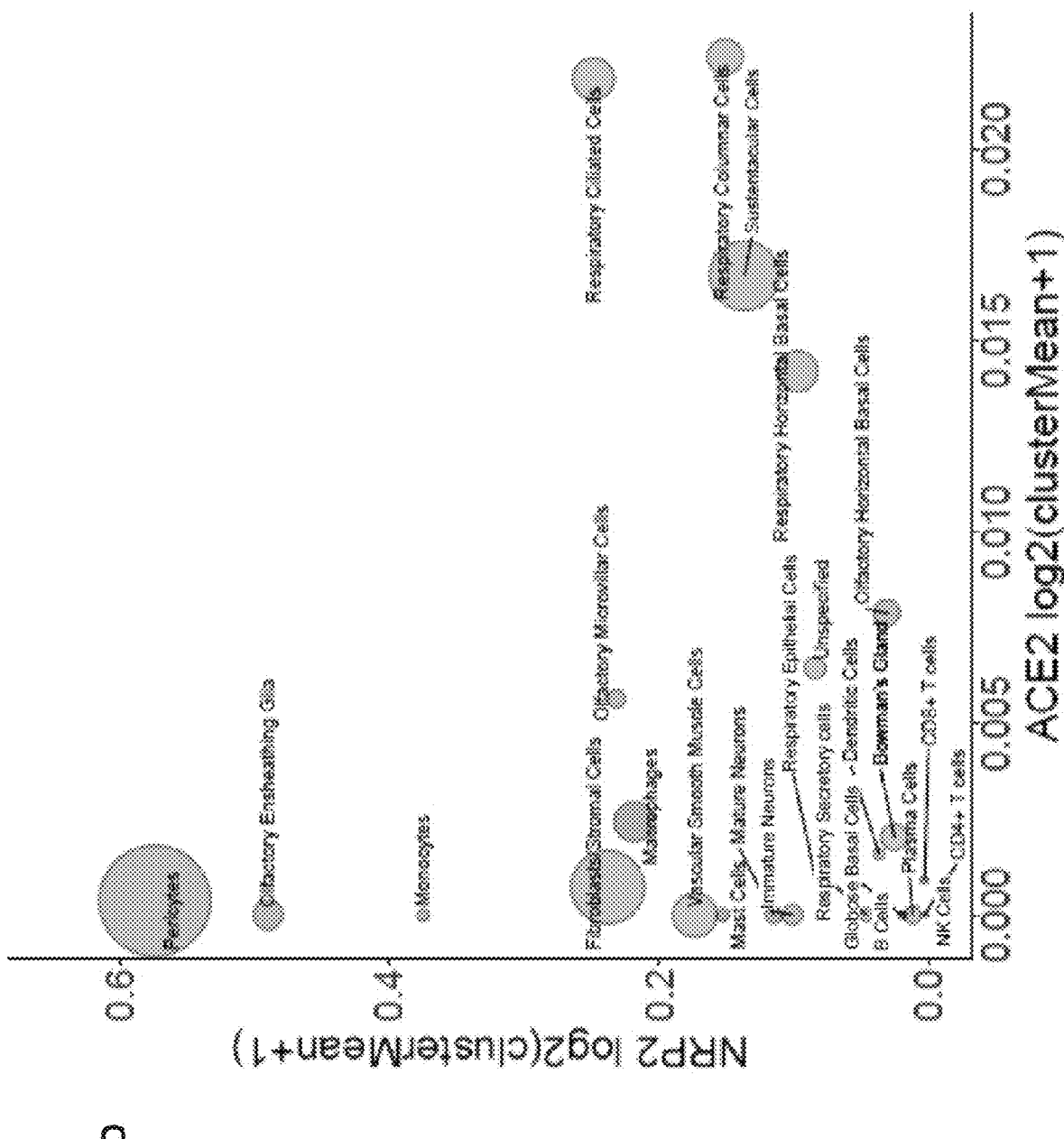
FIG. 3D is a bubble plot showing the expression levels of ACE2 and NRP2 in the indicated cell types. N=26. Size of bubbles represents the number of cells expressing the receptors. Size of bubbles represents the number of cells expressing the spike protein receptors. scRNAseq data were obtained from GSE139522.
Figure 3E:
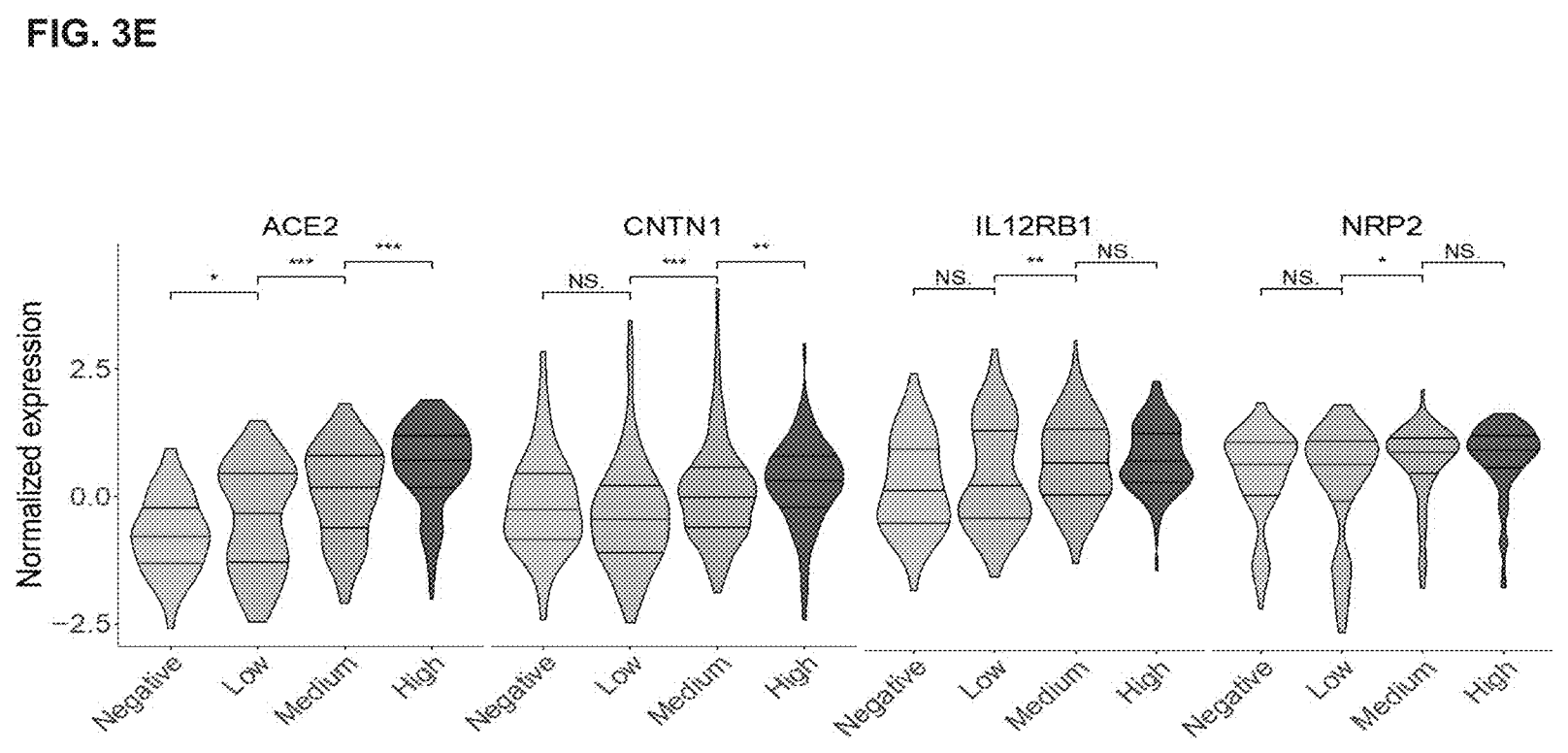
Figure 3F:
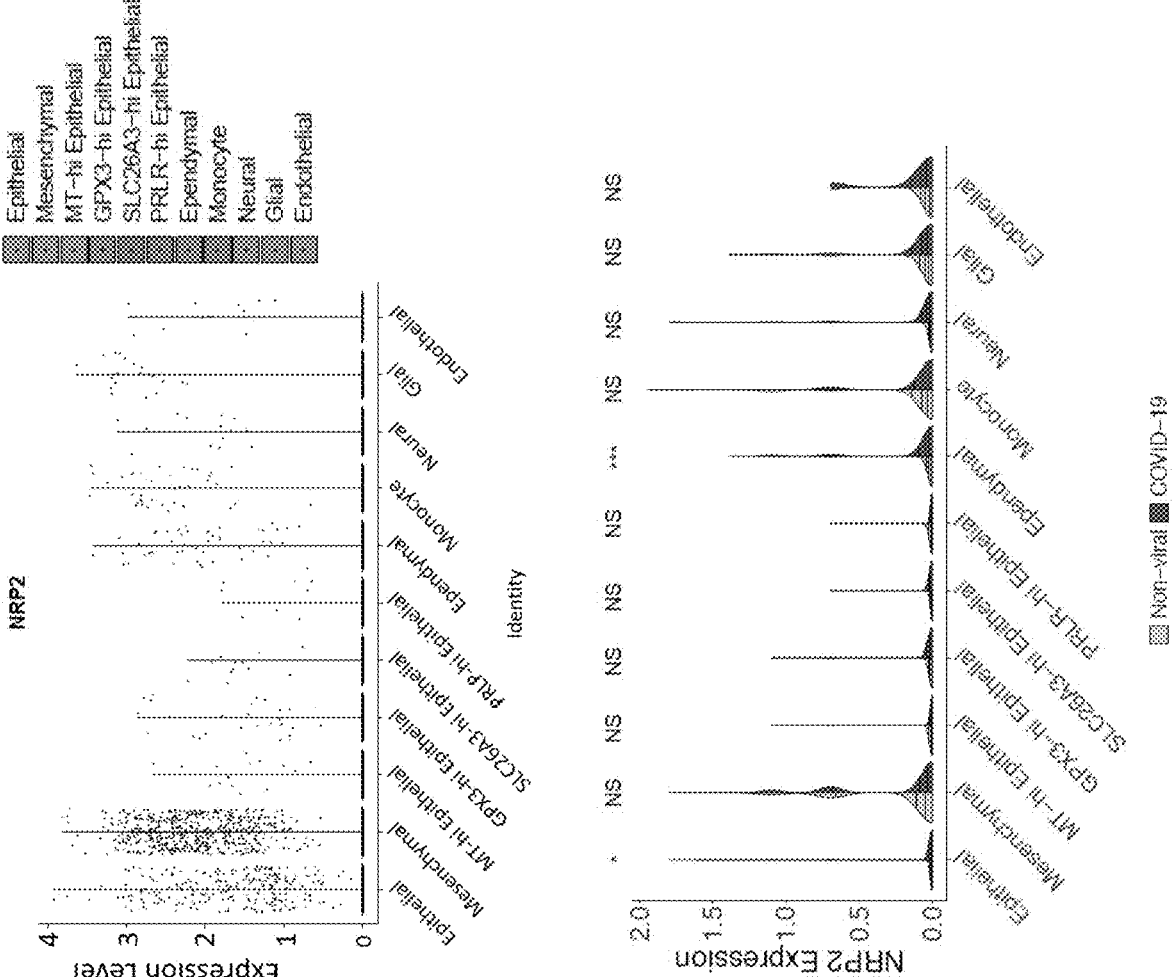
FIG. 3F is a set of violin plots showing expression of NRP2 in different cell clusters from choroid plexus (top panel) and a set of split violin plots showing the differential gene expression of NRP2 between non-viral and COVID-19 infected individuals in each cell type collected from choroid plexus (bottom panel). *p<0.05, p<0.01, *p<0.001, NS, Not significant.
Figure 3G:
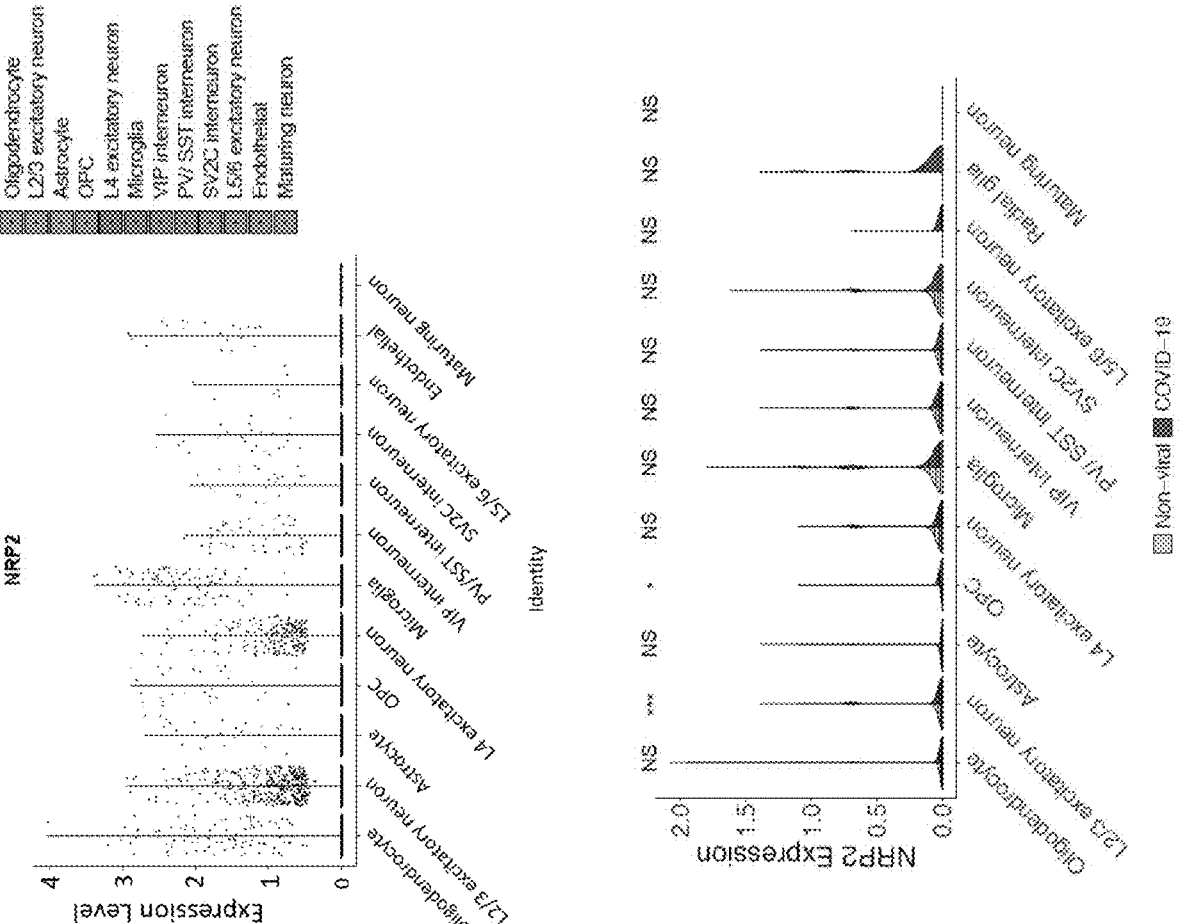
FIG. 3G is a set of violin plots showing expression of NRP2 in different cell clusters from brain parenchyma (top panel) and a set of split violin plots showing the differential gene expression of NRP2 between non-viral and COVID-19 infected individuals in each cell type collected from brain parenchyma (bottom panel). *p<0.05, p<0.01, *p<0.001, NS, Not significant.
Figure 3H:
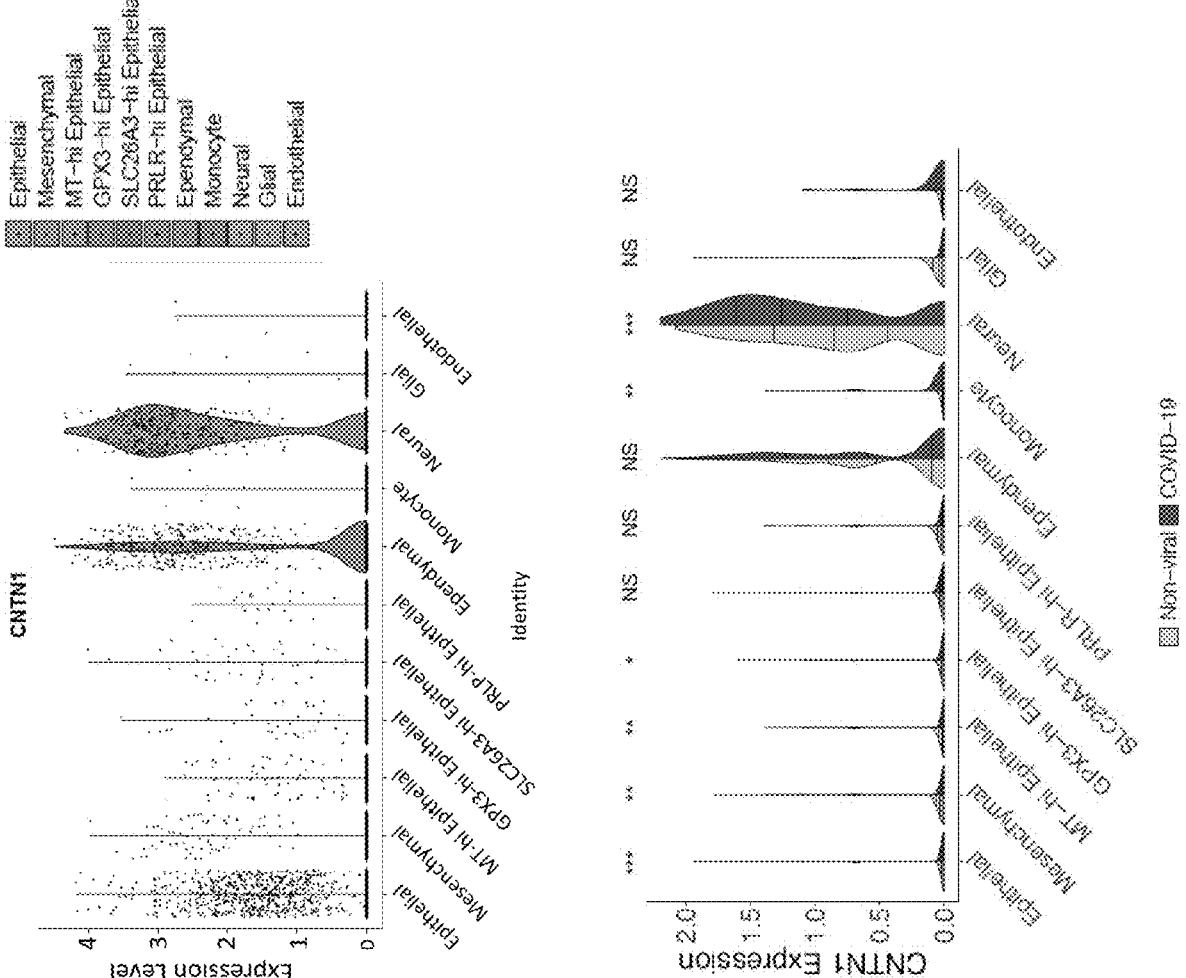
FIG. 3H is a set of violin plots showing expression of CNTN1 in different cell clusters from choroid plexus (top panel) and a set of split violin plots showing the differential gene expression of CNTN1 between non-viral and COVID-19 infected individuals in each cell type collected from choroid plexus (bottom panel), *p<0.05, p<0.01, *p<0.001, NS, Not significant.
Figure 31:
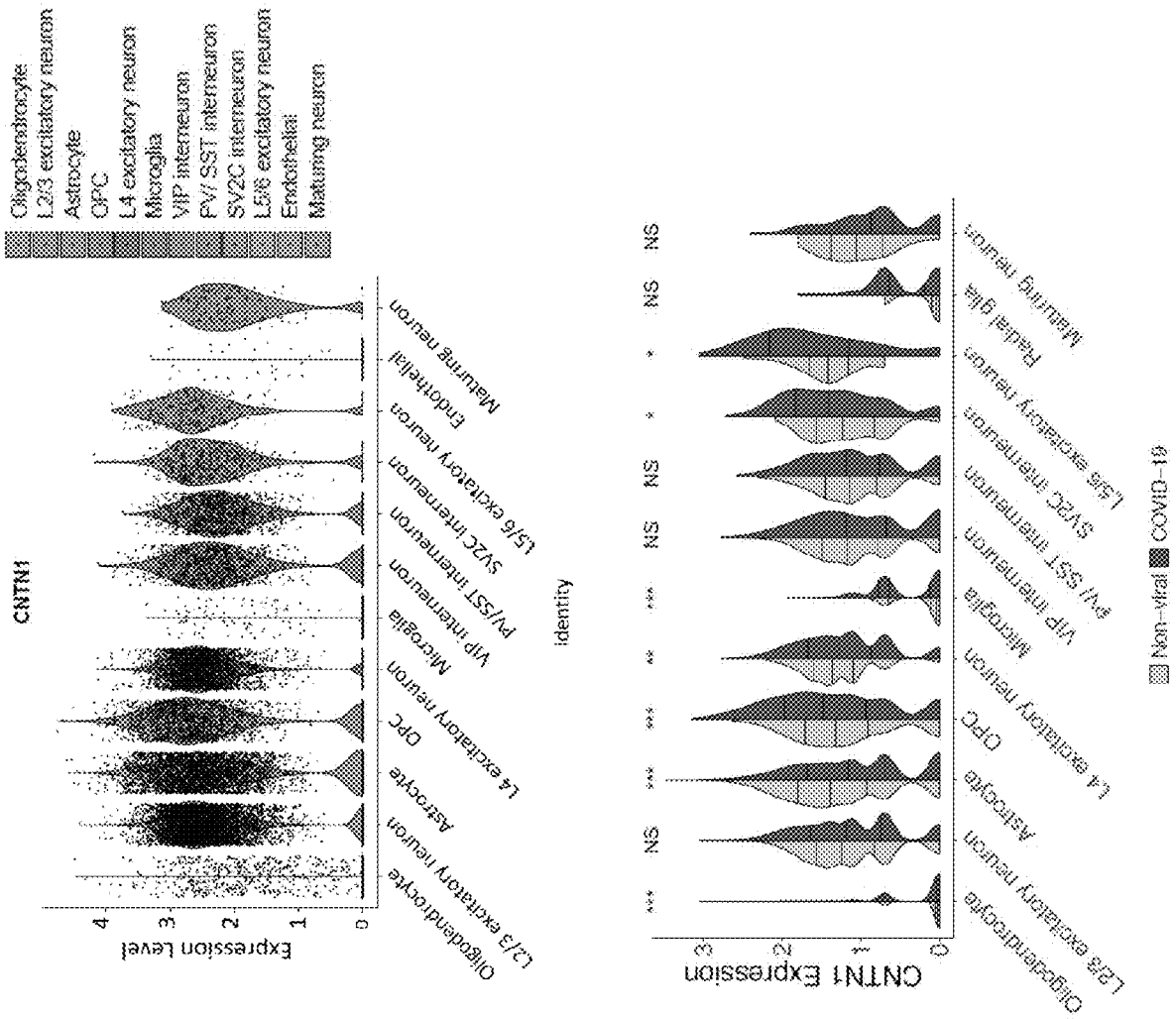

Interestingly, CNTN1 was predominantly expressed in nervous system tissue and was moderately present in tissues relevant for viral infection, such as lung or esophagus (FIG. 3A). A hallmark of COVID-19 infection is olfactory dysfunction, which could be explained in part by the ability of the virus to directly infect the olfactory epithelium (Fuccillo et al., J Laryngol Otol, 1-10, 2020). To assess whether the newly identified RBD receptors were expressed in this tissue, a recently published map of the human olfactory tissue at the single cell level was queried (Durante et al., Nat Neurosci, 23: 323-326, 2020) (FIGS. 3C, 3D, and 7A-7G). Interestingly, while ACE2 was overall expressed only at low levels, CNTN1 was prominently expressed in several cell types, including stromal cells, monocytes and neurons, showing low co-expression with ACE2 in certain populations such as olfactory and respiratory horizontal basal cells (FIGS. 3D and 3H).

In turn, NRP2 showed high expression in different cell types, with the highest relative levels in pericytes, glia or vascular smooth muscle cells, among others (FIG. 3D). In keeping with previous observations, IL12RB1 was predominantly expressed in immune cell populations in the olfactory epithelium, whereas IL1RAPL2 expression was overall very low in this tissue (FIGS. 7A-7G).

Analysis of Tissue Expression for RBD Binding Partners

RNA consensus tissue gene data was downloaded from the Human Protein Atlas webpage (HPA v19.3), which contains normalized expression data between the HPA, GTEx and FANTOMS expression datasets. General tissue categories were designated based on GTEx labels and Tissue Atlas labels.

Next Generation Sequencing Data Analysis

For the single cell RNAseq (scRNAseq) data from healthy individuals, the original digital gene expression (DGE) for different tissue samples reported by Han et al., Nature, 581: 303-309, 2020 (GSE134355) was used. Only adult tissues were analyzed. CNTN1 was detected in 36 different tissues. Another human olfactory and respiratory mucosal cell scRNAseq dataset reported by Durante et al., Nat Neurosci, 23: 323-326, 2020 was collected from GSE139522. The UMAP coordinates and cell cluster annotations were based on the publication. The RNAseq dataset of nasopharynx swab from individuals with and without SARS-CoV-2 infection reported by Lieberman et al., PLoS Biol, 18: e3000849, 2020 (described in Example 5) was obtained from GSE152075. The raw count gene expression data was normalized using trimmed mean of M-values (TMM) and transformed with VOOM to log 2-counts per million with associated precision weights. The association between the normalized, log 2 transformed gene expression and infection status as well as viral load was analyzed. The infection status and viral load data were obtained from the metadata available in GSE152075. Statistical significance between groups is calculated by Mann Whitney U test. The scRNAseq data of brain and choroid plexus cell types from healthy and COVID-19 infected individuals was reported by Yang et al., bioRxiv, doi.org/10.1101/2020.10.22, 2020. The data contained 47,678 droplet-based single-nucleus transcriptomes from the frontal cortex and choroid plexus across 10 nonviral and 4 COVID-19 individuals. 23,626 nuclei across 8 major cell types were profiled in the cortex and 24,052 nuclei across 7 cell types in the choroid plexus. The UMAP coordinates and cell cluster annotations were based on the publication.

Example 5. Expression of SARS-CoV-2 Spike
Protein RBD Binders During Infection

To gain insights into the putative roles of the novel spike protein RBD binding receptors during infection, the expression of these cellular factors during infection was investigated using publicly available databases. First, a recently published dataset of gene expression profiles from nasopharyngeal swabs from over 400 COVID-19 patients and healthy controls was queried (Lieberman et al., PLoS Biol, 18: e3000849, 2020). In agreement with the low expression levels observed in other tissues, IL1RAPL2 expression was not detected in these samples. Notably, whereas levels of IL12RB1 and NRP2 were only moderately increased as a function of viral load (FIG. 8B), and CNTN1 expression level was significantly correlated with viral load and disease severity in the COVID-19 patients (FIG. 3E), an association that was more evident in older patients (FIG. 8A).

Interestingly, and similar to CNTN1, ACE2 expression was significantly associated with viral load in this patient cohort (FIG. 3E). Next, a recent study on single nucleus RNA transcriptomes from the frontal cortex and choroid plexus in 10 healthy and 4 COVID-19 patients was utilized (Yang et al., bioRxiv, doi.org/10.1101/2020.10.22.349415, 2020) (FIGS. 9A-9D). Importantly, of the spike receptors identified in this study, CNTN1 expression was significantly higher in choroid plexus and frontal cortex (FIGS. 3H and 3I), and was also higher in relation to NRP2, which was expressed only at relatively low levels (FIG. 3I). Interestingly, ACE2 expression was very low or negligible (FIGS.

9A-9D), despite immunohistochemistry analysis that demonstrated substantial viral load in these brain tissues (Yang et al., *bioRxiv*, doi.org/10.1101/2020.10.22.349415, 2020), supporting numerous in vitro, in silico and post-mortem studies that have indicated that central nervous system cells can support productive SARS CoV-2 infection (Jakhmola et al., *Sn Compr Clin Med*, 1-10, 2020; Alomari et al., *Clin Neurol Neurosurg*, 198: 106116, 2020; Baig et al., *ACS Chem Neurosci*, 11: 995-998, 2020; Li et al., *J Med Virol*, 92: 552-555, 2020; Ellul et al., *Lancet Neurol*, 19: 767-783, 2020; Jacob et al., *Cell Stem Cell*, doi:10.1016/j.stem.2020.09.016, 2020). By contrast, CNTN1 was broadly and highly expressed in most cell types, in particular ependymal and neural cells in the choroid plexus and the parenchyma (FIGS. 3H, 3I, and 9A-9D). NRP2, recently identified as an enhancement factor of ACE2-mediated infection, showed significant upregulation in discrete populations of the COVID-19 brain (FIGS. 3F, 3G, and 9A-9D). In contrast, CNTN1 was consistently and significantly elevated in most cell types in both frontal cortex and choroid plexus, showing a particularly prominent upregulation across most cellular populations in the brain parenchyma (FIGS. 3I and 9A-9D) and neural cells within the choroid plexus (FIGS. 3H and 9A-9D). Together, these findings raise the possibility that CNTN1 may play a role in viral infection of nervous system cells or associated tissues such as the olfactory epithelium, susceptible cellular types that have been shown to support viral infection through mechanisms that remain unclear (Pellegrini et al., *bioRxiv*, doi:10.1101/2020.08.20.259937, 2020; Yang et al., *bioRxiv*, doi.org/10.1101/2020.10.22.349415, 2020).

Example 6. Role of SARS-CoV-2 Spike Protein RBD Binders in Viral Entry

Figure 4A:
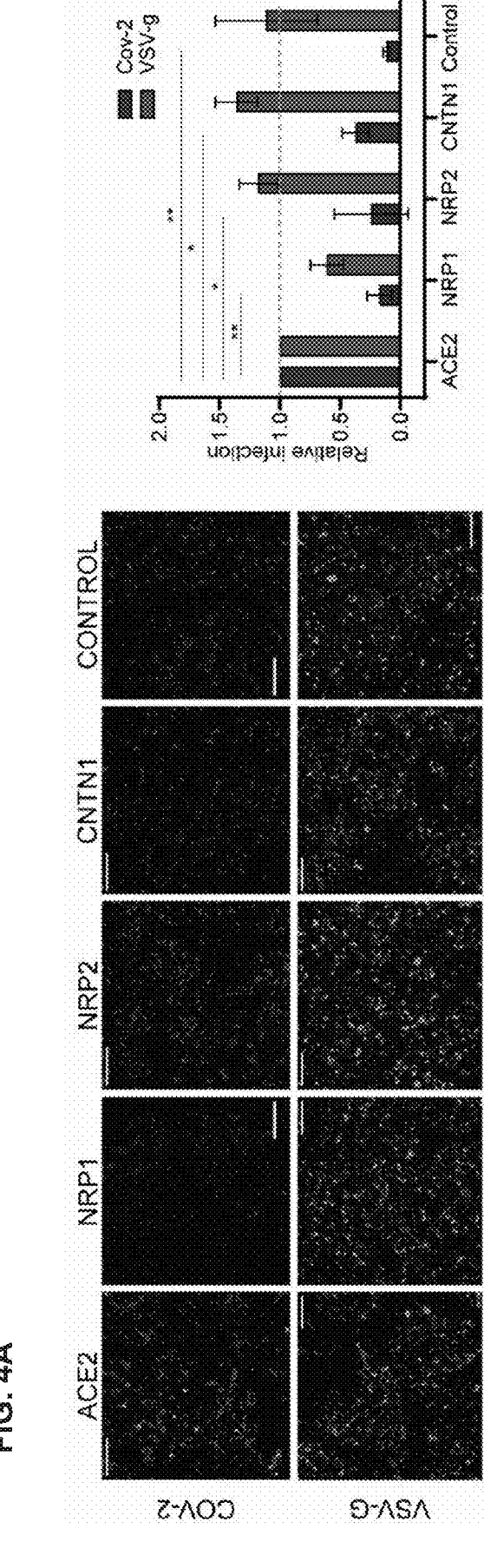
FIG. 4A is a set of representative micrographs showing SARS CoV-2 pseudotyped particle infection of HEK/293T cells transiently expressing a control vector or the SARS CoV-2 RBD receptor ACE2, CNTN1, NRP1 or NRP2 and a bar graph showing quantification of infection. Blue bars show quantification for SARS CoV-2 pseudotyped particles. Grey bars show vesicular stomatitis virus G (VSV-G) pseudotyped activity, used as a control. Data were normalized to the respective infection of SARS CoV-2 and VSV-G particles in ACE2-expressing cells. Infected cells are represented in green; nuclei are depicted in blue. Scale bar=200 μm. Two-way ANOVA with Sidak's correction for multiple comparisons; *p<0.05, p<0.01, *p<0.001. NS, not significant.
Figure 4B:
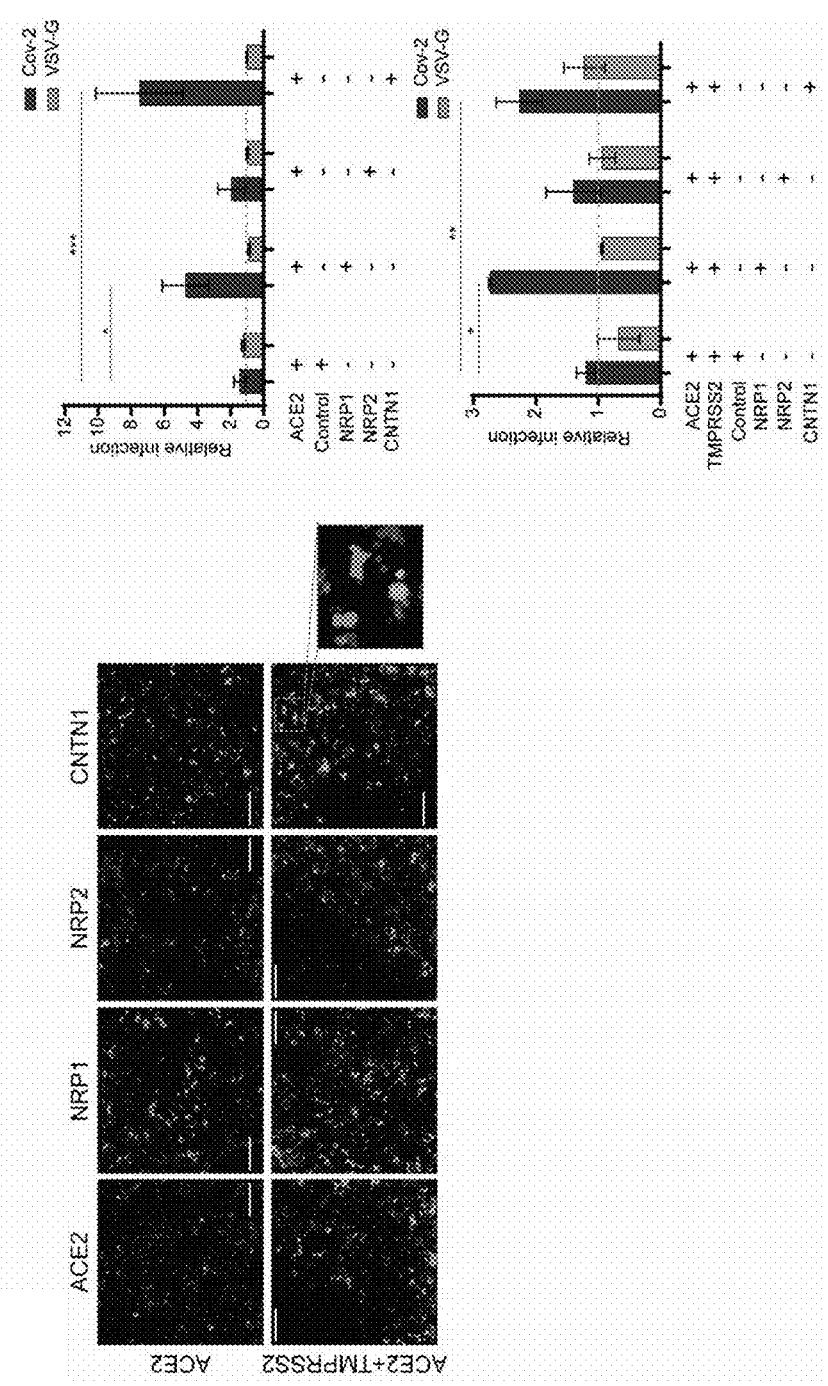
FIG. 4B is a set of representative micrographs showing SARS CoV-2 pseudotyped particle infection of HEK/293T cells transiently expressing the SARS CoV-2 RBD receptor ACE2 or ACE2 and TMPRSS2 and transfected with CNTN1, NRP1, and NRP2 and a bar graph showing quantification of infection. Blue bars show quantification for SARS CoV-2 pseudotyped particles. Grey bars show VSV-G pseudotyped activity, used as a control. Data were normalized to infection in ACE2-expressing or ACE2+TMPRSS2-expressing cells, respectively. Infected cells are represented in green; nuclei are depicted in blue. Scale bar=200 μm. Two-way ANOVA with Sidak's correction for multiple comparisons; *p<0.05, p<0.01, *p<0.001. NS, not significant.

Having demonstrated that the SARS-CoV-2 spike trimer directly binds to select host factors beyond ACE2 in an interaction mediated by the RBD, and in light of the evidence showing that these host factors are expressed in relevant tissues during COVID-19 infection, the role of these receptors in viral entry was investigated. Viral particles pseudotyped with SARS-CoV-2 spike protein, which specifically allow the study of viral entry, were used. HEK/293 cells, which express no detectable ACE2, were transfected with plasmids encoding the host factors identified as binding partners for the RBD. ACE2 expression made the cells susceptible to infection, as expected, whereas CNTN1 expression by itself promoted only very low levels of infection (FIG. 4A). Remarkably, CNTN1 co-expression with ACE2 significantly increased pseudotyped particle infection relative to cells expressing only ACE2 (FIG. 4B). Furthermore, CNTN1 also promoted infection in the presence of ACE2 and TMPRSS2 (FIG. 4B), altogether indicating that CNTN1 serves as a cellular factor that enhances ACE2-dependent infection. In contrast, CNTN1 did not have a significant effect on levels of vesicular stomatitis virus (VSV) glycoprotein pseudotyped particle infection (used as a control), consistent with the fact that infection by this virus does not rely on ACE2 (FIGS. 4A and 4B).

NRP2 expression did not promote infection, but increased viral entry when co-expressed with ACE2 or ACE2 and TMPRSS2, as recently reported for the related receptor NRP1 (Cantuti-Castelvetri et al., *Science*, 370: 856-860, 2020; Daly et al., *Science*, 370: 861-865, 2020) (FIGS. 4A and 4B). In contrast, IL12RB1 and IL1RAPL2 expression did not significantly influence viral entry under the experimental conditions tested (FIGS. 10A and 10B), suggesting that these factors may play a role in other aspects of the viral cycle. A plausible hypothesis is that SARS-CoV-2 infection might modulate inflammation through interference with IL-12/IL-23 signaling, via direct targeting of IL12RB1, an axis frequently involved in autoimmune disease and bacterial infection (Robinson et al., *Cytokine*, 71: 348-359, 2015; van de Vosse et al., *Hum Mutat*, 34: 1329-1339, 2013). Moreover, IL1RAPL2, a protein predominantly expressed in the brain, may function as an accessory protein for surface receptors and could influence viral attachment and dissemination in the nervous system (Booker and Grattan, *J Immunol*, 198: 270-278, 2017; Bahi et al., *Hum Mol Genet*, 12: 1415-1425, 2003).

Infection Assays with SARS CoV-2 Spike Pseudotyped Particles

Replication incompetent vesicular stomatitis virus (VSV) strain Indiana particles displaying glycoprotein G (VSV-G) and carrying a GFP reporter were purchased from Integral Molecular (Philadelphia, USA). The viral particles pseudotyped with SARS CoV-2 spike protein carrying a GFP reporter were also purchased from Integral Molecular. For the infection assays with the pseudotyped particles, HEK/293T cells were seeded on M96 or M384 well plates. Cells were transiently transfected with an empty plasmid control or the spike binding partners as full-length, native proteins, and cell cultures were infected 24 hours or 48 hours post-transfection to enable expression of the cellular receptors. Pseudotyped particles were diluted in serum free DMEM media and incubated with the cells for 4 hours at 37° C., after which the growth media was replaced with DMEM containing 10% FBS. After 24 hours or 48 hours post-infection, the cells were washed, fixed with 4% PFA, and stained with DAPI (Thermo Scientific) to visualize nuclei. Images were acquired with a high content microscope (InCell 6000, GE Healthcare) or Leica SP5 confocal (Leica) at 10× magnification. For quantification of infection, images were analyzed with the InCell Developer software version 4.1. Infection was represented relative to that observed for ACE-2 expressing cells in each group. Two-way ANOVA was carried out with Sidak's correction for multiple comparisons using the Graph Pad software v8.

CONCLUSION

Viral proteins can target multiple host factors, often by exploiting multivalent protein-protein interactions to increase affinity and potency, activities that grant the virus the potential to interfere with several host functions using limited genomic resources (Martinez-Martin et al., *Nat Commun*, 7: 11473, 2016). The differences in the extracellular interactome of the SARS-CoV-2 spike identified in the current study may increase the functionality of this protein, acting as a contributing factor to the broader tropism and increased infectivity of the virus, including its ability to infect the nervous system and the olfactory epithelium, where these receptors are predominantly expressed. As such, it is plausible that CNTN1 acts as an enhancement factor that facilitates entry in cells expressing low levels of ACE2, or potentiates infection of ACE2-expressing cells in the tissue microenvironment. Developing reagents that selectively block the interaction between CNTN1 and SARS CoV-2 spike thus offers a potential route for therapeutic intervention that might help decrease viral infection and spread. This study represents an important resource to study virus-host interactions at the molecular level, and highlights targets that may influence the increased tropism and neuro-invasive potential of SARS-CoV-2.

Further, the finding that the cell-associated factor CNTN1 acts as a SARS CoV-2-specific host receptor provides a potential route by which the virus may target neural cells, especially in light of the very low expression level of ACE2 expression in the brain. Our results demonstrating that CNTN1 promotes SARS-CoV-2 infection of cells expressing low levels of ACE2 supports similar recent findings for neuropilins.

CNTN1 may play a role in tissues where ACE2 levels are low, such as the brain choroid plexus (FIGS. 3A-3I). Alternatively, or in addition, CNTN1 may mediate ACE2-independent routes of infection in vivo in inflamed tissues with high viral load, or potentiate infection of adjacent ACE2-expressing cells in the tissue microenvironment.

The novel SARS CoV-2 spike cellular receptors identified in this study may in part explain the broader tropism and increased infectivity of the virus, including its ability to infect the nervous system and the olfactory epithelium, where CNTN1 is predominantly expressed. The novel SARS-CoV-2 represents a global pandemic expected to have a long-lasting impact on human health, and clearly future investigations on the role of these novel spike receptors are warranted. For example, developing reagents that selectively block the interaction between CNTN1 and the spike protein offers a potential route for therapeutic intervention that might help decrease viral infection and spread. More generally, the receptor discovery platform described herein represents an important resource to study virus-host interactions at the molecular level, and highlights targets that may influence the increased tropism and neuro-invasive potential of viruses like SARS-CoV-2. Ultimately, these findings pave the way for new or improved therapeutic options against SARS-CoV-2 and other viral threats to global human health.

This study provides the first systematic analysis of the host factors directly targeted by the SARS CoV spike, the main protein responsible for viral tropism.

---

What is claimed is:

1. A method of treating an individual having a SARS-CoV-2 infection comprising administering to the individual an effective amount of a contactin-1 (CNTN1) antagonist, an interleukin 12 receptor subunit beta 1 (IL12RB1) antagonist, or an interleukin 1 receptor accessory protein like 2 (IL1RAPL2) antagonist.

2. A method of reducing SARS-CoV-2 attachment to a cell of an individual comprising administering to the individual an effective amount of a CNTN1 antagonist, an IL12RB1 antagonist, or an IL1RAPL2 antagonist.

3. The method of claim 2, wherein the administering comprises contacting the cell of the individual with an effective amount of a CNTN1 antagonist, an IL12RB1 antagonist, or an IL1RAPL2 antagonist.

4. The method of claim 1, wherein:

(a) the CNTN1 antagonist results in a decrease in the binding of CNTN1 and the SARS-CoV-2 spike (S) protein relative to binding of the two proteins in the absence of the antagonist;

(b) the IL12RB1 antagonist results in a decrease in the binding of IL12RB1 and the SARS-CoV-2 S protein relative to binding of the two proteins in the absence of the antagonist; or (c) the IL1RAPL2 antagonist results in a decrease in the binding of IL1RAPL2 and the SARS-CoV-2 S protein relative to binding of the two proteins in the absence of the antagonist.

5. The method of claim 1, wherein the CNTN1 antagonist, IL12RB1antagonist, or IL1RAPL2 antagonist is a small molecule, an antibody or antigen-binding fragment thereof, a peptide, a mimic, or an inhibitory nucleic acid.

6. The method of claim 5, wherein:

(a) the antibody or antigen-binding fragment thereof binds the SARS-CoV-2 S protein and inhibits its binding to CNTN1, IL12RB1, and/or IL1RAPL2; or (b) the antibody or antigen-binding fragment thereof binds CNTN1, IL12RB1, or IL1RAPL2and inhibits the binding of CNTN1, IL12RB1, or IL1RAPL2 to the SARS-CoV-2 S protein.

7. A method of prophylaxis against secondary infection of nervous tissue in an individual having a SARS-CoV-2 infection comprising administering to the individual an effective amount of a CNTN1 antagonist or an IL1RAPL2 antagonist.

8. A method of prophylaxis against secondary infection of immune cells and/or lymphoid tissue in an individual having a SARS-CoV-2 infection comprising administering to the individual an effective amount of an IL12RB1 antagonist.

9. A method of prophylaxis against secondary infection of the lungs in an individual having a SARS-CoV-2 infection comprising administering to the individual an effective amount of a CNTN1 antagonist or an IL12RB1 antagonist.

10. The method of claim 1, further comprising administering to the individual at least one additional therapy, wherein the at least one additional therapy is one or more of an IL-6 antagonist, an angiotensin-converting enzyme 2

(ACE2) antagonist, a neuropilin-2 (NRP2) antagonist, oxygen therapy, anti-viral therapy, or a corticosteroid therapy.

11. A method of identifying a modulator of the interaction between the SARS-CoV-2 S protein and CNTN1, IL12RB1, or IL1RAPL2, the method comprising:

(a) providing a candidate modulator;

(b) contacting the SARS-CoV-2 S protein RBD with CNTN1, IL12RB1, or IL1RAPL2 in the presence or absence of the candidate modulator under conditions permitting the binding of the SARS-CoV-2 S protein RBD to CNTN1, IL12RB1, or IL1RAPL2; and (c) measuring the binding of the protein of the SARS-CoV-2 S protein RBD to CNTN1,IL12RB1, or IL1RAPL2, wherein an increase or decrease in binding in the presence of the candidate modulator relative to binding in the absence of the candidate modulator identifies the candidate modulator as a modulator of the interaction between the SARS-CoV-2 S protein and CNTN1, IL12RB1, or IL1RAPL2.

12. The method of claim 11, wherein the modulator is an inhibitor of the downstream activity of the SARS-CoV-2 S protein or CNTN1, IL12RB1, or IL1RAPL2.

13. The method of claim 11, wherein the modulator is a small molecule, an antibody or antigen-binding fragment thereof, a peptide, a mimic, or an inhibitory nucleic acid.

14. The method of claim 13, wherein:

(a) the antibody or antigen-binding fragment thereof binds the SARS-CoV-2 S protein RBD; or (b) the antibody or antigen-binding fragment thereof binds CNTN1, IL12RB1, or IL1RAPL2.

15. The method of claim 12, wherein the downstream activity is infection of a cell by SARS-CoV-2.

16. A pharmaceutical formulation comprising a modulator of the interaction between the SARS-CoV-2 S protein and CNTN1, IL12RB1, or IL1RAPL2, wherein the modulator causes a decrease in the binding of the SARS-CoV-2 S protein to CNTN1, IL12RB1, or IL1RAPL2 relative to binding in the absence of the modulator.

17. The pharmaceutical formulation of claim 16, wherein the decrease in binding is at least 50%, as measured by surface plasmon resonance, biolayer interferometry, or an enzyme-linked immunosorbent assay (ELISA).

18. The pharmaceutical formulation of claim 16, wherein the modulator is an inhibitor of the downstream activity of the SARS-CoV-2 S protein or CNTN1, IL12RB1, or IL1RAPL2.

19. The pharmaceutical formulation of claim 16, wherein the modulator is a small molecule, an antibody or antigen-binding fragment thereof, a peptide, a mimic, or an inhibitory nucleic acid.

20. The pharmaceutical formulation of claim 19, wherein:

(a) the antibody or antigen-binding fragment thereof binds the SARS-CoV-2 S protein RBD; or (b) the antibody or antigen-binding fragment thereof binds CNTN1, IL12RB1, or IL1RAPL2.

* * * * *

SEQUENCE LISTING

```
Sequence total quantity: 8
SEQ ID NO: 1            moltype = AA  length = 1240
FEATURE                 Location/Qualifiers
source                  1..1240
                        mol_type = protein
                        organism = Severe acute respiratory syndrome coronavirus 2
                        note = SARS-CoV-2
SEQUENCE: 1
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PGSASSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA 1020
SANLAATKMS ECVLGQSKRV DFCGKGYHLM SPPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQGS GYIPEAPRDG QAYVRKDGEW VLLSTFLGGG                       1240

SEQ ID NO: 2            moltype = DNA  length = 3720
FEATURE                 Location/Qualifiers
misc_feature            1..3720
                        note = Synthetic Construct
source                  1..3720
                        mol_type = other DNA
                        organism = synthetic construct
SEQUENCE: 2
atgttcgtgt ttctggtgct gctgcctctg gtgagctccc agtgcgtgaa cctgaccaca   60
aggacccagc tgccacctgc ctataccaat tccttcacac ggggcgtgta ctatcctgac  120
aaggtgttta gatctagcgt gctgcactct acacaggatc tgtttctgcc attctttagc  180
aacgtgacct ggttccacgc catccacgtg agcggcacca atggcacaaa gcggttcgac  240
aatcctgtgc tgcccttcaa cgatggcgtg tacttcgcct ccaccgagaa gtctaacatc  300
atcagaggct ggatctttgg caccacactg gacagcaaga cacagtccct gctgatcgtg  360
aacaatgcca ccaacgtggt catcaaggtg tgcgagttcc agttttgtaa tgatcccttc  420
ctgggcgtgt actatcacaa gaacaataag tcttggatgg agagcgagtt tagagtgtat  480
tcctctgcca acaattgtac atttgagtac gtgtcccagc cttttcctga tggacctggag  540
ggcaagcagg gcaatttcaa gaacctgagg gagttcgtgt ttaagaatat cgatggctac  600
ttcaagatct actccaagca cacccccatc aacctggtgc gcgacctgcc tcagggcttc  660
tctgccctgg agcccctggt ggatctgcct atcggcatca acatcacccg gtttcagaca  720
ctgctggccc tgcacagaag ctacctgaca cccggcgaca gctcctctgg atggaccgca  780
ggagcagcag cctactatgt gggctatctg cagcctagga ccttcctgct gaagtacaac  840
gagaatggca ccatcacaga cgcagtggat tgcgcactgg acccccctgag cgagaccaag  900
tgtacactga agtccttac cgtggagaag ggcatctatc agacatccaa tttcagggtg  960
```

-continued

```
cagccaaccg agtctatcgt gcgctttcct aatatcacaa acctgtgccc atttggcgag    1020
gtgttcaacg caaccaggtt cgcaagcgtg tacgcatgga atcggaagag aatctctaac    1080
tgcgtggccg actatagcgt gctgtacaac tctgccagct tctccacctt taagtgctat    1140
ggcgtgagcc ccacaaagct gaatgacctg tgctttacca acgtgtacgc cgattccttc    1200
gtgatcaggg gcgacgaggt gagacagatc gcacctggcc agacaggcaa gatcgccgac    1260
tacaattata agctgccaga cgatttcacc ggctgcgtga tcgcctggaa ctctaacaat    1320
ctggatagca aagtgggcgg caactacaat tatctgtaca ggctgtttcg caagtctaat    1380
ctgaagccct tcgagaggga catctctaca gagatctacc aggccggcag cacccccttgc   1440
aatggcgtgg agggctttaa ctgttatttc ccactgcagc gctacggctt ccagcccaca    1500
aacggcgtgg gctatcagcc ttaccgcgtg gtggtgctgt cttttgagct gctgcacgca    1560
ccagcaacag tgtgcggacc caagaagagc accaatctgg tgaagaacaa gtgcgtgaac    1620
ttcaacttca acgactgac cggaacaggc gtgctgaccg agtccaacaa gaagttcctg    1680
ccatttcagc agttcggcag ggacatcgca gataccacag acgccgtgcg cgacccacag    1740
accctggaga tcctggatat cacaccctgc tccttcggcg gcgtgtctgt gatcacaccc    1800
ggcaccaata caagcaacca ggtggccgtg ctgtatcagg acgtgaattg taccgaggtg    1860
cctgtggcca tccacgccga tcagctgacc ccaacatggc gggtgtactc caccggctct    1920
aacgtgttcc agacaagagc aggatgcctg atcggagcga agcacgtgaa caattcctat    1980
gagtgcgaca tcccaatcgg cgccggcatc tgtgcctctt accagcccca gacaaacagc    2040
ccaggctccg ccagctccgt ggcatctcag agcatcatcg cctataccat gtccctgggc    2100
gccgagaaca gcgtggccta ctctaacaat agcatcgcca tcccaaccaa cttcacaatc    2160
tccgtgacca cagagatcct gcccgtgagc atgaccaaga catccgtgga ctgcacaatg    2220
tatatctgtg gcgattccac cgagtgctct aacctgctgc tgcagtacgg cagcttttgt    2280
acccagctga ataggccct gacaggaatc gcagtggagc aggataagaa cacacaggag    2340
gtgttcgccc aggtgaagca gatctacaag accccacca tcaaggactt tggcggcttc    2400
aatttttccc agatcctgcc agatccctcc aagccttcta gcggagctt tatcgaggac    2460
ctgctgttca caaggtgac cctggccgat gccggcttca tcaagcagta tggcgattgc    2520
ctgggcgaca tcgccgccag agacctgatc tgtgcccaga gtttaatgg cctgaccgtg    2580
ctgcctccac tgctgacaga tgagatgatc gcacagtaca caagcgccct gctggcagga    2640
accatcacat ccgatggac cttcggcgca ggagccgccc tgcagatccc atttgccatg    2700
cagatggcct atcgcttcaa cggcatcggc gtgacccaga atgtgctgta cgagaaccag    2760
aagctgatcg ccaatcagtt taactccgcc atcggcaaga tccaggacag cctgtctagc    2820
acagcatccg ccctgggcaa gctgcaggat gtggtgaatc agaacgccca ggccctgaat    2880
accctggtga agcagctgtc ctctaacttc ggcgccatca gctccgtgct gaatgatatc    2940
ctgagcaggc tggaccccccc tgaggcagag gtgcagatcg acaggctgat cacaggccgc    3000
ctgcagtccc tgcagaccta tgtgacacag cagctgatcc gggccgccga gatcagagcc    3060
tctgccaatc tggccgccac caagatgtcc gagtgcgtgc tgggccagtc taagagagtg    3120
gacttttgtg gcaagggcta tcacctgatg agcttccctc agtccgcccc cacacggagtg    3180
gtgtttctgc acgtgaccta cgtgcccgcc caggagaaga acttcaccac agcccctgcc    3240
atctgccacg atggcaaggc ccactttcca agggagggcg tgttcgtgag caacggcacc    3300
cactggtttg tgacacagcg caatttctac gagccccaga tcatcaccac agacaatacc    3360
ttcgtgagcg gcaactgtga cgtggtcatc ggcatcgtga caataccgt gtatgatccc    3420
ctgcagcctg agctggacag ctttaaggag gagctggata agtacttcaa gaatcacacc    3480
tcccccgacg tggatctggg cgacatctct ggcatcaatg cctgtgtgga gaacatccag    3540
aaggagatcg acagactgaa cgaggtggcc aagaatctga acgagtctct gatcgatctg    3600
caggagctgg gcaagtatga gcagggcagc ggatacatcc cagaggcacc aagggacgga    3660
caggcatacg tgcgcaagga tggcgagtgg gtgctgctga gcaccttcct gggcggcggc    3720
```

```
SEQ ID NO: 3              moltype = AA  length = 300
FEATURE                  Location/Qualifiers
source                   1..300
                         mol_type = protein
                         organism = Severe acute respiratory syndrome coronavirus 2
                         note = SARS-CoV-2
SEQUENCE: 3
MGGTAARLGA VILFVVIVGL HGVRGGSRVQ PTESIVRFPN ITNLCPFGEV FNATRFASVY    60
AWNRKRISNC VADYSVLYNS ASFSTFKCYG VSPTKLNDLC FTNVYADSFV IRGDEVRQIA   120
PGQTGKIADY NYKLPDDFTG CVIAWNSNNL DSKVGGNYNY LYRLFRKSNL KPFERDISTE   180
IYQAGSTPCN GVEGFNCYFP LQSYGFQPTN GVGYQPYRVV VLSFELLHAP ATVCGPKKST   240
IYQAGSTPCN GVEGFNCYFP LQSYGFQPTN GVGYQPYRVV VLSFELLHAP ATVCGPKKST   300

SEQ ID NO: 4              moltype = DNA  length = 900
FEATURE                  Location/Qualifiers
misc_feature             1..900
                         note = Synthetic Construct
source                   1..900
                         mol_type = other DNA
                         organism = synthetic construct
SEQUENCE: 4
atgggaggga ctgccgccag gttgggggcc gtgattttgt ttgtcgtcat agtgggcctc    60
catggggtcc gcggtggatc cagggtgcag ccaaccgagt ctatcgtgcg ctttcctaat   120
atcacaaacc tgtgcccatt tggcgaggtg ttcaacgcaa ccaggttcgc aagcgtgtac   180
gcatggaatc ggaagagaat ctctaactgc gtggccgact atagcgtgct gtacaactct   240
gccagcttct ccacctttaa gtgctatggc gtgagcccca aaagctgaa tgacctgtgc   300
tttaccaacg tgtacgccga ttccttcgtg atcaggggcg acgaggtgag acagatcgca   360
cctggccaga ggcaagat cgccgactac aattataagc tgccagacga tttcaccggc   420
tgcgtgatcg cctggaactc taacaatctg atagcaaag tgggcggcaa ctacaattat   480
ctgtacaggc tgtttcgcaa gtctaatctg aagcccttcg agaggacat ctctacagag   540
atctaccagg ccggcagcac cccttgcaat ggcgtggagg ctttaactg ttatttccca   600
ctgcagagct acggcttcca gcccacaaac ggcgtgggct atcagcctta ccgcgtggtg   660
```

-continued

```
gtgctgtctt ttgagctgct gcacgcacca gcaacagtgt gcggacccaa gaagagcacc    720
aatctggtga agaacaagtg cgtgaacttc aacttcaacg gactgaccgg aacaggcgtg    780
ctgaccgagt ccaacaagaa gttcctgcca tttcagcagt tcggcaggga catcgcagat    840
accacagacg ccgtgcgcga cccacagacc ctggagatcc tggatatcac accctgctcc    900

SEQ ID NO: 5             moltype = AA  length = 299
FEATURE                  Location/Qualifiers
source                   1..299
                         mol_type = protein
                         organism = Severe acute respiratory syndrome coronavirus 1
                         note = SARS-CoV-1
SEQUENCE: 5
MGGTAARLGA VILFVVIVGL HGVRGGSRVV PSGDVVRFPN ITNLCPFGEV FNATKFPSVY    60
AWERKKISNC VADYSVLYNS TFFSTFKCYG VSATKLNDLC FSNVYADSFV VKGDDVRQIA    120
PGQTGVIADY NYKLPDDFMG CVLAWNTRNI DATSTGNYNY KYRYLRHGKL RPFERDISNV    180
PFSPDGKPCT PPALNCYWPL NDYGFYTTTG IGYQPYRVVV LSFELLNAPA TVCGPKLSTD    240
LIKNQCVNFN FNGLTGTGVL TPSSKRFQPF QQFGRDVSDF TDSVRDPKTS EILDISPCA     299

SEQ ID NO: 6             moltype = DNA  length = 897
FEATURE                  Location/Qualifiers
misc_feature             1..897
                         note = Synthetic Construct
source                   1..897
                         mol_type = other DNA
                         organism = synthetic construct
SEQUENCE: 6
atgggaggga ctgccgccag gttggggggcc gtgattttgt ttgtcgtcat agtgggcctc    60
catggggtcc gcggtggatc ccgggtggtg cccagcggcg atgtggtgag attccccaat    120
atcaccaacc tgtgcccttt cggcgaggtg tttaatgcca caaagttccc ttccgtgtac    180
gcctgggagc gcaagaagat ctccaactgc gtggccgact actctgtgct gtataatagc    240
accttcttca gcaccttcaa gtgctacggc gtgagcgcca ccaagctgaa tgacctgtgc    300
ttctccaacg tgtatgccga ttcttttgtg gtgaagggcg acgatgtgcg gcagatcgca    360
ccaggacaga ccggcgtgat cgcagactac aactataagc tgcccgacga tttcatgggc    420
tgcgtgctgg cctggaatac aagaaacatc gatgccacaa gcaccggcaa ctacaattat    480
aagtaccggt atctgagaca cggcaagctg cggcctttcg agagagacat cagcaatgtg    540
ccttttccc cagatggcaa gccttgcacc cccctgccc tgaattgtta ctggccactg    600
aacgactacg gcttctatac cacaaccggc atcggctacc agccatatcg ggtggtggtg    660
ctgtctttg agctgctgaa cgcaccagca accgtgtgcg gacccaagct gagcacagat    720
ctgatcaaga atcagtgcgt gaacttcaac ttcaacggac tgacaggaac cggcgtgctg    780
accccatcta gcaagaggtt ccagcccttt cagcagttcg gccgcgacgt gtctgatttc    840
accgacagcg tgagggaccc caagacaagc gagatcctgg atatctcccc ttgcgcc      897

SEQ ID NO: 7             moltype = AA  length = 214
FEATURE                  Location/Qualifiers
REGION                   1..214
                         note = Synthetic Construct
source                   1..214
                         mol_type = protein
                         organism = synthetic construct
SEQUENCE: 7
DIQMTQSPSS LSASVGDRVT ITCRASQDIS SYLNWYQQKP GKAPKLLIYY TSRLHSGVPS    60
RFSGSGSGTD FTFTISSLQP EDIATYYCQQ GNTLPYTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 8             moltype = AA  length = 447
FEATURE                  Location/Qualifiers
REGION                   1..447
                         note = Synthetic Construct
SITE                     1
                         note = misc_feature - Xaa is pyroglutamic acid residue
source                   1..447
                         mol_type = protein
                         organism = synthetic construct
SEQUENCE: 8
XVQLQESGPG LVRPSQTLSL TCTVSGYSIT SDHAWSWVRQ PPGRGLEWIG YISYSGITTY    60
NPSLKSRVTM LRDTSKNQFS LRLSSVTAAD TAVYYCARSL ARTTAMDYWG QGSLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSRDEL    360
TKNQSLTCLV KGFYPSDIAV EWESNGQPEN NYKTTPPVLD SDGSFFLYSK LTVDKSRWQQ    420
GNVFSCSVMH EALHNHYTQK SLSLSPG                                        447
```